United States Patent
Gaweco et al.

(10) Patent No.: US 9,701,663 B2
(45) Date of Patent: Jul. 11, 2017

(54) SULFONAMIDE RETINOIC ACID RECEPTOR-RELATED ORPHAN RECEPTOR MODULATORS AND USES THEREOF

(71) Applicant: INNOV17 LLC, Brooklyn, NY (US)

(72) Inventors: Anderson Gaweco, Brooklyn, NY (US); Jefferson Tilley, Brend, OR (US); James Blinn, O'Fallon, MO (US)

(73) Assignee: INNOV17 LLC, Brooklyn, NY (US)

( * ) Notice: Subject to any disclaimer, the term of this patent is extended or adjusted under 35 U.S.C. 154(b) by 55 days.

(21) Appl. No.: 14/808,269

(22) Filed: Jul. 24, 2015

(65) Prior Publication Data

US 2016/0024056 A1    Jan. 28, 2016

Related U.S. Application Data

(60) Provisional application No. 62/029,087, filed on Jul. 25, 2014.

(51) Int. Cl.
| | |
|---|---|
| C07D 403/14 | (2006.01) |
| C07D 401/14 | (2006.01) |
| C07D 487/08 | (2006.01) |
| C07D 405/14 | (2006.01) |
| A61K 31/55 | (2006.01) |
| A61K 31/46 | (2006.01) |
| A61K 31/435 | (2006.01) |
| A61K 31/4155 | (2006.01) |

(52) U.S. Cl.
CPC ......... *C07D 403/14* (2013.01); *C07D 401/14* (2013.01); *C07D 405/14* (2013.01); *C07D 487/08* (2013.01)

(58) Field of Classification Search
CPC combination set(s) only.
See application file for complete search history.

(56) References Cited

U.S. PATENT DOCUMENTS

| | | | |
|---|---|---|---|
| 6,300,342 B1 | 10/2001 | Heckel et al. | |
| 6,534,535 B1 | 3/2003 | Zhu et al. | |
| 8,143,285 B2 * | 3/2012 | Kugimiya | C07D 401/04 514/323 |
| 2007/0054903 A1 | 3/2007 | Kim et al. | |
| 2014/0187554 A1 | 7/2014 | Kamenecka et al. | |
| 2014/0275011 A1 * | 9/2014 | Mastracchio | C07D 401/04 514/210.18 |

FOREIGN PATENT DOCUMENTS

| | | |
|---|---|---|
| WO | 2011115892 | 9/2011 |
| WO | 2013159095 | 10/2013 |
| WO | 2014028597 | 2/2014 |

OTHER PUBLICATIONS

The International Search Report and Written Opinion, issued on Oct. 26, 2015, in the corresponding PCT Patent Application No. PCT/US15/41924.

* cited by examiner

*Primary Examiner* — Michael Barker
*Assistant Examiner* — Amanda L Aguirre

(57) ABSTRACT

Provided herein are compounds of the formula (I):

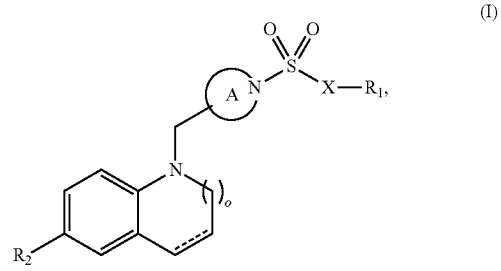

as well as pharmaceutically acceptable salts thereof, wherein the substituents are as those disclosed in the specification. These compounds, and the pharmaceutical compositions containing them, are useful for the treatment of Retinoic Acid Receptor-Related Orphan Receptor regulated diseases and disorders.

35 Claims, No Drawings

SULFONAMIDE RETINOIC ACID RECEPTOR-RELATED ORPHAN RECEPTOR MODULATORS AND USES THEREOF

FIELD OF THE INVENTION

The invention relates to Retinoic Acid Receptor-Related Orphan Receptor (ROR) regulated diseases and disorders. More particularly, the invention relates to ROR modulators; compositions comprising a therapeutically effective amount of a ROR modulator; and methods for treating or preventing ROR regulated diseases and disorders. All documents cited to or relied upon below are expressly incorporated herein by reference in their entirety.

BACKGROUND OF THE INVENTION

There are high unmet medical needs in the few established therapies for several autoimmune, inflammatory, metabolic and oncologic diseases. Despite the diverse clinical manifestations of these diseases, Retinoic Acid Receptor-Related Orphan Receptors (RORs) regulate and contribute to the pathogenesis of these diseases through modulation of immune responses and lipid/glucose homeostasis. Only recently has the critical regulatory role of RORs been well-characterized and target validated in several animal models of some of these diseases. RORs are transcription factors which belong to the nuclear hormone receptor superfamily (Jetten (2009) *Nucl. Recept. Signal.*, 7:e003; Jetten et al. (2013) *Front Endocrinol.* (Lausanne), 4:1; Jetten & Joo (2006) *Adv. Dev. Biol.*, 16:313-355). The ROR subfamily consists of three major isoforms: RORα (NR1F1), RORβ (NRIF2), and RORγ (NRIF3), encoded by the RORA, RORB and RORC genes, respectively. RORs are multidomain proteins that contain four principal domains typical of nuclear receptors: a highly variable N-terminal A/B domain, a highly conserved DNA-binding domain (DBD), a ligand binding domain (LBD) that contains the ligand-dependent activation function-2 (AF-2), and a hinge domain between the DBD and LBD. Each ROR gene through alternative splicing and promoter usage generates several ROR isoforms that differ only in their amino-terminus. In humans, there are four RORα isoforms (RORα1-4), one RORβ1 isoform, and two RORγ isoforms (RORγ1 and RORγ2 [RORγt]) that are expressed in a highly tissue-specific manner. RORα and RORγ play an important role in the regulation of lipid/glucose homeostasis, cellular metabolism, immune function and circadian rhythms, and have been implicated in the pathogenesis of several autoimmune, inflammatory and metabolic diseases (Burris et al. (2012) *Chem. Biol.*, 19:51-59; Burris et al. (2013) *Pharmacol. Rev.*, 65:710-778; Huh & Littman (2012) *Eur. J. Immunol.*, 42:2232-2237; Jetten (2009) *Nucl. Recept. Signal.*, 7:e003; Jetten et al. (2013) *Front Endocrinol.* (Lausanne), 4:1). Synthetic ligands have been described that interact with the RORα and RORγ LBD functioning as a switch that induces a ROR LBD conformational change. Such change promotes the recruitment and displacement of regulatory coactivator and corepressor proteins and upon ROR DBD binding to the ROR responsive element of the target genes lead to the induction or inhibition of ROR-regulated gene transcriptional activity. Therefore, small molecule drugs that bind to the nuclear receptor LBDs such as ROR could elicit a variety of pharmacological responses, including activation (agonists), inactivation (antagonists or non-agonists), and for receptors that are constitutively active, ligands can down-regulate the constitutive response (inverse agonists).

RORγt is the master regulator of human T Helper 17 ($T_H17$) cell differentiation, function and cytokine production (Ivanov et al. (2006) *Cell*, 126:1121-1133). The critical role of $T_H17$ cells in the development or resolution of autoimmune, inflammatory, metabolic and oncologic diseases has been established and is conferred by its signature proinflammatory cytokines IL-17A, IL-17F, IL-17AF, IL-21, IL-22 (Ghoreschi et al. (2010) *Nature*, 467:967-971; Kojetin & Burris (2014) *Nat. Rev. Drug Discov.*, 13:197-216; Lee et al. (2012) *Nat. Immunol.*, 13:991-999; Miossec et al. (2009) *N. Engl. J. Med.*, 361:888-898; Miossec & Kolls (2012) *Nat. Rev. Drug Discov.*, 11:763-776; Zepp et al. (2011) *Trends Immunol.*, 32:232-239). In addition to $T_H17$ cells, other sources of $T_H17$ cytokines include γ/δ T cells and innate lymphoid cells; however, $T_H17$ cells are distinguished by the specific regulation of RORγ and RORγt for cytokine transcriptional output and effector functions, and also by RORα (Cua & Tato (2010) *Nat. Rev. Immunol.*, 10:479-489; Huh & Littman (2012) *Eur. J. Immunol.*, 42:2232-2237; Ivanov et al. (2006) *Cell*, 126:1121-1133; Spits & Di Santo (2011) *Nat. Immunol.*, 12:21-27; Sutton et al. (2012) *Eur. J. Immunol.*, 42:2221-2231; Yang et al. (2008) *Immunity.*, 28:29-39). Also, in several autoimmune disease models, there is a relative imbalance of increased pathologic $T_H17$ cells over low numbers of protective immunosuppressive CD4$^+$CD25$^+$ Foxp3$^+$ regulatory T cells [$T_{Reg}$](Edwards et al. (2011) *J. Neurol.*, 258:1518-1527; Littman & Rudensky (2010) *Cell*, 140:845-858). Targeting RORα, RORγ and/or RORγt could have a broader anti-inflammatory effect on the combined inhibition of all $T_H17$ cytokine production and inflammatory cellular function, and in the induction and expansion of suppressive $T_{Reg}$ cells, important in autoimmune and inflammatory disease resolution, and may also have therapeutic potential in metabolic diseases such as diet-induced insulin resistance known to be regulated by ROR. Since both RORγ1 and RORγt protein isoforms, contain identical LBDs, small molecule RORγ modulators that inhibit RORγt activity will also inhibit RORγ. Furthermore, RORα similarly plays an important regulatory role in the development or resolution of autoimmune and inflammatory disorders, and also in metabolic and oncologic diseases (Kojetin & Burris (2014) *Nat. Rev. Drug Discov.*, 13:197-216). RORα critically regulates lipid and glucose homeostasis and cellular metabolism that contribute to the development of metabolic diseases. Furthermore, RORα expression is downregulated in several types of cancer. Therefore, as ligand-dependent transcription factors, it is desirable to prepare compounds that modulate RORα and/or RORγ activity which can be used in the treatment of RORα- and/or RORγ-regulated autoimmune, inflammatory, metabolic and oncologic diseases.

SUMMARY OF THE INVENTION

The present invention is directed to A compound of formula (I):

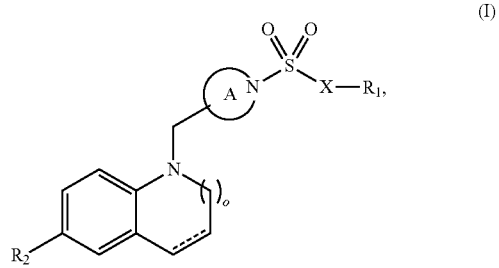

wherein:

A is a mono- or bicyclic 5- to 8-membered heterocyclic ring having one ring carbon replaced by N as shown, said ring optionally mono- or bi-substituted on one or more ring carbons independently with a $C_1$-$C_6$ alkyl group;

X is —$(CH_2)_n$—;

$R_1$ is —$C_1$-$C_6$ alkyl, optionally substituted with one or more —OH, halogen or —CN, phenyl, optionally mono- or bisubstituted independently with halogen, alkoxy, $C_1$-$C_6$ alkyl, —CN, -sulfonyloxy, -nitrile, alkylsulfonyl, halo-$C_1$-$C_6$ alkyl or $C_1$-$C_5$ cycloalkyl, cycloalkyl, optionally substituted, heterocycle, optionally substituted or a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN, nitrile or perfluorinated $C_1$-$C_6$ alkyl;

$R_2$ is a 5- to 7-membered heteroaryl group having one, two or three ring carbons independently replaced by N, O or S, said heteroaryl optionally mono- or bi-substituted independently with H, $C_1$-$C_6$ alkyl, —CN or (=O);

⚌ is a single or double bond;

o is 0 or 1; and n is 0, 1 or 2;

or a pharmaceutically acceptable salt thereof.

The present invention is also directed to pharmaceutically acceptable salts of the compounds of formula (I), pharmaceutical compositions and to methods of treating diseases and disorders. The compounds and compositions disclosed herein are ROR modulators and useful for the treatment of ROR-mediated diseases and disorders.

DETAILED DESCRIPTION

The invention is based in part on the discovery of ROR modulators, which interact with RORα and/or RORγ and thereby inhibit or induce RORα and/or RORγ activity, and RORα-and/or RORγ-regulated target gene and protein expression. The invention is also based on compositions comprising an effective amount of a ROR modulator; and methods for treating or preventing disorders regulated by RORα and/or RORγ, comprising the administration of a therapeutically effective amount of a ROR modulator.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

The following definitions are used in connection with the ROR modulators:

"ROR" refers to RORα and/or RORγ isoforms.

"RORα" refers to all isoforms encoded by the RORA gene.

"RORγ" refers to all isoforms encoded by the RORC gene which include RORγ1 and RORγt [RORγ2].

"RORα modulator" refers to a chemical compound that modulates, either directly or indirectly, the activity of RORα. RORα modulators include antagonists/non-agonists, inverse agonists and agonists of RORα.

"RORγ modulator" refers to a chemical compound that modulates, either directly or indirectly, the activity of RORγ. RORγ modulators include antagonists/non-agonists, inverse agonists and agonists of RORγ.

The term "ROR modulator" includes any and all possible isomers, stereoisomers, enantiomers, diastereomers, tautomers, pharmaceutically acceptable salts, hydrates, solvates, and prodrugs of the ROR modulators described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl.

The term "heterocycle" as used herein refers to a cyclic hydrocarbon containing 3-12 atoms wherein at least one of the atoms is an O, N, or S wherein a monocyclic heterocycle may contain up to two double bonds. Examples of heterocycles include, but are not limited to, aziridine, oxirane, thiirane, azetidine, oxetane, morpholine, thiomorpholine, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to an aromatic mono- or polycyclic radical of 5 to 12 atoms having at least one aromatic ring containing one, two, or three ring heteroatoms selected from N, O, and S, with the remaining ring atoms being C. Examples of heteroaryls include, but are not limited to, furan, thiophene, pyrrole, pyrroline, oxazole, thiazole, imidazole, pyrazole, isoxazole, isothiazole, triazole, thiadiazole, pyrane, pyridine, pyridazine, pyrimidine, pyrazine and triazene.

It is understood that any of the substitutable hydrogens on an alkyl, cycloalkyl, heterocycle and heteroaryl can be substituted independently with one or more substituents, for example 1, 2 or 3 substituents. Examples of substituents include, but are not limited to, halogen (e.g., 1, 2 or 3 halogens), $C_1$-$C_3$ alkyl, hydroxyl, alkoxy, oxo and cyano groups.

A "patient" is a mammal, e.g., a human, mouse, rat, guinea pig, dog, cat, horse, cow, pig, or non-human primate, such as a monkey, chimpanzee, baboon or rhesus monkey, and the terms "patient" and "subject" are used interchangeably herein.

The invention also includes pharmaceutical compositions comprising a therapeutically effective amount of a ROR modulator and a pharmaceutically acceptable carrier. The invention includes a ROR modulator provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "therapeutically effective amount" when used in connection with a ROR modulator is an amount effective for treating or preventing a ROR-regulated disease or disorder.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a ROR modulator.

The term "optionally substituted," as used in this disclosure, means one or more suitable substituent can independently replace one or more hydrogens bound to a carbon, nitrogen, or oxygen. When a substituent is oxo (i.e., =O) then 2 hydrogens on the atom are replaced by a single O. Suitable substituents are selected from the following which include, but are not limited to, hydroxyl, halogen, perfluorinated $C_1$-$C_6$ alkyl, amine, —$C_1$-$C_{12}$ alkyl, —$C_2$-$C_{12}$ alkene, —$C_2$-$C_{12}$ alkyne, —($C_1$-$C_3$ alkyl)-(cycloalkyl), aryl, alkyl-aryl, —C(O)H, —C(O)OH, —C(O)alkyl, —C(O)—O-alkyl, —C(O)NH(alkyl), benzyl, —C(O)NH$_2$, —C(O)N(alkyl)$_2$, —NHC(O)H, —NHC(O)alkyl, —SO$_2$(alkyl), —SO$_2$NH$_2$, —SO$_2$NH(alkyl), —SO$_2$N(alkyl)$_2$, S, CN, and SCN. It will be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables within any of the Formulae represented herein are permissible only if such combinations result in stable compounds or useful synthetic intermediates wherein stable implies a reasonable pharmologically relevant half-life at physiological conditions.

The following abbreviations are used herein and have the indicated definitions: ACTB is β-actin, AF-2 is activation function-2, AIBN is azobisisobutyronitrile, Boc and BOC are tert-butoxycarbonyl, Boc$_2$O is di-tert-butyl dicarbonate, BOP is (Benzotriazol-1-yloxy)tris(dimethylamino)phosphonium hexafluorophosphate, BSA is bovine serum albumin, CD is cluster of differentiation, CDI is 1,1'-carbonyldiimidazole, DBD is DNA-binding domain, DCC is N,N'-dicyclohexylcarbodiimide, DIEA and DIPEA is N,N-diisopropylethylamine, DMAP is 4-dimethylaminopyridine, DMEM is Dulbecco's Modified Eagle Medium, DMF is N,N-dimethylformamide, DMSO is dimethyl sulfoxide, DOSS is sodium dioctyl sulfosuccinate, $EC_{50}$ is half maximal effective concentration, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, FOXP3 is forkhead box P3, G-CSF is granulocyte colony-stimulating factor, h is hour, HATU is 2-(7-aza-1H-benzotriazole-1-yl)-1,1,3,3-tetramethyluronium hexafluorophosphate, HIV is human immunodeficiency virus, HOBt is 1-Hydroxybenzotriazole, HPMC is hydroxypropyl methylcellulose, HPRT1 is hypoxanthine phosphoribosyltransferase 1, $IC_{50}$ is half maximal inhibitory concentration, IFN-γ is interferon gamma, IL is interleukin, IL-23R is interleukin 23 receptor, LAH is lithium aluminum hydride, LBD is ligand binding domain, MIQE is minimum information for publication of quantitative real-time PCR experiments, MTBE is methyl tert-butyl ether, NBS is N-bromosuccinnide, NMP is N-methyl-2-pyrrolidone, oxone is potassium peroxymonosulfate, PBMCs is peripheral blood mononuclear cells, PCR is polymerase chain reaction, Pd/C is palladium on carbon, PGK1 is phosphoglycerate kinase, PPIA is peptidylprolyl isomerase A, REST is Relative Expression Software Tool, RORα is retinoic acid receptor-related orphan receptor alpha, RORγ is retinoic acid receptor-related orphan receptor gamma, TBAB is tetrabutylammonium bromide, TBP is terminal binding protein, TFA is trifluoroacetic acid, TFRC is transferrin receptor, TGF-β1 is transforming growth factor beta 1, $T_H17$ is T helper 17 cell, TGPS is tocopherol propylene glycol succinate, THF is tetrahydrofuran, TLC is thin layer chromatography, TR-FRET is time-resolved fluorescence resonance energy transfer and M is micromolar.

In one embodiment of the present invention, provided is a compound of formula (I):

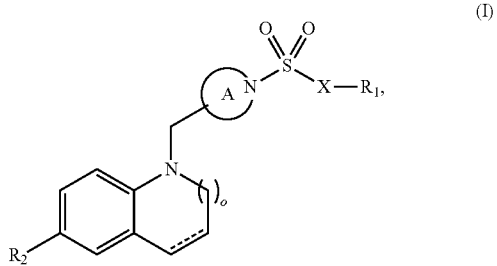

wherein:
A is a mono- or bicyclic 5- to 8-membered heterocyclic ring having one ring carbon replaced by N as shown, said ring optionally mono- or bi-substituted on one or more ring carbons independently with a $C_1$-$C_6$ alkyl group;
X is —$(CH_2)_n$—;
$R_1$ is —$C_1$-$C_6$ alkyl, optionally substituted with one or more —OH, halogen or —CN,
  phenyl, optionally mono- or bisubstituted independently with halogen, alkoxy, $C_1$-$C_6$ alkyl, —CN, -sulfonyloxy, -nitrile, alkylsulfonyl, halo-$C_1$-$C_6$ alkyl or $C_1$-$C_5$ cycloalkyl,
  cycloalkyl, optionally substituted,
  heterocycle, optionally substituted or
  a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN, nitrile or perfluorinated $C_1$-$C_6$ alkyl;
$R_2$ is a 5- to 7-membered heteroaryl group having one, two or three ring carbons independently replaced by N, O or S, said heteroaryl optionally mono- or bi-substituted independently with H, $C_1$-$C_6$ alkyl, —CN or (=O);
⸺ is a single or double bond;
o is 0 or 1; and
n is 0, 1 or 2;
or a pharmaceutically acceptable salt thereof.

In another embodiment, provided is a compound of formula (I), wherein A is unsubstituted piperidinyl, pyrrolidinyl, azepanyl or [2,2,1]bicycloazepinyl.

In another embodiment, provided is a compound of formula (I), wherein A is piperidinyl, pyrrolidinyl or azepanyl mono- or bi-substituted independently with a $C_1$-$C_6$ alkyl group.

In another embodiment, provided is a compound of formula (I), wherein A is piperidinyl, pyrrolidinyl or azepanyl mono-substituted with methyl.

In another embodiment, provided is a compound of formula (I), wherein A is piperidinyl, pyrrolidinyl or azepanyl bi-substituted with methyl.

In another embodiment, provided is a compound of formula (I), wherein X is methylene or ethylene.

In another embodiment, provided is a compound of formula (I), wherein X is absent.

In another embodiment, provided is a compound of formula (I), wherein $R_1$ is —$C_1$-$C_6$ alkyl In another embodiment, provided is a compound of formula (I), wherein $R_1$ is methyl, ethyl, propyl or t-butyl.

In another embodiment, provided is a compound of formula (I), wherein $R_1$ is unsubstituted phenyl.

In another embodiment, provided is a compound of formula (I), wherein $R_1$ is phenyl substituted with halogen, cyano, alkoxy, $C_1$-$C_6$ alkyl or halo-$C_1$-$C_6$-alkyl.

In another embodiment, provided is a compound of formula (I), wherein $R_1$ is chlorophenyl, fluorophenyl or dihalophenyl.

In another embodiment, provided is a compound of formula (I), wherein $R_1$ is methoxy-phenyl.

In another embodiment, provided is a compound of formula (I), wherein $R_1$ is methyl-phenyl, cyanophenyl or alkoxyphenyl.

In another embodiment, provided is a compound of formula (I), wherein $R_1$ is cycloalkyl.

In another embodiment, provided is a compound of formula (I), wherein $R_1$ is cyclohexyl.

In another embodiment, provided is a compound of formula (I), wherein $R_1$ is an unsubstituted 5- or 6-membered heteroaryl group having one or more ring carbons replaced by N In another embodiment, provided is a compound of formula (I), wherein $R_1$ is a 5- or 6-membered heteroaryl group having one or more ring carbons replaced by N, substituted with a $C_1$-$C_6$ alkyl group.

In another embodiment, provided is a compound of formula (I), wherein $R_1$ is pyridinyl.

In another embodiment, provided is a compound of formula (I), wherein $R_2$ is an unsubstituted 5- to 7-membered heteroaryl group having one, two or three ring carbons replaced by N.

In another embodiment, provided is a compound of formula (I), wherein $R_2$ is a 5- to 7-membered heteroaryl group having one, two or three ring carbons replaced by N, said heteroaryl group mono- or bi-substituted independently with H, $C_1$-$C_6$ alkyl, —CN or (=O).

In another embodiment, provided is a compound of formula (I), wherein $R_2$ is unsubstituted pyrazolyl, triazolyl, pyridinyl, pyrazinyl or thiazole.

In another embodiment, provided is a compound of formula (I), wherein $R_2$ is pyrazolyl or triazolyl.

In another embodiment, provided is a compound of formula (I), wherein $R_2$ is unsubstituted pyrazolyl.

In another embodiment, provided is a compound of formula (I), wherein $R_2$ is linked via a carbon atom.

In another embodiment, provided is a compound having the formula (Ia):

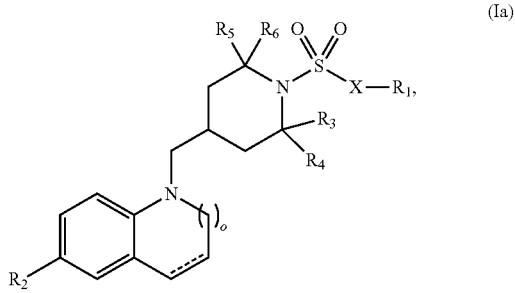

wherein:
X is —$(CH_2)_n$—;
$R_1$ is —$C_1$-$C_6$ alkyl, optionally substituted with one or more —OH, halogen or —CN, phenyl, optionally mono- or bisubstituted independently with halogen, alkoxy, $C_1$-$C_6$ alkyl, —CN, -sulfonyloxy, -nitrile, alkylsulfonyl, halo-$C_1$-$C_6$ alkyl or $C_1$-$C_5$ cycloalkyl, cycloalkyl, optionally substituted, heterocycle, optionally substituted or a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN, nitrile or perfluorinated $C_1$-$C_6$ alkyl;

$R_2$ is a 5- to 7-membered heteroaryl group having one, two or three ring carbons independently replaced by N, O or S, said heteroaryl optionally mono- or bi-substituted independently with H, $C_1$-$C_6$ alkyl, —CN or (=O);

$R_3$, $R_4$, $R_5$ and $R_6$ are independently —H or lower alkyl;

⋯ is a single or double bond;

o is 0 or 1; and n is 0, 1 or 2;

or a pharmaceutically acceptable salt thereof.

In another embodiment, provided is a compound having the formula (Ib):

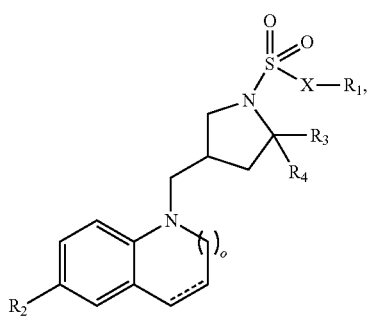

(Ib)

wherein:

X is —$(CH_2)_n$—;

$R_1$ is —$C_1$-$C_6$ alkyl, optionally substituted with one or more —OH, halogen or —CN, phenyl, optionally mono- or bisubstituted independently with halogen, alkoxy, $C_1$-$C_6$ alkyl, —CN, -sulfonyloxy, -nitrile, alkylsulfonyl, halo-$C_1$-$C_6$ alkyl or $C_1$-$C_5$ cycloalkyl, cycloalkyl, optionally substituted, heterocycle, optionally substituted, or a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN, nitrile or perfluorinated $C_1$-$C_6$ alkyl;

$R_2$ is a 5- to 7-membered heteroaryl group having one, two or three ring carbons independently replaced by N, O or S, said heteroaryl optionally mono- or bi-substituted independently with H, $C_1$-$C_6$ alkyl, —CN or (=O);

$R_3$ and $R_4$ are independently —H or lower alkyl;

⋯ is a single or double bond;

o is 0 or 1; and n is 0, 1 or 2;

or a pharmaceutically acceptable salt thereof.

In another embodiment, provided is a compound having the formula (Ic):

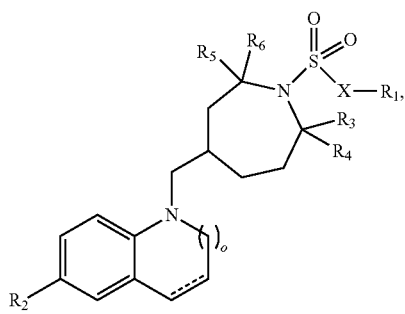

(Ic)

wherein:

X is —$(CH_2)_n$—;

$R_1$ is —$C_1$-$C_6$ alkyl, optionally substituted with one or more —OH, halogen or —CN, phenyl, optionally mono- or bisubstituted independently with halogen, alkoxy, $C_1$-$C_6$ alkyl, —CN, -sulfonyloxy, -nitrile, alkylsulfonyl, halo-$C_1$-$C_6$ alkyl or $C_1$-$C_5$ cycloalkyl, cycloalkyl, optionally substituted, heterocycle, optionally substituted, or a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN, nitrile or perfluorinated $C_1$-$C_6$ alkyl;

$R_2$ is a 5- to 7-membered heteroaryl group having one, two or three ring carbons independently replaced by N, O or S, said heteroaryl optionally mono- or bi-substituted independently with H, $C_1$-$C_6$ alkyl, —CN or (=O);

$R_3$, $R_4$, $R_5$ and $R_6$ are independently —H or lower alkyl;

⋯ is a single or double bond;

o is 0 or 1; and n is 0, 1 or 2;

or a pharmaceutically acceptable salt thereof.

In another embodiment, provided is a compound having the formula (Id):

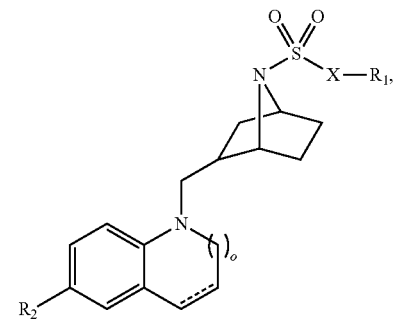

(Id)

wherein:

X is —$(CH_2)_n$—;

$R_1$ is —$C_1$-$C_6$ alkyl, optionally substituted with one or more —OH, halogen or —CN, phenyl, optionally mono- or bisubstituted independently with halogen, alkoxy, $C_1$-$C_6$ alkyl, —CN, -sulfonyloxy, -nitrile, alkylsulfonyl, halo-$C_1$-$C_6$ alkyl or $C_1$-$C_5$ cycloalkyl, cycloalkyl, optionally substituted, heterocycle, optionally substituted, or
a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN, nitrile or perfluorinated $C_1$-$C_6$ alkyl;

$R_2$ is a 5- to 7-membered heteroaryl group having one, two or three ring carbons independently replaced by N, O or S, said heteroaryl optionally mono- or bi-substituted independently with H, $C_1$-$C_6$ alkyl, —CN or (=O);

⁝⁝⁝ is a single or double bond;
o is 0 or 1; and
n is 0, 1 or 2;
or a pharmaceutically acceptable salt thereof.

In another embodiment, provided is a compound of formula (I), wherein said compound is:

1-((1-(phenylsulfonyl)piperidin-4-yl)methyl)-5-(1H-pyrazol-4-yl)-1H-indole,
1-((1-(benzylsulfonyl)piperidin-4-yl)methyl)-5-(1H-pyrazol-4-yl)-1H-indole,
1-((1-(phenethylsulfonyl)piperidin-4-yl)methyl)-5-(1H-pyrazol-4-yl)-1H-indole,
5-(1H-pyrazol-4-yl)-1-((1-((2,2,2-trifluoroethyl)sulfonyl)piperidin-4-yl)methyl)-1H-indole;
1-((1-(4-chlorophenylsulfonyl)piperidin-4-yl)methyl)-5-(1H-pyrazol-4-yl)-1H-indole,
5-(1H-pyrazol-4-yl)-1-((1-(pyridin-3-ylsulfonyl)piperidin-4-yl)methyl)-1H-indole or
1-((1-(2-fluorophenylsulfonyl)piperidin-4-yl)methyl)-5-(1H-pyrazol-4-yl)-1H-indole.
cis-1-((5-methyl-1-(phenylsulfonyl)pyrrolidin-3-yl)methyl)-5-(1H-pyrazol-4-yl)-1H-indole or
trans-1-((5-methyl-1-(phenylsulfonyl)pyrrolidin-3-yl)methyl)-5-(1H-pyrazol-4-yl)-1H-indole, In another embodiment, provided is a compound of formula (I), wherein said compound is:

1-((1-(phenylsulfonyl)pyrrolidin-3-yl)methyl)-5-(1H-pyrazol-4-yl)-1H-indole,
1-((1-(benzylsulfonyl)pyrrolidin-3-yl)methyl)-5-(1H-pyrazol-4-yl)-1H-indole,
1-((1-(phenethylsulfonyl)pyrrolidin-3-yl)methyl)-5-(1H-pyrazol-4-yl)-1H-indole,
1-((1-(tert-butylsulfonyl)pyrrolidin-3-yl)methyl)-5-(1H-pyrazol-4-yl)-1H-indole,
1-((5-methyl-1-(phenylsulfonyl)pyrrolidin-3-yl)methyl)-5-(1H-pyrazol-4-yl)-1H-indole,
1-((1-(benzylsulfonyl)-5-methylpyrrolidin-3-yl)methyl)-5-(1H-pyrazol-4-yl)-1H-indole,
((5-methyl-1-(phenethylsulfonyl)pyrrolidin-3-yl)methyl)-5-(1H-pyrazol-4-yl)-1H-indole,
1-((1-(tert-butylsulfonyl)-5-methylpyrrolidin-3-yl)methyl)-5-(1H-pyrazol-4-yl)-1H-indole,
1-((1-(phenylsulfonyl)azepan-4-yl)methyl)-5-(1H-pyrazol-4-yl)-1H-indole,
1-((1-(benzylsulfonyl)azepan-4-yl)methyl)-5-(1H-pyrazol-4-yl)-1H-indole,
1-((1-(phenethylsulfonyl)azepan-4-yl)methyl)-5-(1H-pyrazol-4-yl)-1H-indole,
1-((1-(tert-butylsulfonyl)azepan-4-yl)methyl)-5-(1H-pyrazol-4-yl)-1H-indole,
1-((7-(phenylsulfonyl)-7-azabicyclo[2.2.1]heptan-2-yl)methyl)-5-(1H-pyrazol-4-yl)-1H-indole,
1-((7-(benzylsulfonyl)-7-azabicyclo[2.2.1]heptan-2-yl)methyl)-5-(1H-pyrazol-4-yl)-1H-indole,
1-((7-(phenethylsulfonyl)-7-azabicyclo[2.2.1]heptan-2-yl)methyl)-5-(1H-pyrazol-4-yl)-1H-indole,
1-((7-(tert-butylsulfonyl)-7-azabicyclo[2.2.1]heptan-2-yl)methyl)-5-(1H-pyrazol-4-yl)-1H-indole,
1-((1-(phenylsulfonyl)piperidin-4-yl)methyl)-6-(1H-pyrazol-4-yl)-1,2,3,4-tetrahydroquinoline,
1-((1-(benzylsulfonyl)piperidin-4-yl)methyl)-6-(1H-pyrazol-4-yl)-1,2,3,4-tetrahydroquinoline,
1-((1-(phenethylsulfonyl)piperidin-4-yl)methyl)-6-(1H-pyrazol-4-yl)-1,2,3,4-tetrahydroquinoline,
1-((1-(tert-butylsulfonyl)piperidin-4-yl)methyl)-6-(1H-pyrazol-4-yl)-1,2,3,4-tetrahydroquinoline,
1-((5,5-dimethyl-1-(phenylsulfonyl)pyrrolidin-3-yl)methyl)-5-(1H-pyrazol-4-yl)-1H-indole,
1-((1-(benzylsulfonyl)-5,5-dimethylpyrrolidin-3-yl)methyl)-5-(1H-pyrazol-4-yl)-1H-indole,
1-((5,5-dimethyl-1-(phenethylsulfonyl)pyrrolidin-3-yl)methyl)-5-(1H-pyrazol-4-yl)-1H-indole,
1-((1-(tert-butylsulfonyl)-5,5-dimethylpyrrolidin-3-yl)methyl)-5-(1H-pyrazol-4-yl)-1H-indole,
5-(1H-pyrazol-4-yl)-1-((1-(m-tolylsulfonyl)piperidin-4-yl)methyl)-1H-indole,
1-((1-((4-methoxyphenyl)sulfonyl)piperidin-4-yl)methyl)-5-(1H-pyrazol-4-yl)-1H-indole,
1-((1-((4-fluorophenyl)sulfonyl)piperidin-4-yl)methyl)-5-(1H-pyrazol-4-yl)-1H-indole,
3-((4-((5-(1H-pyrazol-4-yl)-1H-indol-1-yl)methyl)piperidin-1-yl)sulfonyl)benzonitrile,
1-((1-((4-(difluoromethyl)phenyl)sulfonyl)piperidin-4-yl)methyl)-5-(1H-pyrazol-4-yl)-1H-indole,
1-((1-((3-fluorophenyl)sulfonyl)piperidin-4-yl)methyl)-5-(1H-pyrazol-4-yl)-1H-indole,
1-((1-((4-fluorophenyl)sulfonyl)-5,5-dimethylpyrrolidin-3-yl)methyl)-5-(1H-pyrazol-4-yl)-1H-indole,
1-((1-((2-fluorophenyl)sulfonyl)-5,5-dimethylpyrrolidin-3-yl)methyl)-5-(1H-pyrazol-4-yl)-1H-indole,
1-((1-((2,3-difluorophenyl)sulfonyl)-5,5-dimethylpyrrolidin-3-yl)methyl)-5-(1H-pyrazol-4-yl)-1H-indole,
1-((5,5-dimethyl-1-tosylpyrrolidin-3-yl)methyl)-5-(1H-pyrazol-4-yl)-1H-indole,
1-((1-((3-methoxyphenyl)sulfonyl)-5,5-dimethylpyrrolidin-3-yl)methyl)-5-(1H-pyrazol-4-yl)-1H-indole,
3-((4-((5-(1H-pyrazol-4-yl)-1H-indol-1-yl)methyl)-2,2-dimethylpyrrolidin-1-yl)sulfonyl)benzonitrile,
1-((1-((4-fluorophenyl)sulfonyl)-5-methylpyrrolidin-3-yl)methyl)-5-(1H-pyrazol-4-yl)-1H-indole,
1-((1-((3-fluorophenyl)sulfonyl)-5-methylpyrrolidin-3-yl)methyl)-5-(1H-pyrazol-4-yl)-1H-indole,
1-((1-((2-fluorophenyl)sulfonyl)-5-methylpyrrolidin-3-yl)methyl)-5-(1H-pyrazol-4-yl)-1H-indole,
1-((1-((2,3-difluorophenyl)sulfonyl)-5-methylpyrrolidin-3-yl)methyl)-5-(1H-pyrazol-4-yl)-1H-indole,
1-((5-methyl-1-tosylpyrrolidin-3-yl)methyl)-5-(1H-pyrazol-4-yl)-1H-indole,
1-((1-((3-methoxyphenyl)sulfonyl)-5-methylpyrrolidin-3-yl)methyl)-5-(1H-pyrazol-4-yl)-1H-indole,
3-((4-((5-(1H-pyrazol-4-yl)-1H-indol-1-yl)methyl)-2-methylpyrrolidin-1-yl)sulfonyl)benzonitrile,
1-((5-methyl-1-(m-tolylsulfonyl)pyrrolidin-3-yl)methyl)-5-(1H-pyrazol-4-yl)-1H-indole,
1-((1-((4-fluorophenyl)sulfonyl)-5-methylpyrrolidin-3-yl)methyl)-5-(1H-pyrazol-4-yl)-1H-indole,
1-((1-((3-fluorophenyl)sulfonyl)-5-methylpyrrolidin-3-yl)methyl)-5-(1H-pyrazol-4-yl)-1H-indole,
1-((1-((2-fluorophenyl)sulfonyl)-5-methylpyrrolidin-3-yl)methyl)-5-(1H-pyrazol-4-yl)-1H-indole,
1-((1-((2,3-difluorophenyl)sulfonyl)-5-methylpyrrolidin-3-yl)methyl)-5-(1H-pyrazol-4-yl)-1H-indole, 1-((5-methyl-1-tosylpyrrolidin-3-yl)methyl)-5-(1H-pyrazol-4-yl)-1H-indole, 1-((1-((3-methoxyphenyl)sulfonyl)-5-methylpyrrolidin-3-yl)methyl)-5-(1H-pyrazol-4-yl)-1H-indole, 3-((4-((5-(1H-pyrazol-4-yl)-1H-indol-1-yl)methyl)-2-methylpyrrolidin-1-yl)sulfonyl)benzonitrile or 1-((5-methyl-1-(m-tolylsulfonyl)pyrrolidin-3-yl)methyl)-5-(1H-pyrazol-4-yl)-1H-indole.

In another embodiment, provided is a pharmaceutical composition, comprising a therapeutically effective amount of a compound according to formula (I), or a pharmaceutically acceptable salt thereof, and a pharmaceutically acceptable carrier.

In another embodiment, provided is a method of treating a Retinoic Acid Receptor-Related Orphan Receptor regulated disease or disorder, comprising the step of administering a therapeutically effective amount of a compound according to formula (I), or a pharmaceutically acceptable salt thereof, to a patient in need thereof.

In another embodiment, provided is a method of treating a Retinoic Acid Receptor-Related Orphan Receptor regulated disease or disorder, wherein said disease or disorder is an autoimmune, inflammatory, metabolic or oncologic disease or disorder.

In another embodiment, provided is a method of treating a Retinoic Acid Receptor-Related Orphan Receptor regulated disease or disorder, wherein said disease or disorder is rheumatoid arthritis, psoriasis, psoriatic arthritis, polymyalgia rheumatica, multiple sclerosis, lupus, uveitis, inflammatory bowel disease, ankylosing spondylitis, vasculitis, atherosclerosis, macular degeneration, diabetes, obesity, cancer, asthma or chronic obstructive pulmonary disease.

Certain compound of the present invention of formula (I) are further exemplified by structure as follows:

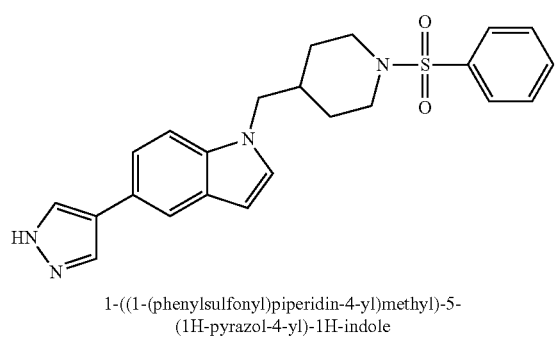

1-((1-(phenylsulfonyl)piperidin-4-yl)methyl)-5-(1H-pyrazol-4-yl)-1H-indole

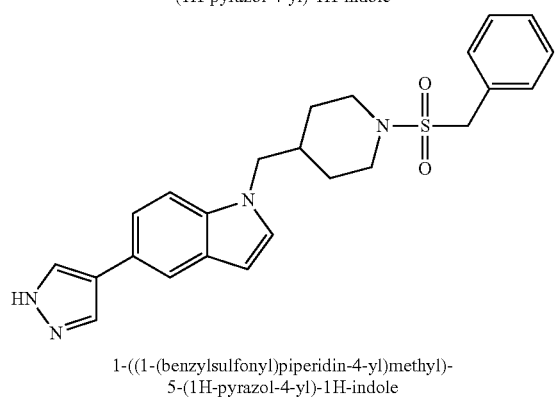

1-((1-(benzylsulfonyl)piperidin-4-yl)methyl)-5-(1H-pyrazol-4-yl)-1H-indole

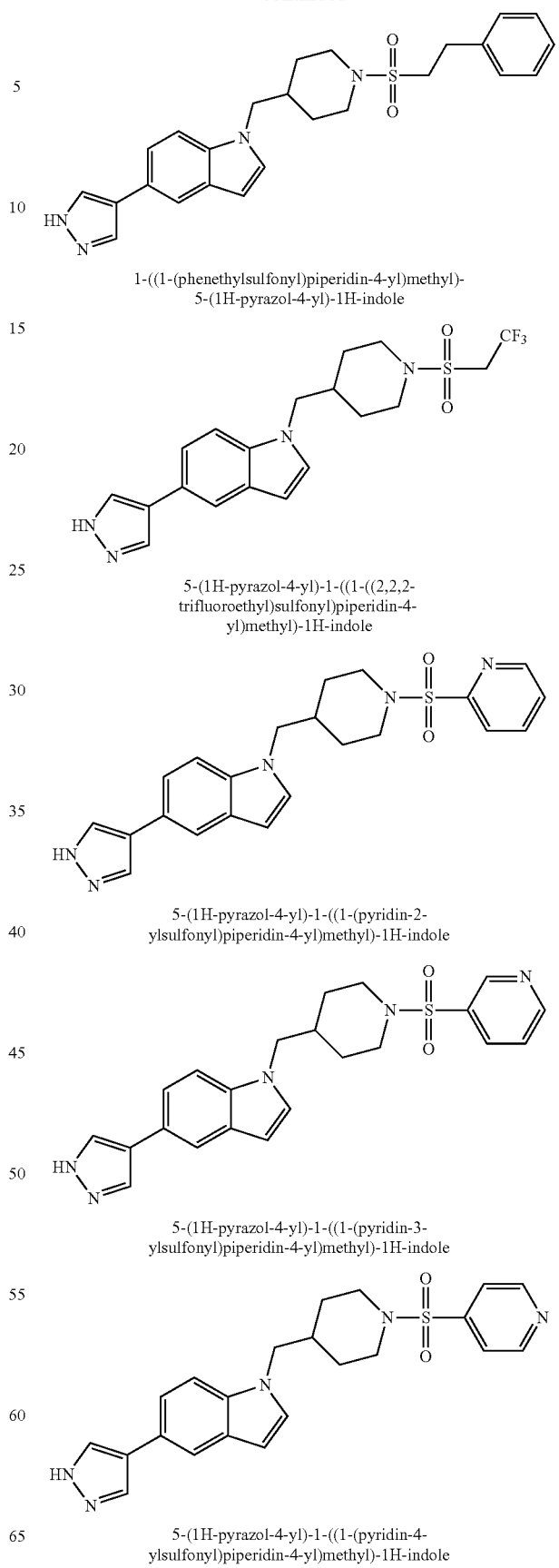

1-((1-(phenethylsulfonyl)piperidin-4-yl)methyl)-5-(1H-pyrazol-4-yl)-1H-indole 5-(1H-pyrazol-4-yl)-1-((1-((2,2,2-trifluoroethyl)sulfonyl)piperidin-4-yl)methyl)-1H-indole 5-(1H-pyrazol-4-yl)-1-((1-(pyridin-2-ylsulfonyl)piperidin-4-yl)methyl)-1H-indole 5-(1H-pyrazol-4-yl)-1-((1-(pyridin-3-ylsulfonyl)piperidin-4-yl)methyl)-1H-indole 5-(1H-pyrazol-4-yl)-1-((1-(pyridin-4-ylsulfonyl)piperidin-4-yl)methyl)-1H-indole -continued

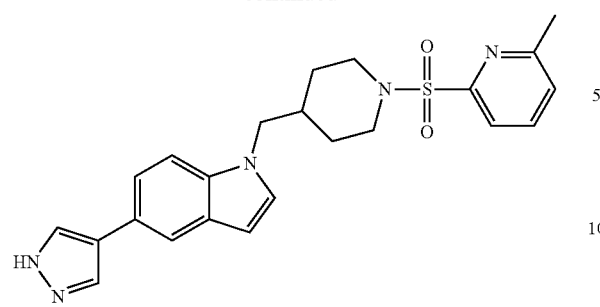

1-((1-((6-methylpyridin-2-yl)sulfonyl)piperidin-4-yl)methyl)-5-(1H-pyrazol-4-yl)-1H-indole

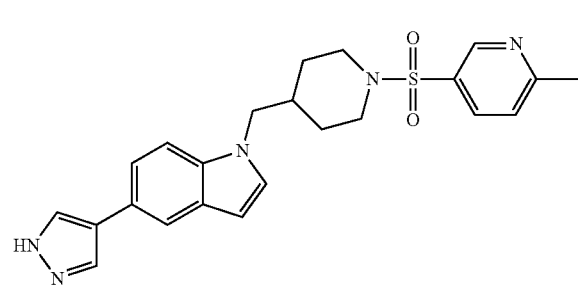

1-((1-((6-methylpyridin-3-yl)sulfonyl)piperidin-4-yl)methyl)-5-(1H-pyrazol-4-yl)-1H-indole

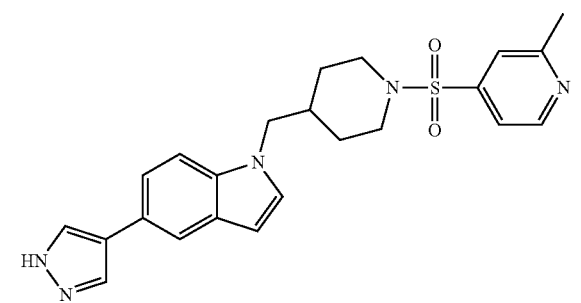

1-((1-((2-methylpyridin-4-yl)sulfonyl)piperidin-4-yl)methyl)-5-(1H-pyrazol-4-yl)-1H-indole

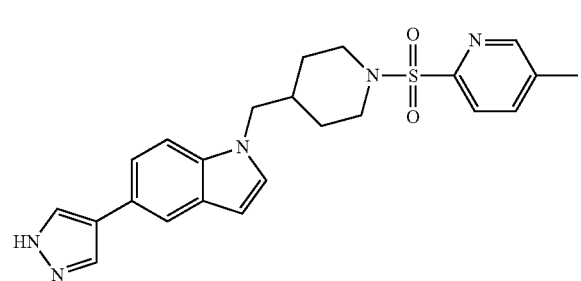

1-((1-((5-methylpyridin-2-yl)sulfonyl)piperidin-4-yl)methyl)-5-(1H-pyrazol-4-yl)-1H-indole -continued

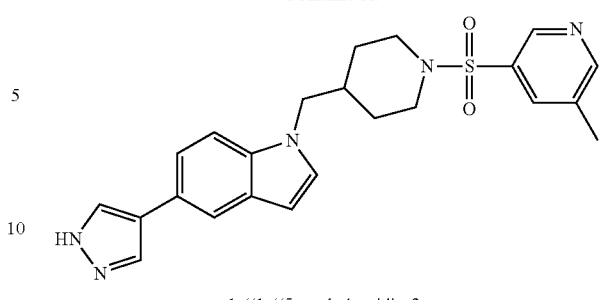

1-((1-((5-methylpyridin-3-yl)sulfonyl)piperidin-4-yl)methyl)-5-(1H-pyrazol-4-yl)-1H-indole

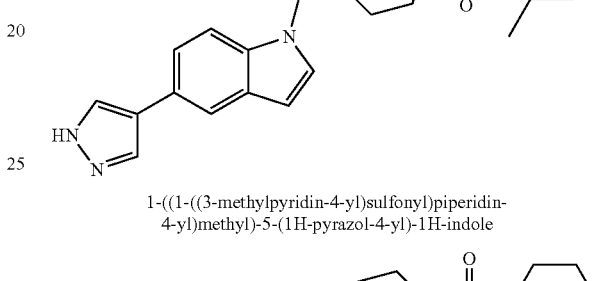

1-((1-((3-methylpyridin-4-yl)sulfonyl)piperidin-4-yl)methyl)-5-(1H-pyrazol-4-yl)-1H-indole

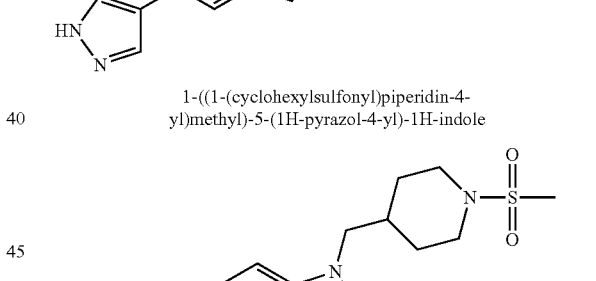

1-((1-(cyclohexylsulfonyl)piperidin-4-yl)methyl)-5-(1H-pyrazol-4-yl)-1H-indole

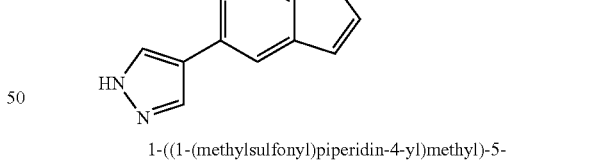

1-((1-(methylsulfonyl)piperidin-4-yl)methyl)-5-(1H-pyrazol-4-yl)-1H-indole

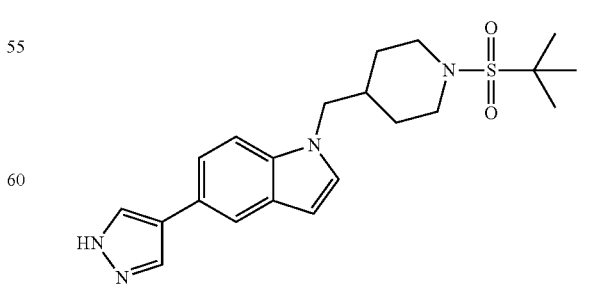

1-((1-(tert-butylsulfonyl)piperidin-4-yl)methyl)-5-(1H-pyrazol-4-yl)-1H-indole

-continued

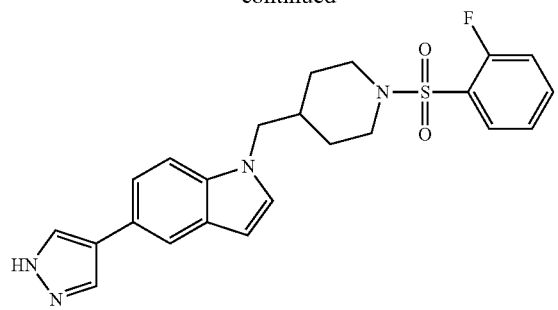

1-((1-((2-fluorophenyl)sulfonyl)piperidin-4-yl)methyl)-5-(1H-pyrazol-4-yl)-1H-indole

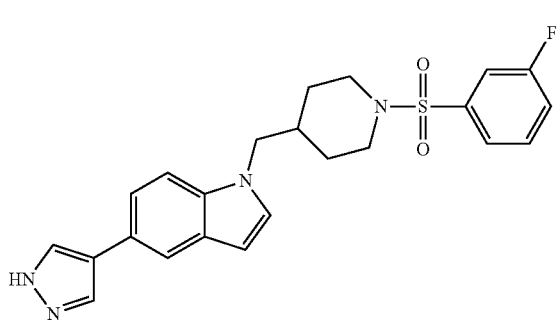

1-((1-((3-fluorophenyl)sulfonyl)piperidin-4-yl)methyl)-5-(1H-pyrazol-4-yl)-1H-indole

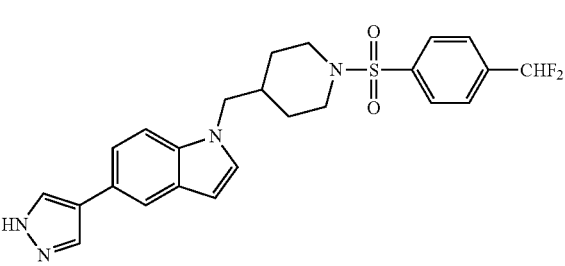

1-((1-((4-(difluoromethyl)phenyl)sulfonyl)piperidin-4-yl)methyl)-5-(1H-pyrazol-4-yl)-1H-indole

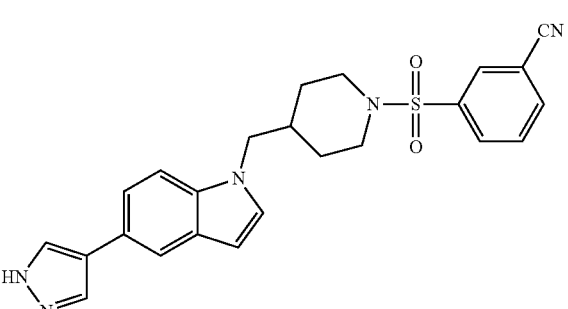
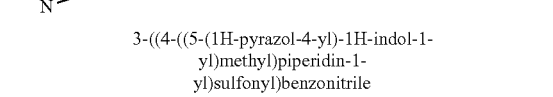

3-((4-((5-(1H-pyrazol-4-yl)-1H-indol-1-yl)methyl)piperidin-1-yl)sulfonyl)benzonitrile -continued

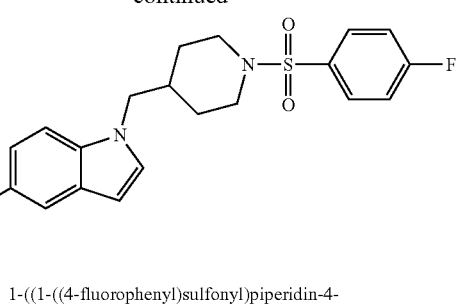

1-((1-((4-fluorophenyl)sulfonyl)piperidin-4-yl)methyl)-5-(1H-pyrazol-4-yl)-1H-indole

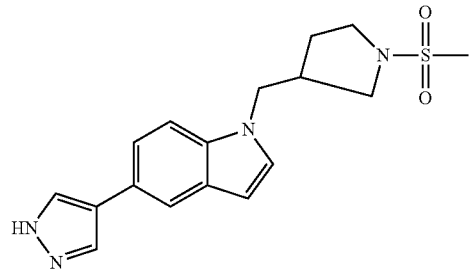

1-((1-(methylsulfonyl)pyrrolidin-3-yl)methyl)-5-(1H-pyrazol-4-yl)-1H-indole

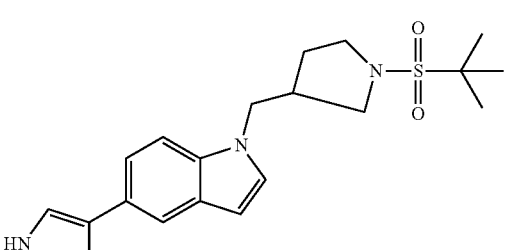

1-((1-(tert-butylsulfonyl)pyrrolidin-3-yl)methyl)-5-(1H-pyrazol-4-yl)-1H-indole

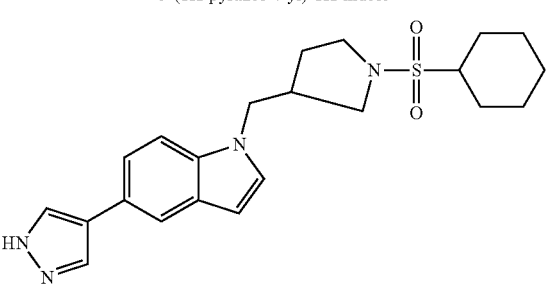

1-((1-(cyclohexylsulfonyl)pyrrolidin-3-yl)methyl)-5-(1H-pyrazol-4-yl)-1H-indole

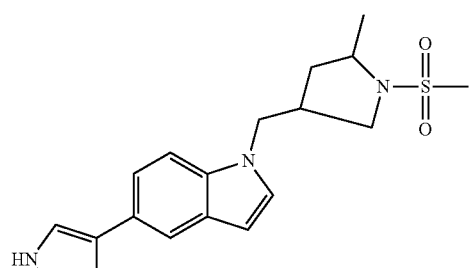

1-((5-methyl-1-(methylsulfonyl)pyrrolidin-3-yl)methyl)-5-(1H-pyrazol-4-yl)-1H-indole -continued

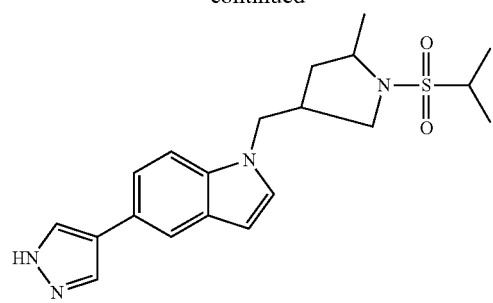

1-((1-(isopropylsulfonyl)-5-methylpyrrolidin-3-yl)methyl)-5-(1H-pyrazol-4-yl)-1H-indole

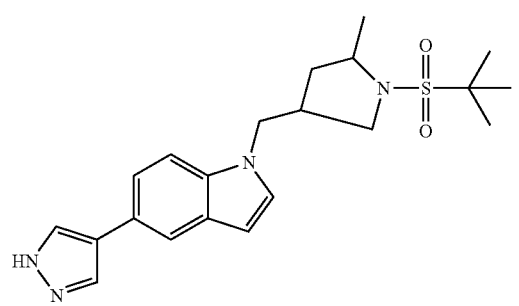

1-((1-(tert-butylsulfonyl)-5-methylpyrrolidin-3-yl)methyl)-5-(1H-pyrazol-4-yl)-1H-indole

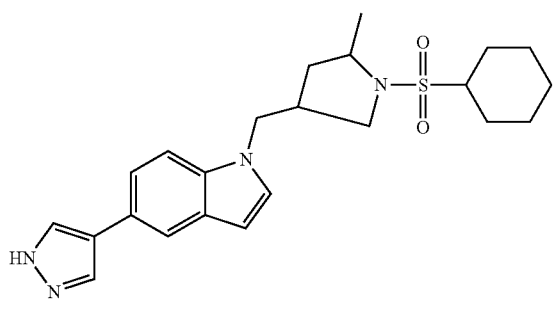

1-((1-(cyclohexylsulfonyl)-5-methylpyrrolidin-3-yl)methyl)-5-(1H-pyrazol-4-yl)-1H-indole

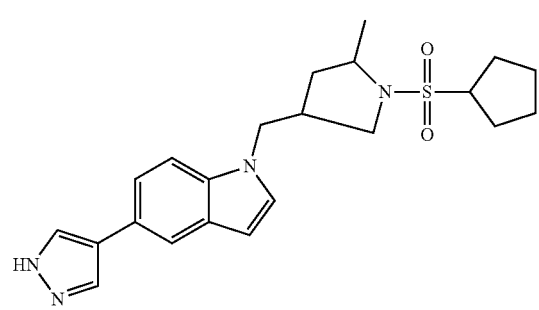

1-((1-(cyclopentylsulfonyl)-5-methylpyrrolidin-3-yl)methyl)-5-(1H-pyrazol-4-yl)-1H-indole -continued

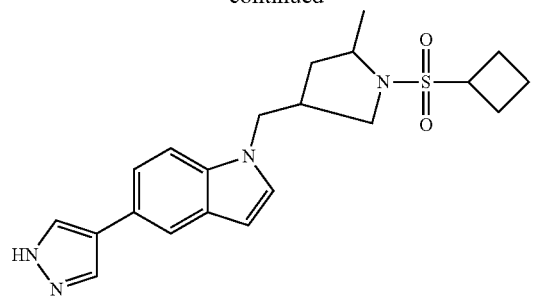

1-((1-(cyclobutylsulfonyl)-5-methylpyrrolidin-3-yl)methyl)-5-(1H-pyrazol-4-yl)-1H-indole

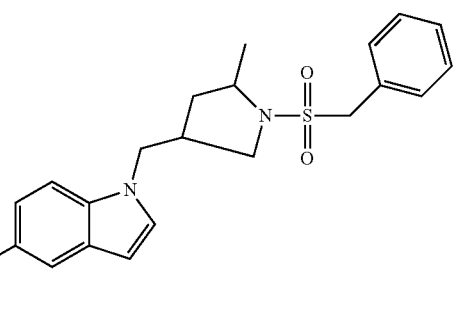

1-((1-(benzylsulfonyl)-5-methylpyrrolidin-3-yl)methyl)-5-(1H-pyrazol-4-yl)-1H-indole

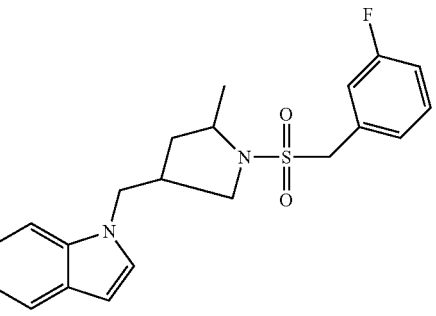

1-((1-((3-fluorobenzyl)sulfonyl)-5-methylpyrrolidin-3-yl)methyl)-5-(1H-pyrazol-4-yl)-1H-indole

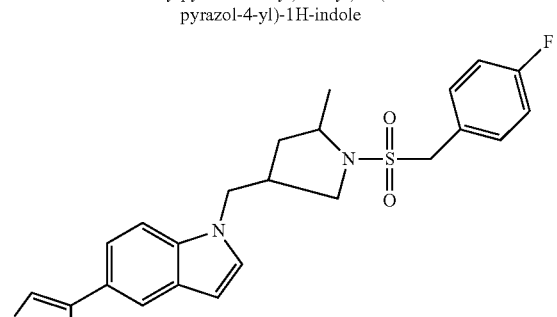

1-((1-((4-fluorobenzyl)sulfonyl)-5-methylpyrrolidin-3-yl)methyl)-5-(1H-pyrazol-4-yl)-1H-indole -continued

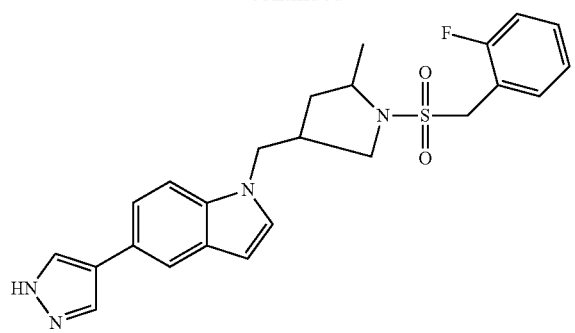

1-((1-((2-fluorobenzyl)sulfonyl)-5-methylpyrrolidin-3-yl)methyl)-5-(1H-pyrazol-4-yl)-1H-indole

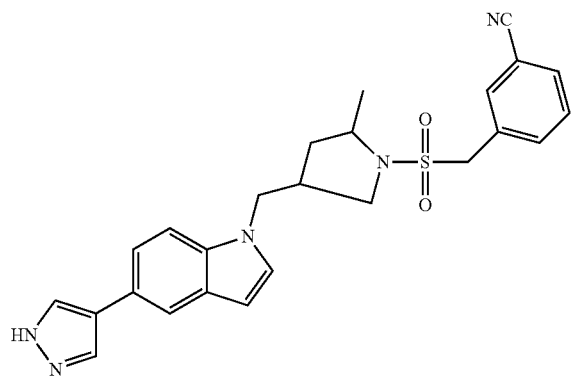

3-(((4-((5-(1H-pyrazol-4-yl)-1H-indol-1-yl)methyl)-2-methylpyrrolidin-1-yl)sulfonyl)methyl)benzonitrile

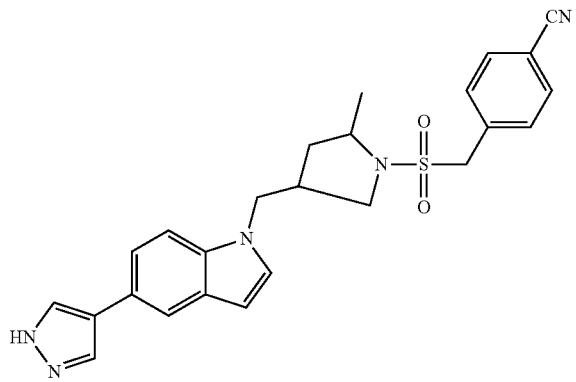

4-(((4-((5-(1H-pyrazol-4-yl)-1H-indol-1-yl)methyl)-2-methylpyrrolidin-1-yl)sulfonyl)methyl)benzonitrile

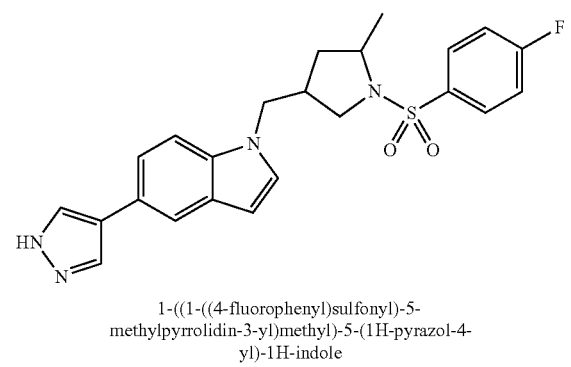

1-((1-((4-fluorophenyl)sulfonyl)-5-methylpyrrolidin-3-yl)methyl)-5-(1H-pyrazol-4-yl)-1H-indole -continued

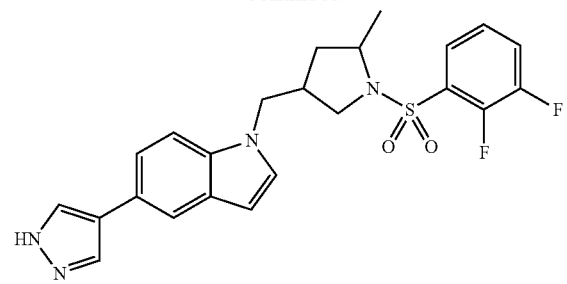

1-((1-((2,3-difluorophenyl)sulfonyl)-5-methylpyrrolidin-3-yl)methyl)-5-(1H-pyrazol-4-yl)-1H-indole

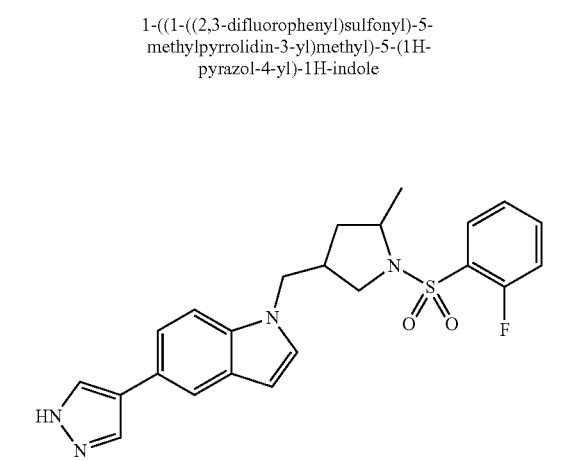

1-((1-((2-fluorophenyl)sulfonyl)-5-methylpyrrolidin-3-yl)methyl)-5-(1H-pyrazol-4-yl)-1H-indole

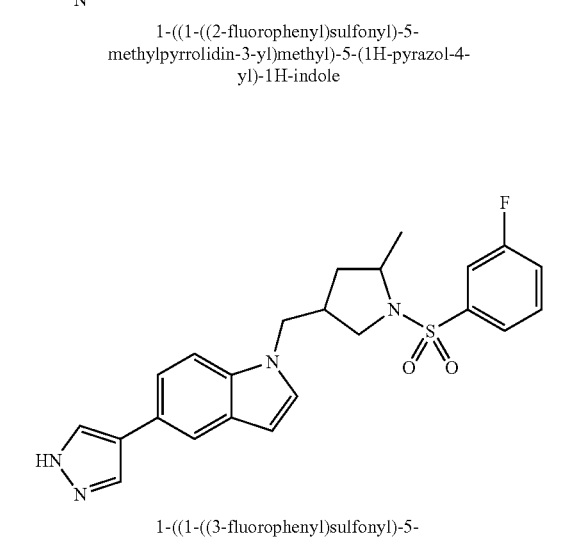

1-((1-((3-fluorophenyl)sulfonyl)-5-methylpyrrolidin-3-yl)methyl)-5-(1H-pyrazol-4-yl)-1H-indole

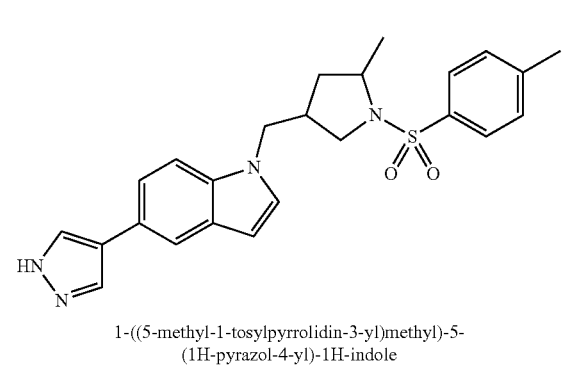

1-((5-methyl-1-tosylpyrrolidin-3-yl)methyl)-5-(1H-pyrazol-4-yl)-1H-indole

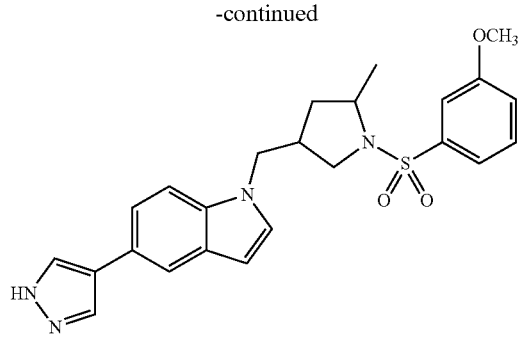

1-((1-((3-methoxyphenyl)sulfonyl)-5-
methylpyrrolidin-3-yl)methyl)-5-(1H-
pyrazol-4-yl)-1H-indole

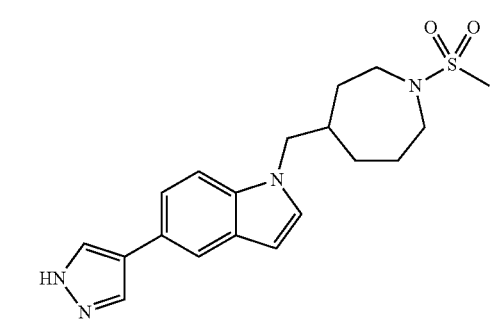

1-((1-(methylsulfonyl)azepan-4-yl)methyl)-5-
(1H-pyrazol-4-yl)-1H-indole

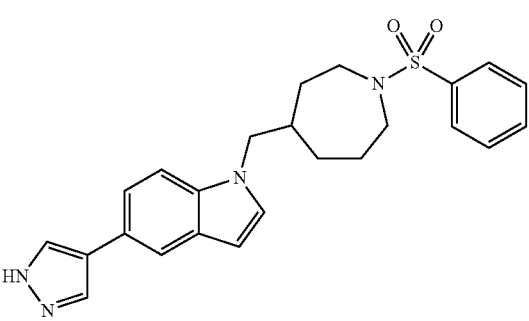

1-((1-(phenylsulfonyl)azepan-4-yl)methyl)-
5-(1H-pyrazol-4-yl)-1H-indole

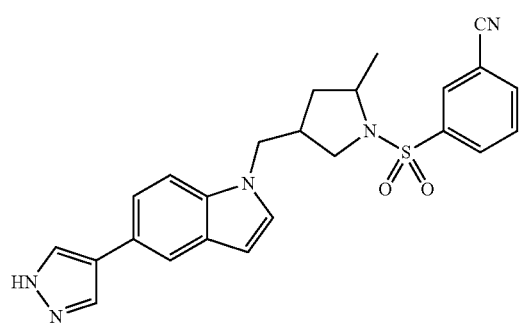

3-((4-((5-(1H-pyrazol-4-yl)-1H-indol-1-
yl)methyl)-2-methylpyrrolidin-1-
yl)sulfonyl)benzonitrile

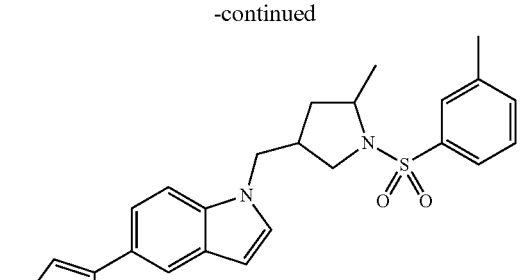

1-((5-methyl-1-(m-tolylsulfonyl)pyrrolidin-3-
yl)methyl)-5-(1H-pyrazol-4-yl)-1H-indole

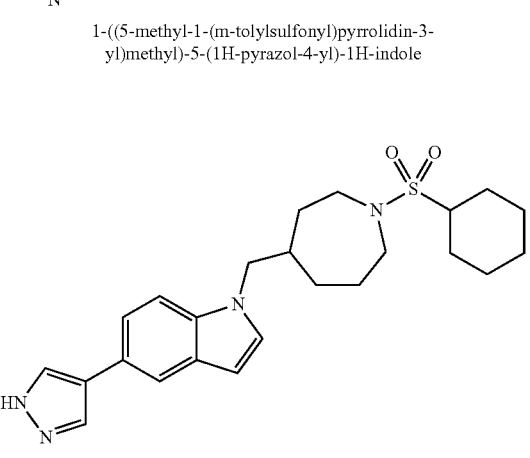

1-((1-(cyclohexylsulfonyl)azepan-4-yl)methyl)-
5-(1H-pyrazol-4-yl)-1H-indole

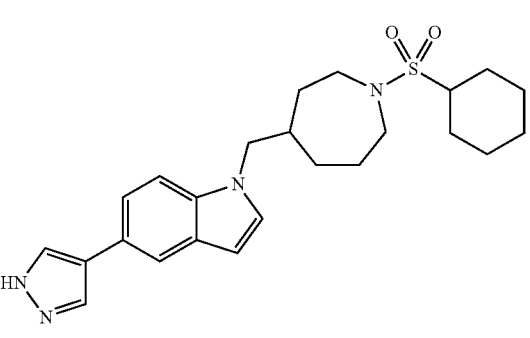

1-((1-(tert-butylsulfonyl)azepan-4-
yl)methyl)-5-(1H-pyrazol-4-yl)-1H-indole

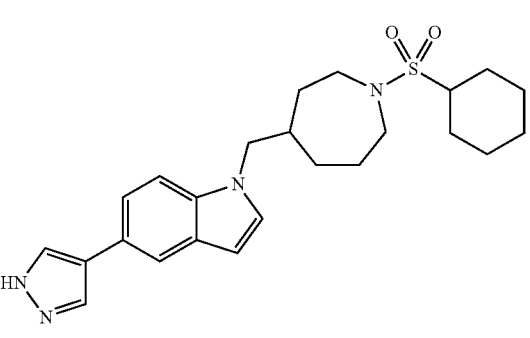

1-((1-((4-fluorophenyl)sulfonyl)azepan-4-
yl)methyl)-5-(1H-pyrazol-4-yl)-1H-indole -continued

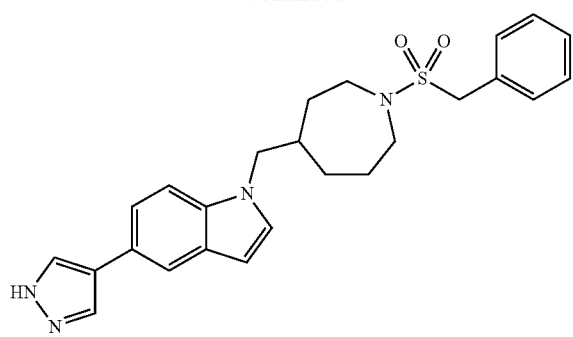

1-((1-(benzylsulfonyl)azepan-4-yl)methyl)-5-(1H-pyrazol-4-yl)-1H-indole

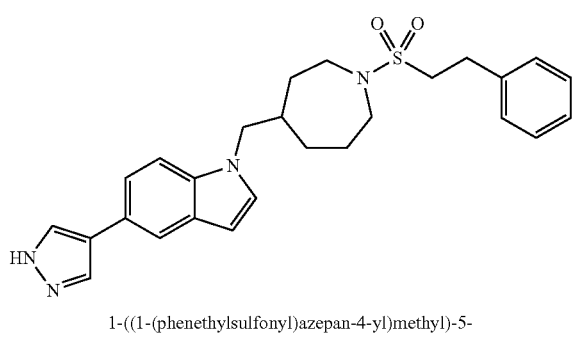

1-((1-(phenethylsulfonyl)azepan-4-yl)methyl)-5-(1H-pyrazol-4-yl)-1H-indole

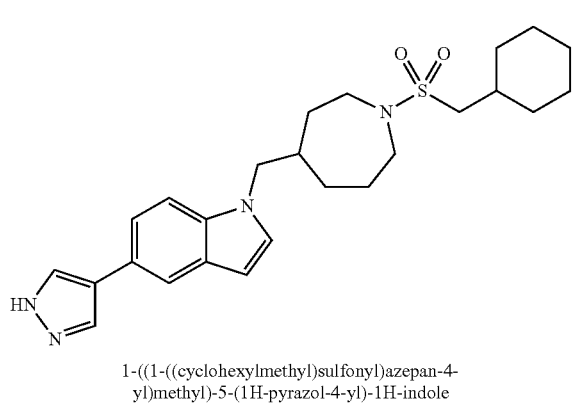

1-((1-((cyclohexylmethyl)sulfonyl)azepan-4-yl)methyl)-5-(1H-pyrazol-4-yl)-1H-indole

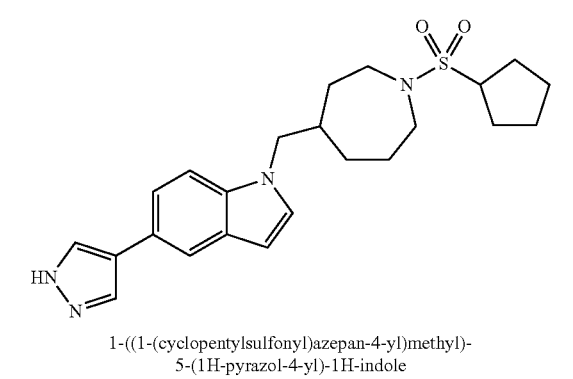

1-((1-(cyclopentylsulfonyl)azepan-4-yl)methyl)-5-(1H-pyrazol-4-yl)-1H-indole

-continued

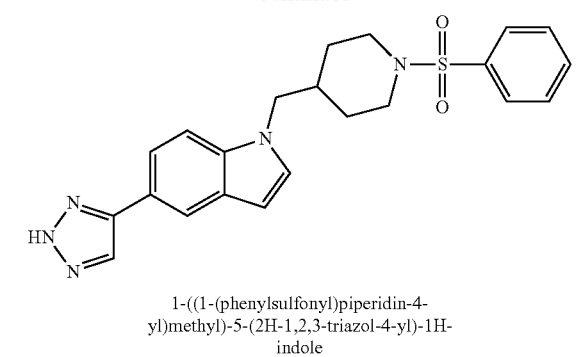

1-((1-(phenylsulfonyl)piperidin-4-yl)methyl)-5-(2H-1,2,3-triazol-4-yl)-1H-indole

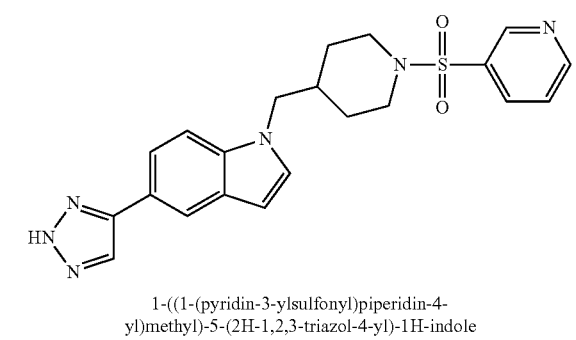

1-((1-(pyridin-3-ylsulfonyl)piperidin-4-yl)methyl)-5-(2H-1,2,3-triazol-4-yl)-1H-indole

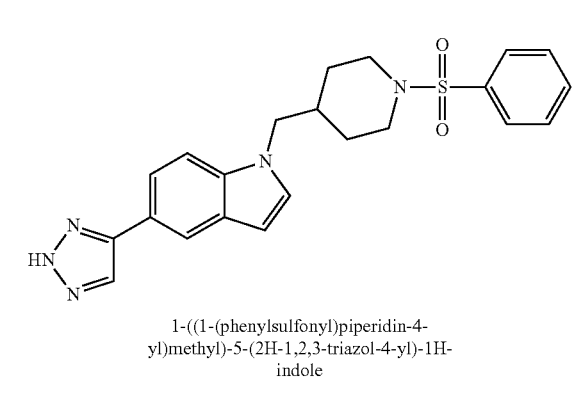

1-((1-(phenylsulfonyl)piperidin-4-yl)methyl)-5-(2H-1,2,3-triazol-4-yl)-1H-indole

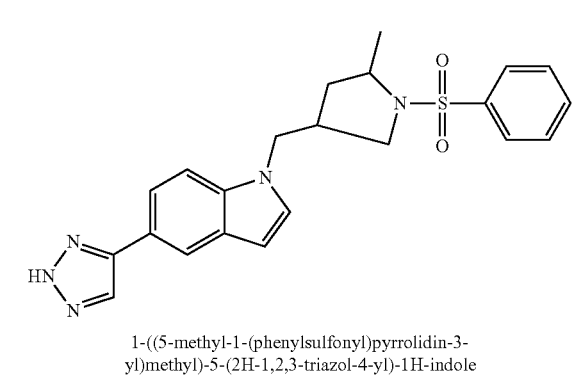

1-((5-methyl-1-(phenylsulfonyl)pyrrolidin-3-yl)methyl)-5-(2H-1,2,3-triazol-4-yl)-1H-indole -continued

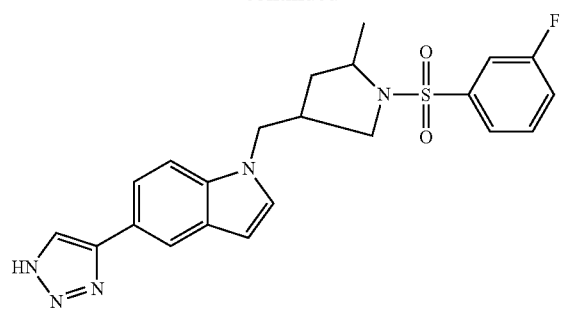

1-((1-((3-fluorophenyl)sulfonyl)-5-
methylpyrrolidin-3-yl)methyl)-5-(1H-1,2,3-
triazol-4-yl)-1H-indole

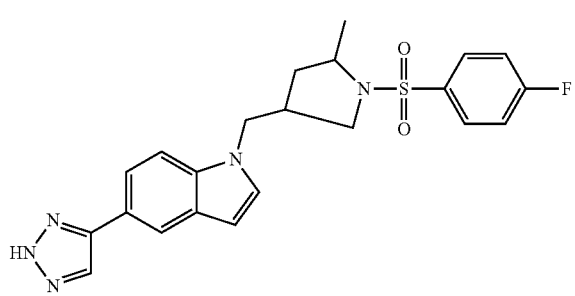

1-((1-((4-fluorophenyl)sulfonyl)-5-
methylpyrrolidin-3-yl)methyl)-5-(2H-1,2,3-
triazol-4-yl)-1H-indole

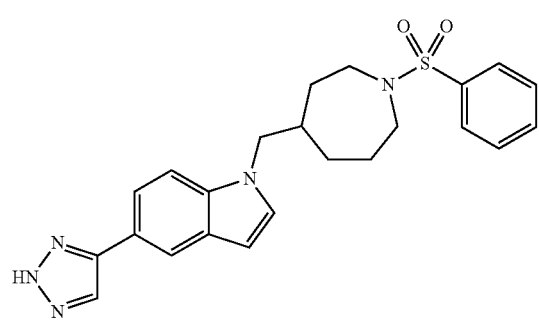

1-((1-(phenylsulfonyl)azepan-4-yl)methyl)-
5-(2H-1,2,3-triazol-4-yl)-1H-indole

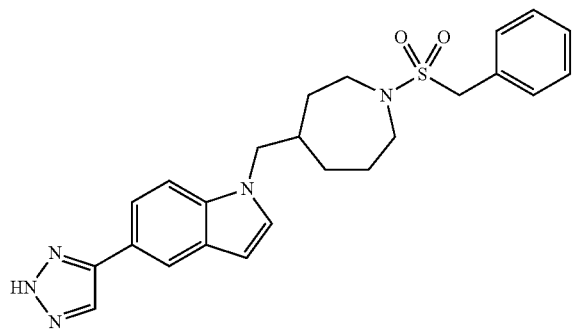

1-((1-(benzylsulfonyl)azepan-4-yl)methyl)-5-
(2H-1,2,3-triazol-4-yl)-1H-indole

-continued

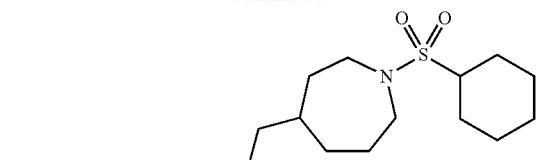

1-((1-(cyclohexylsulfonyl)azepan-4-
yl)methyl)-5-(2H-1,2,3-triazol-4-yl)-1H-
indole

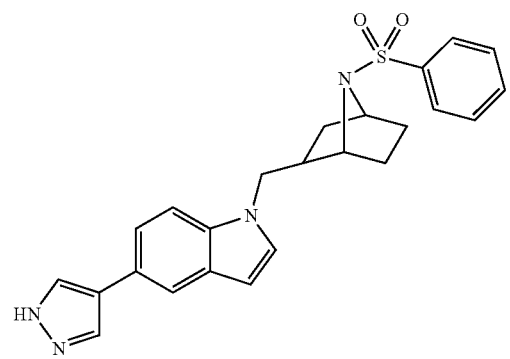

1-((7-(phenylsulfonyl)-7-
azabicyclo[2.2.1]heptan-2-yl)methyl)-5-(1H-
pyrazol-4-yl)-1H-indole

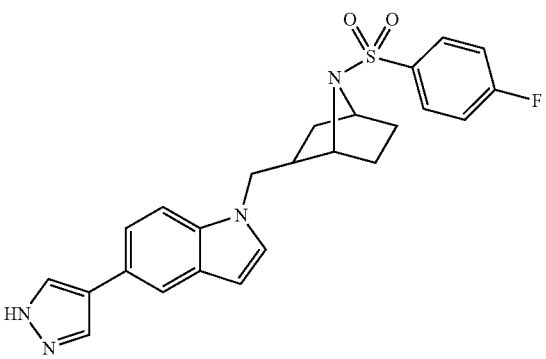

1-((7-((4-fluorophenyl)sulfonyl)-7-
azabicyclo[2.2.1]heptan-2-yl)methyl)-5-(1H-
pyrazol-4-yl)-1H-indole

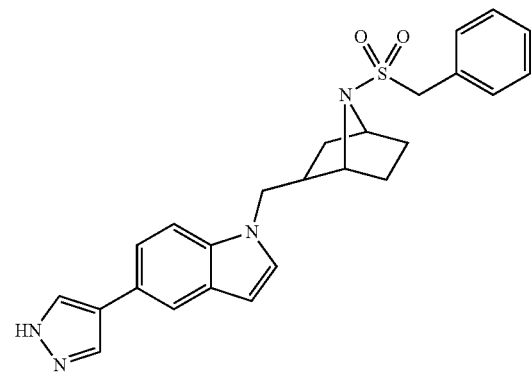

1-((7-(benzylsulfonyl)-7-
azabicyclo[2.2.1]heptan-2-yl)methyl)-5-(1H-
pyrazol-4-yl)-1H-indole

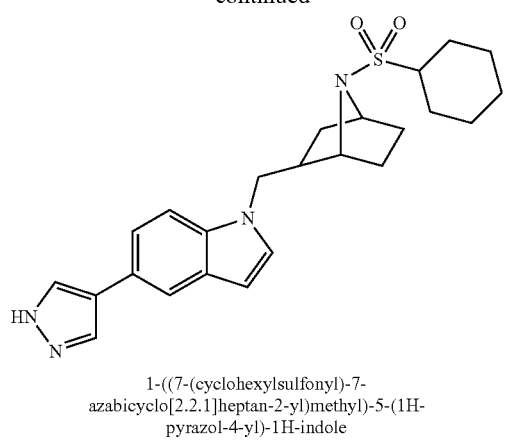

1-((7-(cyclohexylsulfonyl)-7-azabicyclo[2.2.1]heptan-2-yl)methyl)-5-(1H-pyrazol-4-yl)-1H-indole

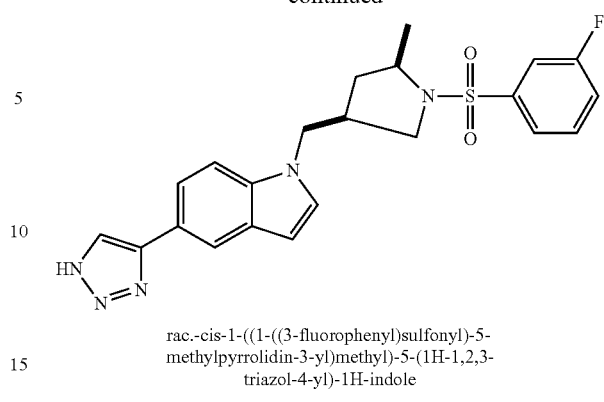

rac.-cis-1-((1-((3-fluorophenyl)sulfonyl)-5-methylpyrrolidin-3-yl)methyl)-5-(1H-1,2,3-triazol-4-yl)-1H-indole

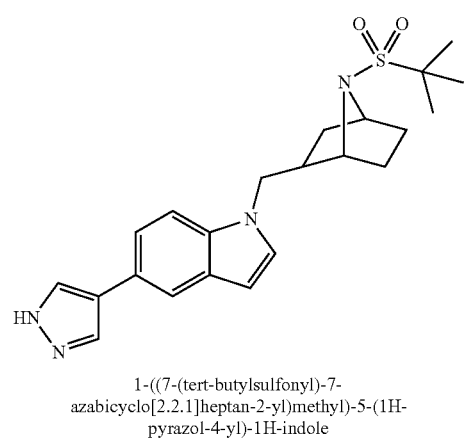

1-((7-(tert-butylsulfonyl)-7-azabicyclo[2.2.1]heptan-2-yl)methyl)-5-(1H-pyrazol-4-yl)-1H-indole

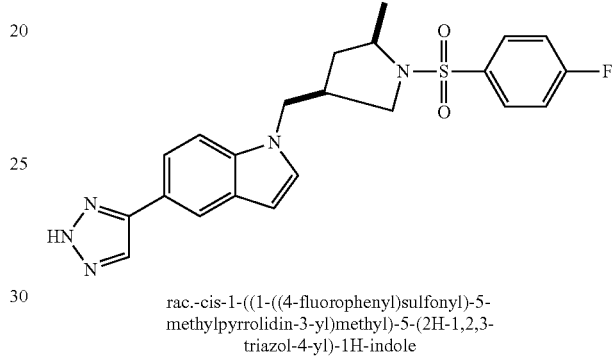

rac.-cis-1-((1-((4-fluorophenyl)sulfonyl)-5-methylpyrrolidin-3-yl)methyl)-5-(2H-1,2,3-triazol-4-yl)-1H-indole

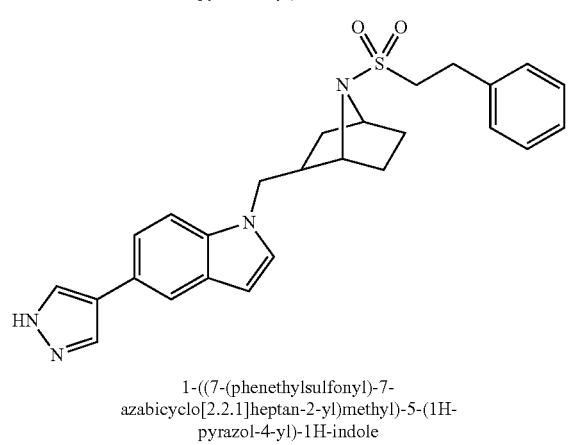

1-((7-(phenethylsulfonyl)-7-azabicyclo[2.2.1]heptan-2-yl)methyl)-5-(1H-pyrazol-4-yl)-1H-indole

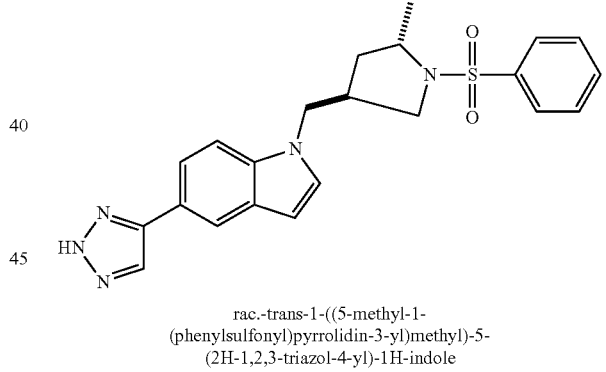

rac.-trans-1-((5-methyl-1-(phenylsulfonyl)pyrrolidin-3-yl)methyl)-5-(2H-1,2,3-triazol-4-yl)-1H-indole

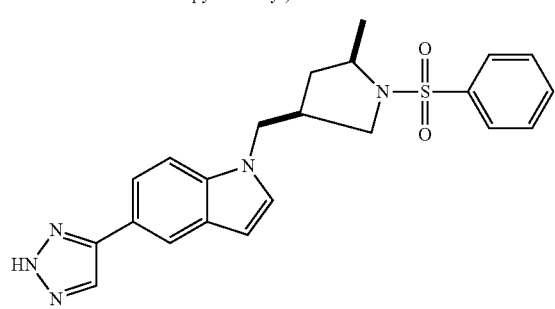

rac.-cis-1-((5-methyl-1-(phenylsulfonyl)pyrrolidin-3-yl)methyl)-5-(2H-1,2,3-triazol-4-yl)-1H-indole

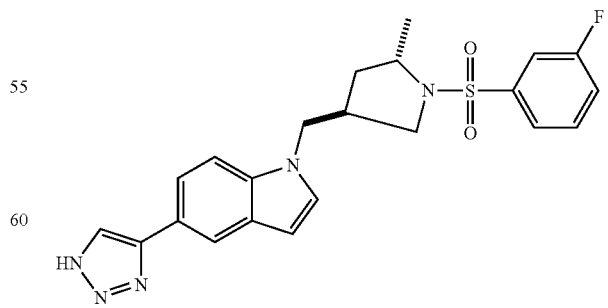

rac.-trans-1-((1-((3-fluorophenyl)sulfonyl)-5-methylpyrrolidin-3-yl)methyl)-5-(1H-1,2,3-triazol-4-yl)-1H-indole

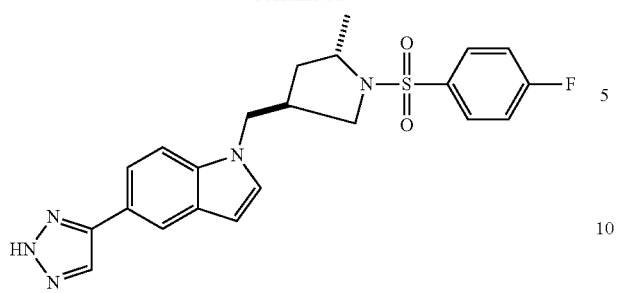

rac.-trans-1-((1-((4-fluorophenyl)sulfonyl)-
5-methylpyrrolidin-3-yl)methyl)-5-(2H-
1,2,3-triazol-4-yl)-1H-indole

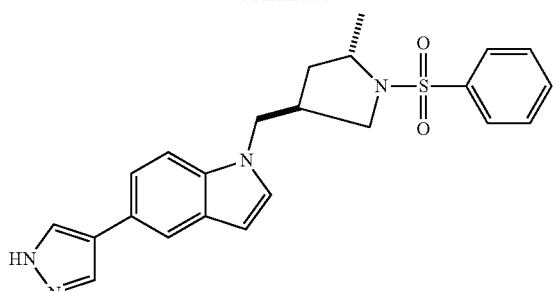

rac.-trans-1-((5-methyl-1-
(phenylsulfonyl)pyrrolidin-3-yl)methyl)-5-
(1H-pyrazol-4-yl)-1H-indole

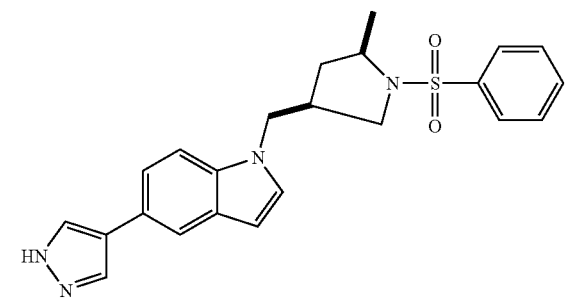

rac.-cis-1-((5-methyl-1-
(phenylsulfonyl)pyrrolidin-3-yl)methyl)-5-(1H-
pyrazol-4-yl)-1H-indole

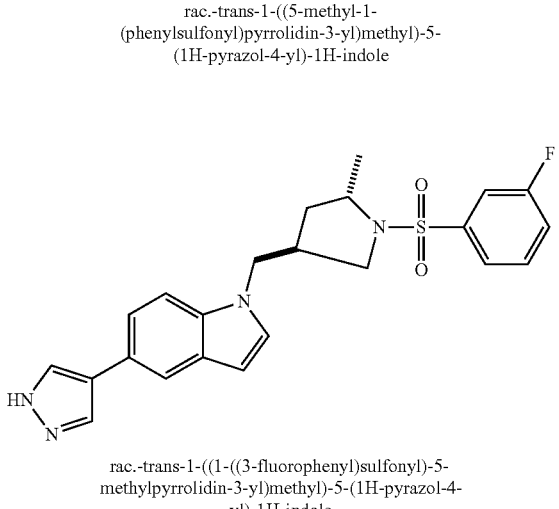

rac.-trans-1-((1-((3-fluorophenyl)sulfonyl)-5-
methylpyrrolidin-3-yl)methyl)-5-(1H-pyrazol-4-
yl)-1H-indole

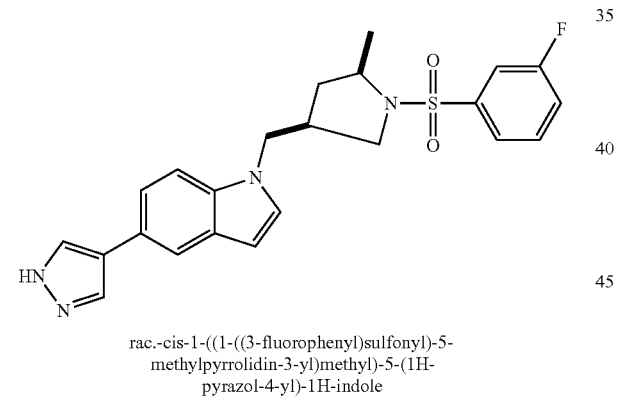

rac.-cis-1-((1-((3-fluorophenyl)sulfonyl)-5-
methylpyrrolidin-3-yl)methyl)-5-(1H-
pyrazol-4-yl)-1H-indole

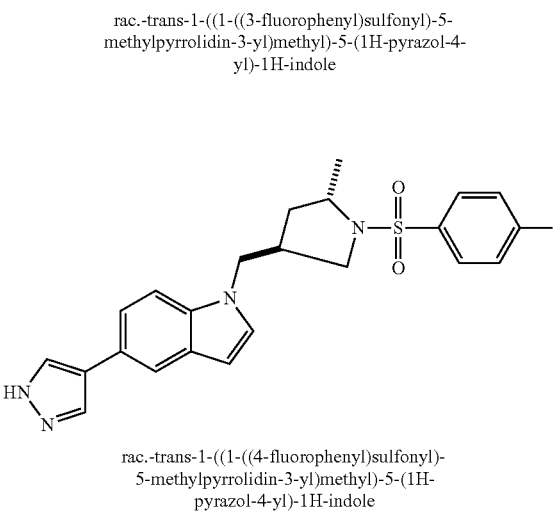

rac.-trans-1-((1-((4-fluorophenyl)sulfonyl)-
5-methylpyrrolidin-3-yl)methyl)-5-(1H-
pyrazol-4-yl)-1H-indole

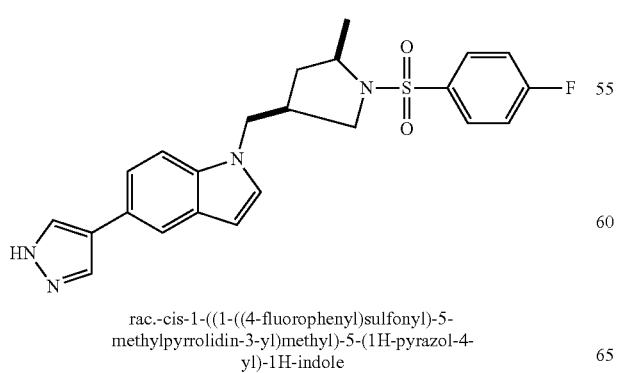

rac.-cis-1-((1-((4-fluorophenyl)sulfonyl)-5-
methylpyrrolidin-3-yl)methyl)-5-(1H-pyrazol-4-
yl)-1H-indole

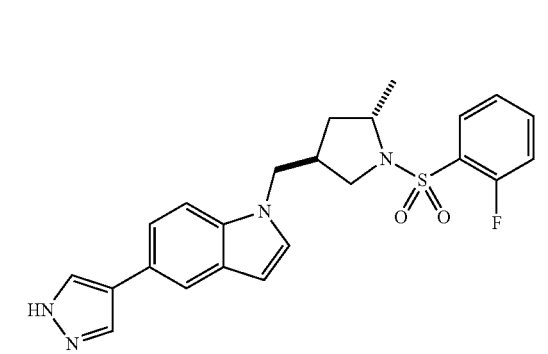

rac.-trans-1-((1-((2-fluorophenyl)sulfonyl)-5-
methylpyrrolidin-3-yl)methyl)-5-(1H-pyrazol-4-
yl)-1H-indole 33
-continued

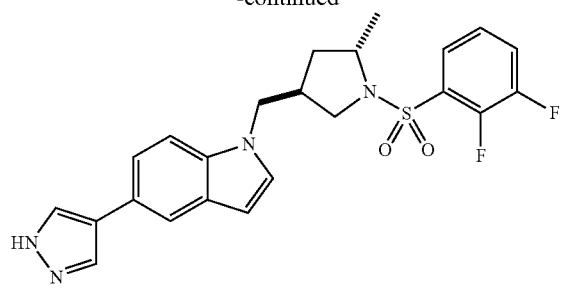

rac.-trans-1-((1-((2,3-
difluorophenyl)sulfonyl)-5-methylpyrrolidin-
3-yl)methyl)-5-(1H-pyrazol-4-yl)-1H-indole

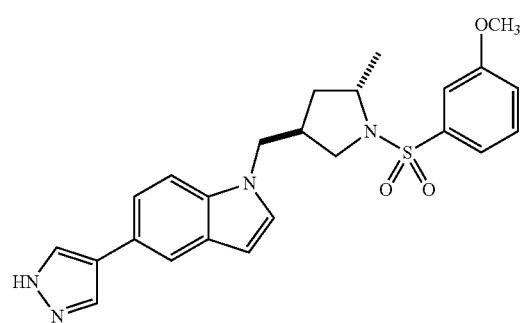

rac.-trans-1-((1-((3-methoxyphenyl)sulfonyl)-5-
methylpyrrolidin-3-yl)methyl)-5-(1H-pyrazol-4-
yl)-1H-indole

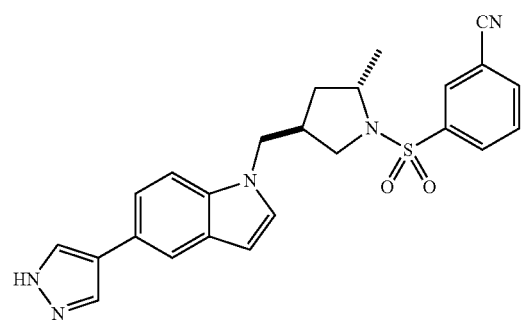

rac.-trans-3-((4-((5-(1H-pyrazol-4-yl)-1H-
indol-1-yl)methyl)-2-methylpyrrolidin-1-
yl)sulfonyl)benzonitrile

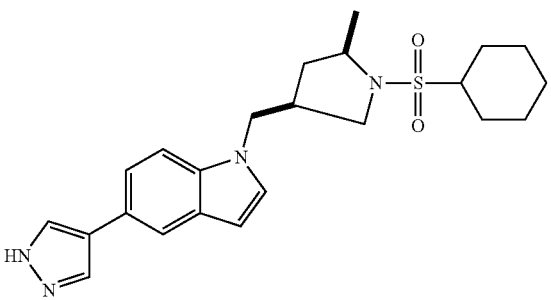

cis-trans-1-((1-(cyclohexylsulfonyl)-5-
methylpyrrolidin-3-yl)methyl)-5-(1H-pyrazol-4-
yl)-1H-indole 34
-continued

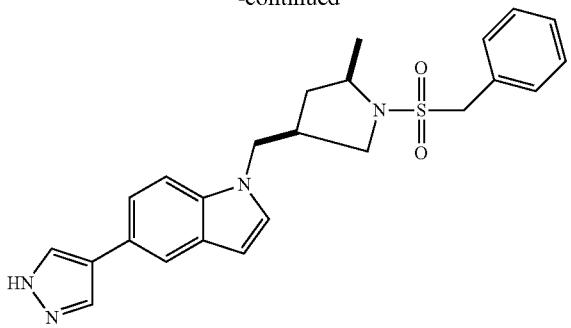

cis-trans-1-((1-(benzylsulfonyl)-5-
methylpyrrolidin-3-yl)methyl)-5-(1H-
pyrazol-4-yl)-1H-indole

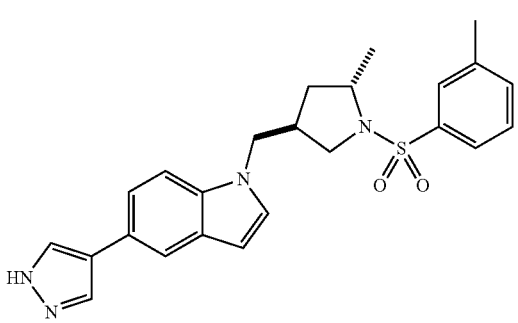

rac.-trans-1-(((3R,5S)-5-methyl-1-(m-
tolylsulfonyl)pyrrolidin-3-yl)methyl)-5-(1H-
pyrazol-4-yl)-1H-indole

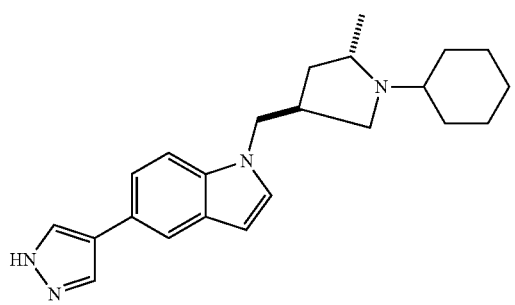

trans-trans-1-((1-cyclohexyl-5-
methylpyrrolidin-3-yl)methyl)-5-(1H-
pyrazol-4-yl)-1H-indole

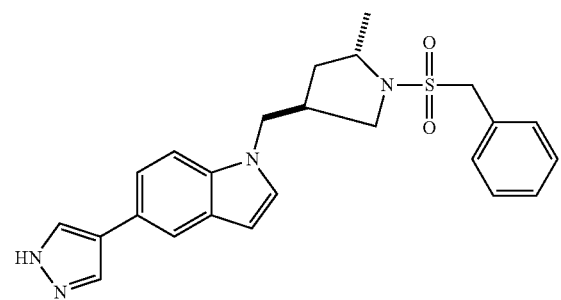

rac.-trans-1-((1-(benzylsulfonyl)-5-
methylpyrrolidin-3-yl)methyl)-5-(1H-pyrazol-4-
yl)-1H-indole -continued

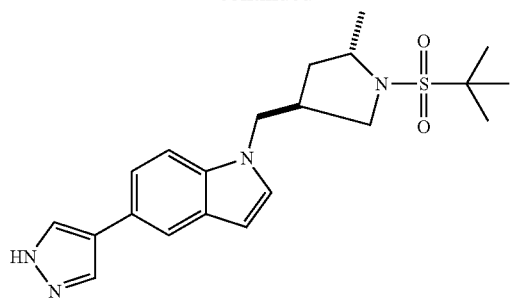

rac.-trans-1-((1-(tert-butylsulfonyl)-5-
methylpyrrolidin-3-yl)methyl)-5-(1H-
pyrazol-4-yl)-1H-indole

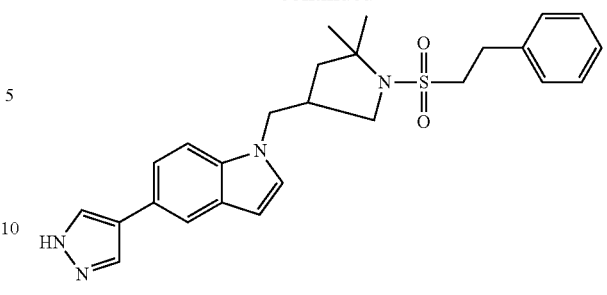

1-((5,5-dimethyl-1-
(phenethylsulfonyl)pyrrolidin-3-yl)methyl)-
5-(1H-pyrazol-4-yl)-1H-indole

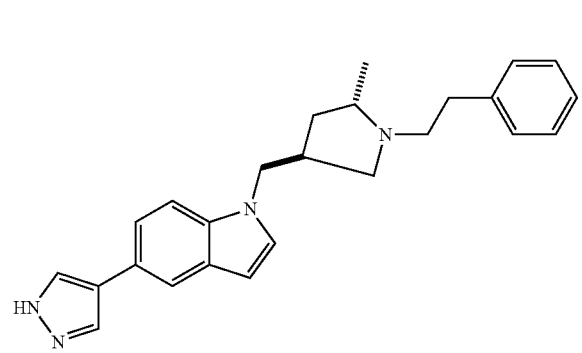

rac.-trans-1-((5-methyl-1-phenethylpyrrolidin-3-
yl)methyl)-5-(1H-pyrazol-4-yl)-1H-indole

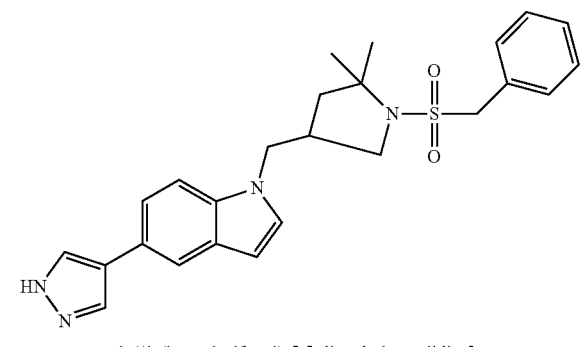

1-((1-(benzylsulfonyl)-5,5-dimethylpyrrolidin-3-
yl)methyl)-5-(1H-pyrazol-4-yl)-1H-indole

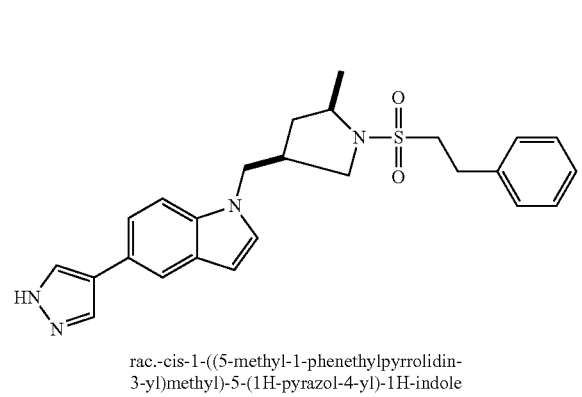

rac.-cis-1-((5-methyl-1-phenethylpyrrolidin-
3-yl)methyl)-5-(1H-pyrazol-4-yl)-1H-indole

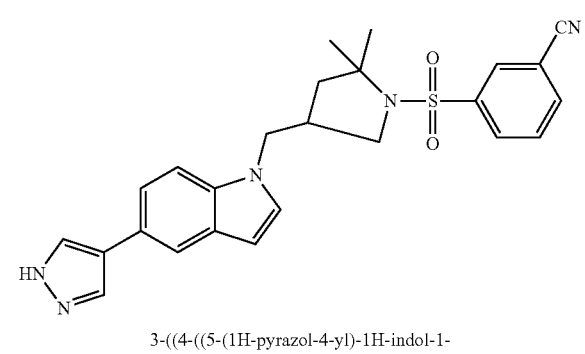

3-((4-((5-(1H-pyrazol-4-yl)-1H-indol-1-
yl)methyl)-2,2-dimethylpyrrolidin-1-
yl)sulfonyl)benzonitrile

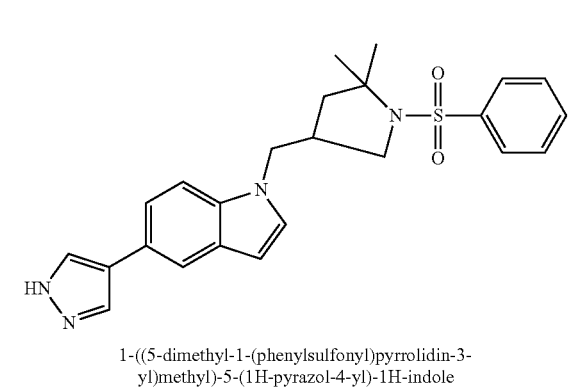

1-((5-dimethyl-1-(phenylsulfonyl)pyrrolidin-3-
yl)methyl)-5-(1H-pyrazol-4-yl)-1H-indole

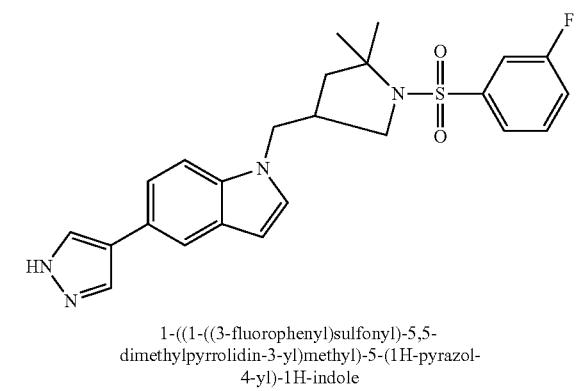

1-((1-((3-fluorophenyl)sulfonyl)-5,5-
dimethylpyrrolidin-3-yl)methyl)-5-(1H-pyrazol-
4-yl)-1H-indole 37
-continued

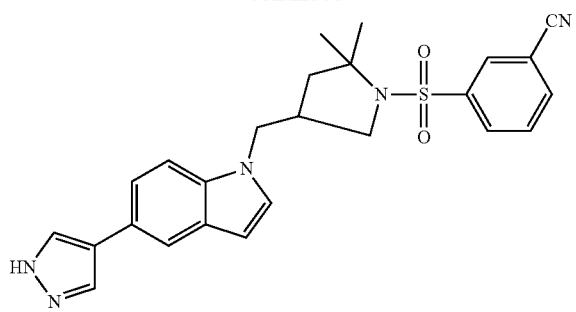

3-((4-((5-(1H-pyrazol-4-yl)-1H-indol-1-
yl)methyl)-2,2-dimethylpyrrolidin-1-
yl)sulfonyl)benzonitrile

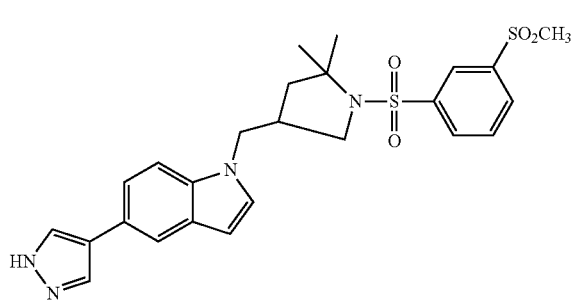

1-((5,5-dimethyl-1-((3-
(methylsulfonyl)phenyl)sulfonyl)pyrrolidin-3-
yl)methyl)-5-(1H-pyrazol-4-yl)-1H-indole

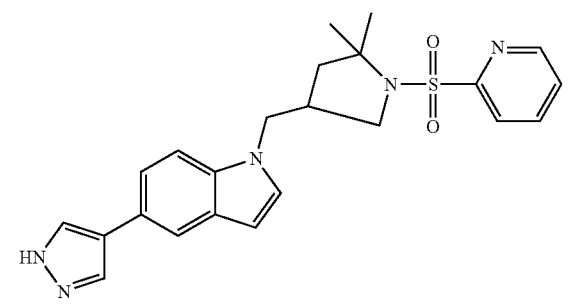

1-((5,5-dimethyl-1-(pyridin-2-
ylsulfonyl)pyrrolidin-3-yl)methyl)-5-(1H-
pyrazol-4-yl)-1H-indole

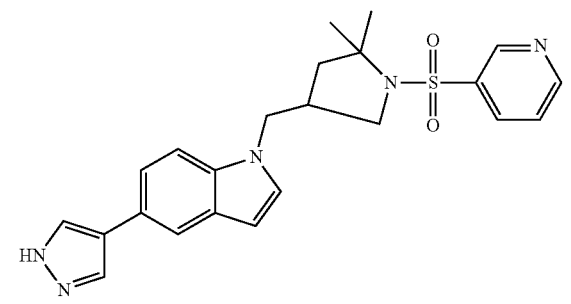

1-((5,5-dimethyl-1-(pyridin-3-
ylsulfonyl)pyrrolidin-3-yl)methyl)-5-(1H-
pyrazol-4-yl)-1H-indole 38
-continued

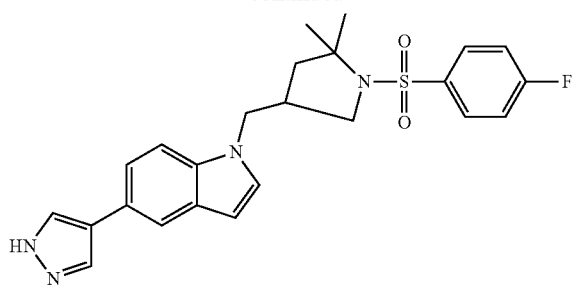

1-((1-((4-fluorophenyl)sulfonyl)-5,5-
dimethylpyrrolidin-3-yl)methyl)-5-(1H-
pyrazol-4-yl)-1H-indole

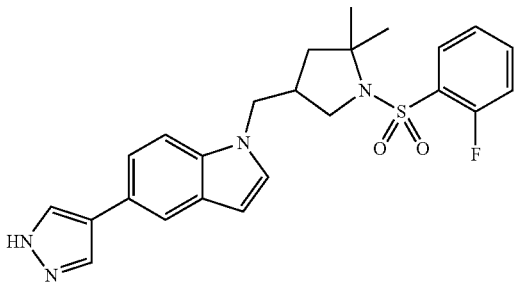

1-((1-((2-fluorophenyl)sulfonyl)-5,5-
dimethylpyrrolidin-3-yl)methyl)-5-(1H-pyrazol-
4-yl)-1H-indole

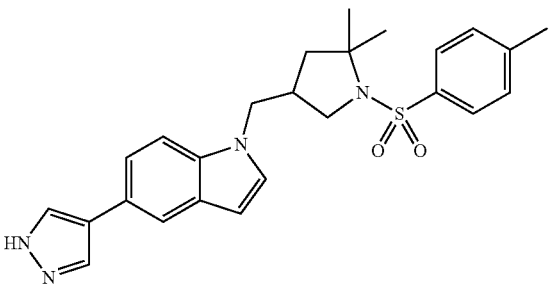

1-((1-((2,3-difluorophenyl)sulfonyl)-5,5-
dimethylpyrrolidin-3-yl)methyl)-5-(1H-
pyrazol-4-yl)-1H-indole 1-((5,5-dimethyl-1-tosylpyrrolidin-3-yl)methyl)-
5-(1H-pyrazol-4-yl)-1H-indole

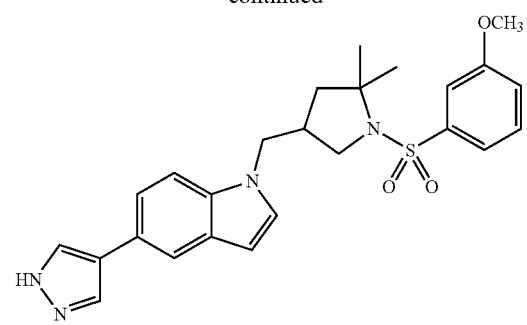

1-((1-((3-methoxyphenyl)sulfonyl)-5,5-
dimethylpyrrolidin-3-yl)methyl)-5-(1H-
pyrazol-4-yl)-1H-indole

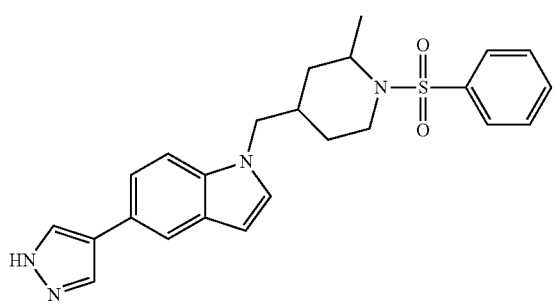

1-((2-methyl-1-(phenylsulfonyl)piperidin-4-
yl)methyl)-5-(1H-pyrazol-4-yl)-1H-indole

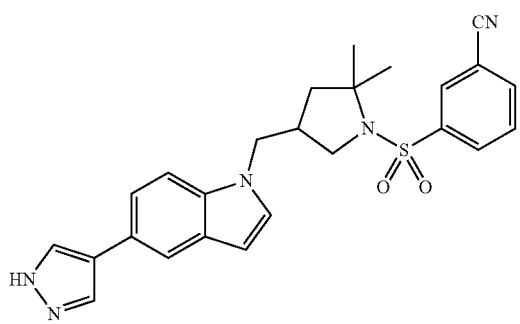

3-((4-((5-(1H-pyrazol-4-yl)-1H-indol-1-
yl)methyl)-2,2-dimethylpyrrolidin-1-
yl)sulfonyl)benzonitrile

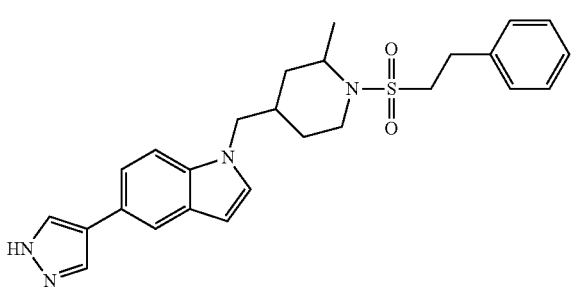

1-((2-methyl-1-(phenethylsulfonyl)piperidin-4-
yl)methyl)-5-(1H-pyrazol-4-yl)-1H-indole

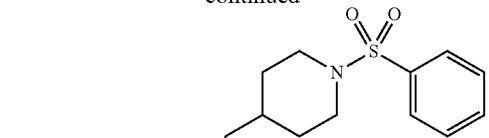

1-((1-(phenylsulfonyl)piperidin-4-
yl)methyl)-6-(1H-pyrazol-4-yl)-1,2,3,4-
tetrahydroquinoline

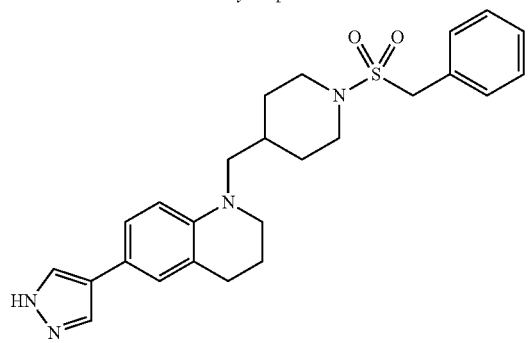

1-((1-(benzylsulfonyl)piperidin-4-yl)methyl)-6-
(1H-pyrazol-4-yl)-1,2,3,4-tetrahydroquinoline

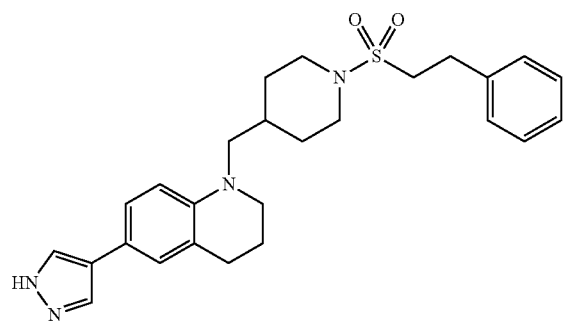

1-((1-(phenylsulfonyl)piperidin-4-
yl)methyl)-6-(1H-pyrazol-4-yl)-1,2,3,4-
tetrahydroquinoline

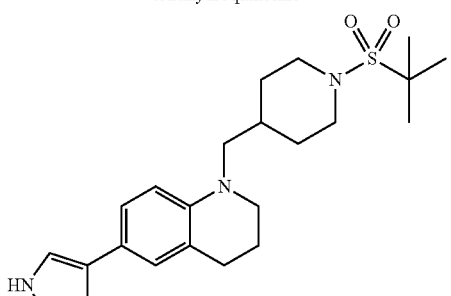

1-((1-(tert-butylsulfonyl)piperidin-4-yl)methyl)-
6-(1H-pyrazol-4-yl)-1,2,3,4-tetrahydroquinoline In another aspect, methods of inhibiting, preventing or treating a disease, or symptoms of a disease, regulated by RORα and/or RORγ, is provided, which comprises administering to a subject in need thereof, a therapeutically-effective amount of a ROR modulator. In some embodiments, the disease regulated by RORα and/or RORγ is selected from Autoimmune, Inflammatory, Metabolic and Oncologic Diseases, including but not limited to angina pectoris, myocardial infarction, atherosclerosis, cystic fibrosis, gastritis, autoimmune myositis, giant cell arteritis, Wegener's granulomatosis, asthma, chronic obstructive pulmonary disease, rheumatoid arthritis, juvenile rheumatoid arthritis, allergen-induced lung inflammation, allergy, psoriasis, psoriatic arthritis, colitis, inflammatory bowel disease, Crohn's disease, ulcerative colitis, Sjogren's syndrome, dry eye, optic neuritis, neuromyelitis optica, myasthenia gravis, Guillain-Barre syndrome, Graves disease, multiple sclerosis, autoimmune uveitis, ankylosing spondylitis, organ transplant rejection, polymyalgia rheumatic, systemic lupus erythematosus, cutaneous lupus, lupus nephritis, glomerulonephritis, diabetes mellitus type 1, pulmonary inflammation, macular degeneration, obesity, nonalcoholic fatty liver disease, steatohepatitis, insulin resistance, diabetes mellitus type 2, glucose intolerance, and metabolic syndrome; and primary and metastatic Oncologic Diseases, including but not limited to multiple myeloma, bone disease associated with multiple myeloma, lymphoma, melanoma, sarcoma, colorectal cancer, esophageal cancer, and cancers of the bladder, brain, breast, cervix, ovaries, head and neck, kidney, liver, lung, prostate and pancreas.

Also described are methods of modulating RORα and/or RORγ activity as an agonist, inverse agonist or antagonist/non-agonist in a subject, which comprises administering to a subject in need thereof a pharmaceutically effective amount of a ROR modulator.

Also described are methods of inducing or inhibiting RORα- and/or RORγ-regulated target gene expression and protein production in a subject which comprises administering to a subject in need thereof a pharmaceutically effective amount of a ROR modulator.

Also described are methods of regulating corepressor and/or coactivator protein interaction with RORα and/or RORγ LBD in a subject that comprises administering to a subject in need thereof a pharmaceutically effective amount of a ROR modulator.

Also described are methods of decreasing or increasing the amount of RORα- and/or RORγ-regulated production of $T_H17$ cytokines IL-17A, IL-17F, IL-17AF, IL-21, and/or IL-22 in a subject which comprises administering to a subject in need thereof a pharmaceutically effective amount of a ROR modulator.

Also described are methods of inducing or inhibiting, either directly or indirectly, RORα- and/or RORγ-regulated cell proliferation or activation in a subject which comprises administering to a subject in need thereof a pharmaceutically effective amount of a ROR modulator.

The ROR modulators can each be administered in amounts that are sufficient to treat or prevent but are not limited to Autoimmune, Inflammatory, Metabolic and Oncologic Diseases, or prevent the development thereof in subjects.

The invention also includes pharmaceutical compositions useful for treating or preventing a ROR regulated disease, or for inhibiting a ROR regulated disease, or more than one of these activities. The compositions can be suitable for internal use and comprise an effective amount of a ROR modulator and a pharmaceutically acceptable carrier. The ROR modulators are especially useful in that they demonstrate very low systemic toxicity or no systemic toxicity.

Administration of the ROR modulators can be accomplished via any mode of administration for therapeutic agents. These modes include systemic or local administration such as oral, nasal, parenteral (intravenous), intramuscular, intrathecal, intra-vitreal, transdermal, subcutaneous, vaginal, buccal, rectal, topical administration modes or as a drug-eluting stent.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, intra-vitreal injection, subcutaneous or intramuscular form, all using forms well known to those skilled in the pharmaceutical arts.

Illustrative pharmaceutical compositions are tablets and gelatin capsules comprising a ROR modulator and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the ROR modulator is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the ROR modulators.

The ROR modulators can be also formulated as a suppository that can be prepared from fatty emulsions or suspensions; using polyalkylene glycols such as propylene glycol, as the carrier.

In further embodiments, the pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, delayed release formulations, extended release formulations, pulsatile release formulations, multiparticulate formulations, and mixed immediate and controlled release formulations The ROR modulators can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

ROR modulators can also be delivered by the use of monoclonal antibodies as individual carriers to which the ROR modulators are coupled. The ROR modulators can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the ROR modulators can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, ROR modulators are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the ROR modulator by weight or volume.

The dosage regimen utilizing the ROR modulator is selected in accordance with a variety of factors including type, species, age, weight, sex, race, diet, and medical condition of the patient; the severity of the condition to be treated; the route of administration; the renal or hepatic function of the patient; and the particular ROR modulator employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 0.1 mg to about 5000 mg of the active ingredient per unit dose which could be administered. In one embodiment, the compositions are in the form of a tablet that can be scored. Appropriate dosages of the ROR modulators can be determined as set forth in Goodman, L. S.; Gilman, A. The Pharmacological Basis of Therapeutics, 5th ed.; MacMillan: New York, 1975, pp. 201-226, the contents of which are hereby incorporated by reference.

ROR modulators can be administered in a single daily dose, or the total daily dosage can be administered in divided doses of two, three or four times daily. Furthermore, ROR modulators can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the ROR modulator ranges from about 0.1% to about 15%, w/w or w/v.

The ROR modulators can also each be administered in amounts that are sufficient to treat or prevent ROR-associated diseases. These diseases include, but are not limited to, Autoimmune, Inflammatory, Metabolic and Oncologic diseases, either individually or in combination with one or more agents and or methods for treating and preventing these ROR-regulated diseases.

General Schemes

Certain Methods for Making the RORα, RORγ and RORα/RORγ Modulators

Compounds of the present invention can be prepared beginning with commercially available starting materials and utilizing general synthetic techniques and procedures known to those skilled in the art. Chemicals may be purchased from companies such as for example SigmaAldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Mettler Toledo Instrument Newark, Del. Biotage, ISCO and Analogix columns are pre-packed silica gel columns used in standard chromatography.

Examples of synthetic pathways useful for making ROR modulators of the present invention are set forth in the Examples below and generalized in Schemes 1-5 below.

Scheme 1.

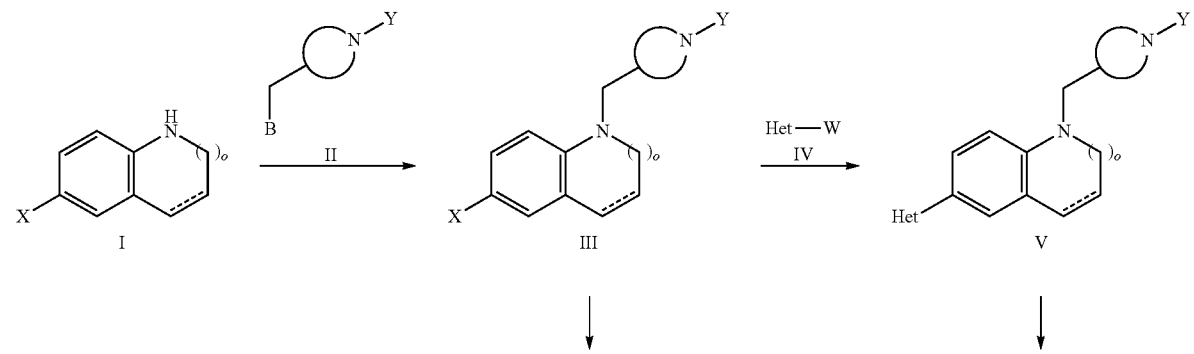

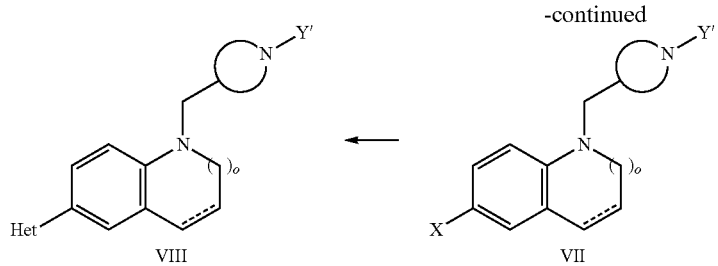
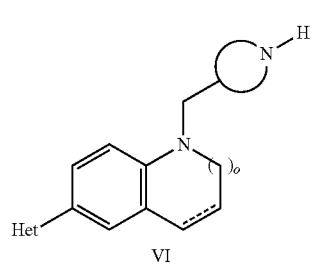

The starting materials I shown in scheme 1 wherein o is 1 or 0, ⋯ is a single bond when o is 1 or single or a double bond when o is 0, and X is a group capable of participating in a transition metal catalyzed cross coupling reaction, such as a chloride, bromide, iodide or triflate, are commercially available or readily prepared from commercially available compounds. Alkylation of I on nitrogen with a compound II in which B is a leaving group such as a bromide, chloride or tosylate and Y is either a protecting group, a substituted sulfonyl group of the invention or a substituted sulfonyl group which can be transformed into a substituted sulfonyl group, of the invention, to give a compound III can be accomplished by standard methods, such as treatment of a solution of compound I in suitable inert solvent such as DMF with base such as NaH followed by compound II. The reaction may be carried out at room temperature, or at a mildly elevated temperature. Alternatively, a compound II in which B represents an aldehyde may be condensed with the heterocycle I in the presence of a suitable reducing agent, for example sodium triacetoxyborohydride to give a compound III.

The resulting III may then be coupled to the heteroaromatic derivatives Het-W (IV) in which Het is an optionally substituted 5-7-membered heteroaromatic compound, which may incorporate a protecting group as appropriate, and W is a functional group such as a boronic acid or a halogen atom, capable of participating in a transition metal catalyzed cross-coupling reaction such as a Suzuki reaction. Skilled organic chemists will understand how to select the particular choice of X, W and transition metal catalyst for a given desired transformation and incorporate the appropriate protection/deprotection methods, where needed. In some cases, it may be desirable to convert X to a metal derivative prior to coupling. For example, see Stadlwieser, J. F., et al, *Helvetica Chimica ACTA* 2006, 89, 936-946. This is typically done using a bisborane such as bis(pinacolato)diboron in the presence of a suitable catalyst such as $PdCl_2(dppf)$-DCM to give a boronic acid derivative prior to the coupling reaction with Het-W. See for example: N. Kudo et al., *Angew. Chem. Int. Ed.,* 2006, 45, 1282-1284 and Dvorak, C. A.; et al., *Journal of Organic Chemistry* 2005, 70, 4188-4190; Barder, T. E., et al. *J. Am. Chem. Soc.* 2005, 127, 4685-4696, Isley, N. W. et al, *Journal of the American Chemical Society,* 2013, 135, 17707-17710. In some cases, other metalling reagents leading for example to organostannane or organozinc intermediates may be preferable for a particular desired coupling reaction. For a recent review on the implementation of organo zinc mediated coupling reactions, see Sidduri, A., et al., *Synthesis* 2014, 46, 430-444.

Carrying out the coupling reaction will then lead to the target compounds V, which depending on the selection of Y, may be compounds of the invention or intermediates that can be converted to compounds of the invention. For example, in cases where Y is a substituted sulfonyl group of the invention or a protected variant of such, removal of any protecting groups will lead directly to compounds of the invention. In cases where Y is a protecting group, for example a benzyl, carboxybenzyl or Boc group, removal using the appropriate conditions, well known to medicinal chemists, would lead to VI, which can be transformed to a compound of the invention via sulfonylation, followed by any needed functional group or protecting group manipulation. Sulfonylation reactions are most conveniently carried out by treatment of secondary amines such as VI with a sulfonyl chloride in the presence of a base, for example triethylamine in a suitable inert solvent, for example, dichoromethane.

In some cases, it may be desireable to manipulate the group Y in structure III to give VII in which Y' is a substituted sulfonyl group of the invention or may be simply transformed into a substituted sulfonyl group of the invention by routine transformations, prior to coupling the heterocyclic ring give VIII.

Scheme 2.

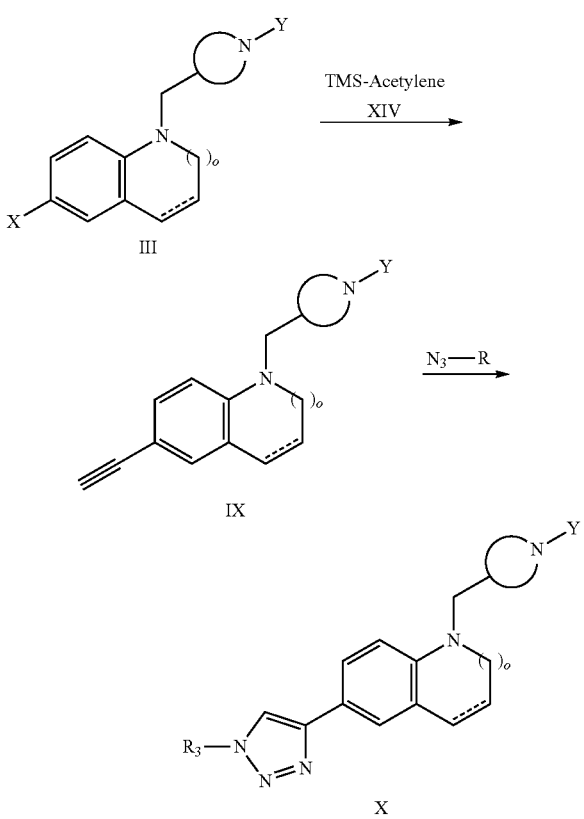

Alternatively, heterocycles Het in the above structures may be constructed directly attached to the indole, indoline or quinoline rings. Such transformations are well known in heterocyclic chemistry and skilled medicinal chemists will understand how to vary the order of the steps to suit the particular choice of target structure. For example, as shown in Scheme 2, 1,2,3-triazoles may be ready constructed by first converting a compound of structure III to an acetylene for example by treatment with TMS-acetylene in the presence of a suitable transition metal catalyst. Typically the TMS group is lost during workup and when it is still present, it can be removed under standard condition to give a compound of structure IX. Treatment of IX with a substituted azide derivative in the presence of a suitable catalyst, for example, a copper catalyst then gives the corresponding trazole of formula X which is either a compound of the invention or readily converted to a compound of the invention following suitable functional group transformations. Triazole formation using this method is widely used in organic chemistry and is typically referred to as "click chemistry". One variant is described in, Tornøe, C. W., et al, *J. Org Chem*, 2002, 67, 3057-3064. The application of click chemistry to the synthesis of certain electron deficient triazoles is described in Chattopadhysy, B., *Organic Letters* 2010, 12, 2166-2169. Depending on the choice of $R_3$, further functionalization of this substituent can be carried out after triazole formation using standard methods.

Alternative sequences are also envisioned, in which X of III is a nitrile or can be converted to a nitrile. Subsequent reactions leading to 1,2,4-triazoles, oxadiazoles and tetrazoles can be carried followed established literature precedent.

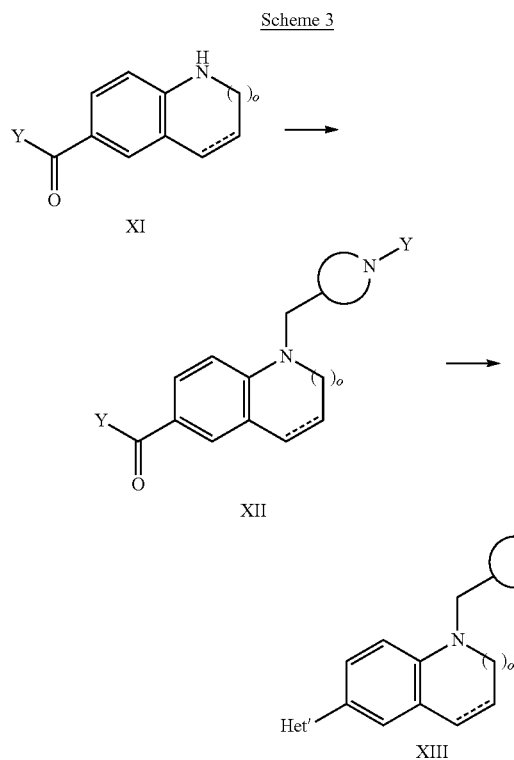

Scheme 3

XI

XII

XIII

As shown in scheme 3, in some cases it may be desireable to construct the heteroaromatic species from a carbonyl derivative such as XI, Y═H, OH, $NHR_4$, or $OR_5$, wherein $R_4$ is H, lower alkyl or $OR_6$, wherein $R_6$ is H or lower alkyl and $R_5$ is lower alkyl or another substituent suitable for the displacement chemistry associated with the intended heterocycle construction. Such intermediates can be alkylated as above with the appropriate reagents of structure II to give compounds of structure XII as described in Scheme 1, followed by elaboration of the carbonyl derivative to the desired heterocyclic derivatives, XIII using the chemistry appropriate to the target heterocycle. In general, the sequence of steps necessary to carry out these transformations is well established in the chemistry literature. The sequence of the steps may be altered to suit the particular selection of target, available starting materials and experimental convenience. 1,2,4-Oxadiazoles and 1,2,4-triazoles are among the types of heterocycles available through this chemistry. The order of the steps may be varied to suit the particular target and efficiency of the various steps involved.

The intermediate compounds II, are either commercially available or can be prepared in a few steps using standard techniques well known to practicing medicinal chemists. The choice of protecting group will depend on the remaining steps anticipated during the rest of the synthesis of the particular target compound. Typically, benzyl-, carboxybenzyloxy- or Boc groups are used. A particularly useful guide to selection of nitrogen protecting groups is *Greene's Protective Groups in Organic Synthesis* by Peter G. M. Wuts and T. W. Greene, 4$^{th}$ ed., Wiley, 2007.

Compounds II bearing alkyl groups are also available through purchase or a series of simple synthetic steps. For example, Boc-protected 2-methyl-4-hydroxymethyl piperidine is commercially available, for example from Affinity Research Chemicals of Richmond, Del. or via synthesis using the method described in WO03103669. 4-Hydroxymethyl-2,2,6,6-tetramethylpiperidine can be prepared using the method described in WO2012068589 (U.S. application Ser. No. 13/988,180) and 2,6-dimethyl-4-hydroxymethylpiperidine can be prepared as described in US20090042900. These various intermediates can be protected and functionalized through a series of routine steps for use in the procedures outlined in the above schemes. 5-Methyl- and 5,5-dimthylpyrrolidine derivatives can be prepared from the corresponding pyrroldinones as shown in Scheme 4 and the examples reported herein.

Scheme 4.

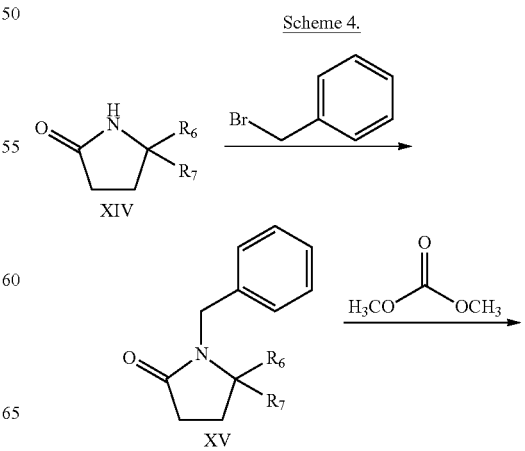

XIV

XV

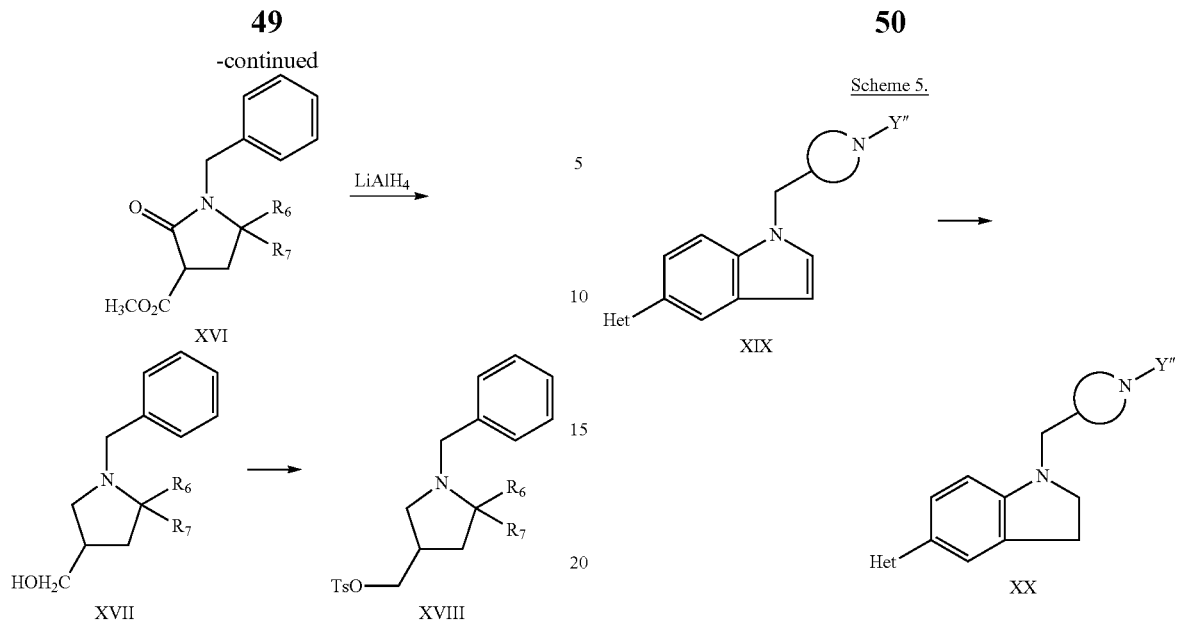

Thus, shown in Scheme 4, a compound of structure XIV in which $R_6$ is lower alkyl and $R_7$ is H or lower alkyl can be alkylated on nitrogen, for example with benzylbromide in the presence of a suitable base, for example NaH in DMF at 0° C. to give a compound of structure XV. Treatment of XV with a dialkylcarbonate, such as dimethyl carbonate in the presence of a strong base, for example lithium diisopropylamide at a temperature between −78° C. and room temperature in a suitable inert solvent such as THF leads to the corresponding alkyl ester of structure XVI. Reduction of XVI with a strong reducing agent such as lithium aluminum hydride at a temperature of 0° C. to room temperature in a suitable solvent such as THF leads to an alcohol of structure XVII in which the hydroxyl moiety can be converted into a leaving group, for example by treatment with tosyl chloride in the present of a suitable base, for example triethylamine in dichloromethane to give a compound such as XVIII, which is suitable for use in the alkylation reaction described in Scheme 1. The alcohol XVII could also be converted into other leaving groups such as a halogen if use of a tosyl group is not desired.

Intermediate bicyclic compounds II, can be prepared in a few steps using standard techniques well known to practicing medicinal chemists. Convenient starting materials include aza-bicyclic alcohols and ketones which can be homologated, for example via a Wittig reaction to a aldehyde or carboxylate which after reduction, will yield a hydroxymethyl azabicyclic derivative that in turn can be transformed to a bicyclic compound of formula II. Some references to these starting materials include: EP978,280, EP115,933, U.S. Pat. No. 4,013,668, Krow, G., et al., *Synthetic Communications* 1972, 2, 211-214, Gong, L., et al. *Bioorg Med Chem Lett* 2003, 13, 3587-3600. The choice of protecting group will depend on the remaining steps anticipated during the rest of the synthesis of the particular target compound. Typically, benzyl-, carboxybenzyloxy- or Boc groups are used.

In cases where the desired product is an indoline, it may be convenient to start with an indole using the general methods described above to prepare a compound of structure XIX, in which Y″ represents a sulfonyl derivative of the invention or a protected variant thereof or a protecting group that can be converted to a substituted sulfonyl group of the invention followed by reduction to give an indoline of formula XX as shown in Scheme 5. This transformation can conveniently be carried by treating XIX with a suitable reducing agent, for example, sodium cyanoborohydride in the presence of an acid, for example hydrochloric acid in a suitable solvent, for example ethanol.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The structures of the examples were converted into a name using ChemDraw Ultra by PerkinElmer Informatics.

Preparative purification by HPLC was carried out on a Waters 2707 Auto Purification system equipped with a 2996 PDA detector and using a X-Bridge C18, 150×30 mm ID, 5μ column; mobile phase A: 0.01M aqueous ammonium acetate, mobile phase B: acetonitrile. The gradient program was: Time (min)/% of B: 0/30, 3/30, 20/80, 25/90 and a total run time of 30 min. Detection was set at 210 nm.

Proton NMR was run on an Aligent 400MRDD2 400 MHz instrument. Analytical purity was determined on a Waters Acquity UPLC system with 2998 PDA detector using a Acquity BEH C18, 100×2.1 mm, 1.7μ column. Method 1 employed a mobile phase A of 0.025% aqueous TFA; mobile phase B of 0.025% TFA in acetonitrile and method B employed a mobile phase A of 0.25% aqueous formic acid; mobile phase B of 0.025% formic acid in acetonitrile. Run times were 6 min with the gradients determined by compound polarity; the detection range was 200 to 400 nm.

LC-MS were determined using one of two systems. Method-1 used a Waters Acquity UPLC system with 2998 PDA detector. Column: Acquity; BEH; C18, 50×2.1 mm; 1.7μ; mobile phase A: 0.025% aqueous formic acid; mobile phase B: 0.025% formic acid in acetonitrile. The gradient program varied based on compound polarity over a 5 min run time and a detection range of 200 nm to 400 nm was employed. Method-2 used a Waters Alliance 2695 HPLC system with 2998 PDA detector. Column: X-Bridge C18, 50×4.6 mm, 2.5μ; mobile phase A: 0.01M aqueous ammonium bicarbonate; mobile phase B: acetonitrile. The run time was 7 min and the gradient varied according to compound polarity; a detection range of 200-400 nm was employed. The MS detector was a Waters Single Quadra pole Mass Detector, model SQD-2 with Z-spray technique equipped with an ESI source employing both 'Positive' and 'Negative' scan modes.

Intermediate 1

Synthesis of 1-(tetrahydro-2H-pyran-2-yl)-4-(4,4,5,5-tetramethyl-1,3,2-dioxaborolan-2-yl)-1H-pyrazole

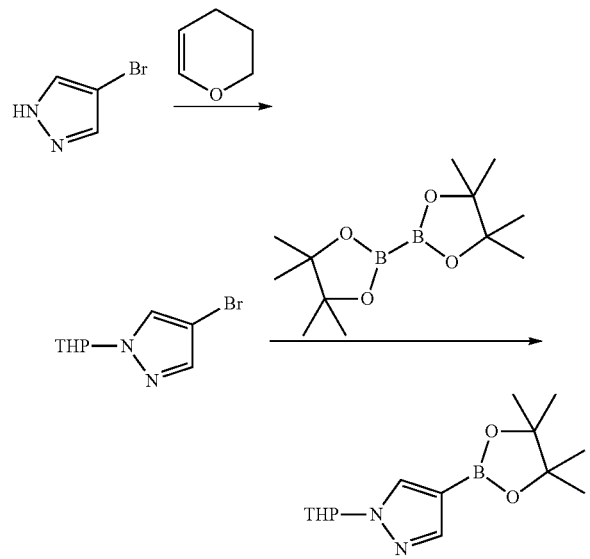

Step 1. A mixture of 4-bromo-1H-pyrazole (150 g, 1.02 mol, 1.0 eq), 3,4-dihydro-2H-pyran (128 g, 1.50 mol, 1.5 eq) and trifluoroacetic acid (7.8 mL, 0.10 mol, 0.1 eq) was stirred at 80° C. for 16 h. Progress of the reaction was monitored by TLC (10% ethyl acetate-hexane R$_f$=0.4). After completion of the reaction, the reaction mixture was diluted with ethyl acetate and was washed with saturated aqueous sodium bicarbonate and brine. The organic layer was dried over anhydrous sodium sulfate, filtered and the solvents evaporated under reduced pressure to obtain 4-bromo-1-(tetrahydro-2H-pyran-2-yl)-1H-pyrazole (180 g, 76%) as a brown oil. LCMS purity: 81.4%; (ES$^+$): m/z 231.2 (M+H$^+$); tr=1.88 min.

Step 2. Bis(pinacolato)diboron (247 g, 0.974 mol, 1.5 eq) was added to a solution of 4-bromo-1-(tetrahydro-2H-pyran-2-yl)-1H-pyrazole (150 g, 0.65 mol, 1.0 eq) in 1,4-dioxane (1500 ml) at room temperature. Potassium acetate (127 g, 1.30 mol, 2 eq) was then added and the reaction flask was purged with argon for 20 min. PdCl$_2$(dppf) DCM (26.0 g, 31.8 mmol, 0.05 eq) was added and the mixture was purged with argon for further 10 min followed by stirring at 80° C. for 12 h. After completion of the reaction (monitored by TLC, 10% ethyl acetate-hexane R$_f$=0.3), the mixture was cooled to room temperature and filtered through a bed of diatomaceous earth. The bed of diatomaceous earth was washed with ethyl acetate and the combined organic layers were evaporated under reduced pressure to give 1-(tetrahydro-2H-pyran-2-yl)-4-(4,4,5,5-tetramethyl-1,3,2-dioxaborolan-2-yl)-1H-pyrazole (280 g crude) as a brown oil. LCMS purity: 57.8%; (ES$^+$): m/z 279.18 (M+H$^+$); tr=1.95 min. The compound was used without further purification.

Intermediate 2

Synthesis of 1-(pyrrolidin-3-ylmethyl)-5-(1-(tetrahydro-2H-pyran-2-yl)-1H-pyrazol-4-yl)-1H-indole

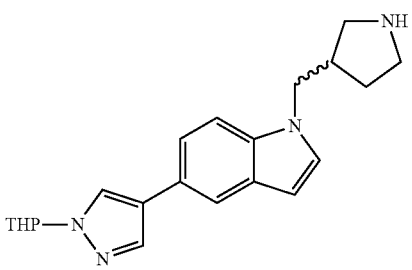

Reaction Step 1. Synthesis of benzyl 3-(tosyloxymethyl) pyrrolidine-1-carboxylate.

To a solution of benzyl 3-(hydroxymethyl)pyrrolidine-1-carboxylate (7.50 g, 31.9 mmol) and triethylamine (13 mL, 96 mmol, 3.0 eq) in dichloromethane (70 mL) was added TsCl (9.12 g, 47.8 mmol, 1.5 eq) slowly at 0° C. The mixture was allowed to warm to room temperature and stir overnight. After completion of the reaction (monitored by TLC, 50% ethyl acetate-hexane R$_f$=0.6), the mixture was poured into cool water and washed with water followed by brine. The organic layer was dried over anhydrous sodium sulphate and solvent was removed under reduced pressure. The crude product was purified by column chromatography over neutral alumina, eluting with a 0-12% gradient of ethyl acetate in hexanes to afford benzyl 3-(tosyloxymethyl)pyrrolidine-1-carboxylate (8.16 g, 68%) as a colourless oil. LCMS m/z=390 (M+1).

Reaction Step 2. Synthesis of benzyl 3-((5-bromo-1H-indol-1-yl)methyl)pyrrolidine-1-carboxylate.

Sodium hydride (0.92 g, 10.7 mmol, 1.1 eq) was added to a solution of 5-bromo indole (4.00 g, 9.68 mmol, 1 eq) in DMF (40 mL) at 0° C. After 15 minute a solution of benzyl 3-(tosyloxymethyl)pyrrolidine-1-carboxylate (8.12 g, 9.68 mmol, 1 eq) in DMF (20 mL) was added and the mixture was stirred over night at 70° C. After completion of the reaction (monitored by LCMS/TLC, 20% ethyl acetate-hexane R$_f$=0.5), the mixture was poured into ice cold water, extracted with ethyl acetate, and the combined organic layers were washed with water, followed by brine. The organic layer was dried over anhydrous sodium sulphate and solvent was removed under reduced pressure. The crude product was purified by column chromatography over neutral alumina, eluting with a 0-20% gradient of ethyl acetate in hexanes to afford benzyl 3-((5-bromo-1H-indol-1-yl)

methyl)pyrrolidine-1-carboxylate (5.00 g, 65%) as an off white solid. LCMS m/z=413 (M+1).

Reaction Step 3. Synthesis of benzyl 3-((5-(1-(tetrahydro-2H-pyran-2-yl)-1H-pyrazol-4-yl)-1H-indol-1-yl)methyl) pyrrolidine-1-carboxylate.

1-(tetrahydro-2H-pyran-2-yl)-4-(4,4,5,5-tetramethyl-1,3,2-dioxaborolan-2-yl)-1H-pyrazole (4.00 g, 14.5 mmol, 1.5 eq) was added to a solution of benzyl 4-((5-bromo-1H-indol-1-yl)methyl)pyrrolidine-1-carboxylate (4.00 g, 9.68 mmol, 1 eq) in DMF: $H_2O$ (10:1, 40 mL) at room temperature. Cesium carbonate (6.3 g, 19.4 mmol, 2 eq) was then added and the mixture was purged with argon. After 10 min, $Pd(dppf)Cl_2$ (0.79 g, 0.968 mmol, 0.1 eq) was added and the mixture was purged with argon for a further 10 min, after which period the mixture was heated to 80° C. for 5 h. After completion of the reaction (monitored by TLC, 50% ethyl acetate-hexane, $R_f$=0.4), the reaction mixture was cooled to room temperature and filtered through a bed of diatomaceous earth, washing with ethyl acetate. The combined filtrate was washed with water followed by brine and dried over anhydrous sodium sulfate. Removal of the solvents under reduced pressure gave a crude product that was purified by chromatography on neutral alumina, eluting with a 0-20% gradient of ethyl acetate in hexanes to afford benzyl 3-((5-(1-(tetrahydro-2H-pyran-2-yl)-1H-pyrazol-4-yl)-1H-indol-1-yl)methyl)pyrrolidine-1-carboxylate as a brown sticky solid. Yield=2.82 g; 60%; LCMS m/z=485 (M+1; purity=91%.

Reaction Step 4. Synthesis of 1-(pyrrolidin-3-ylmethyl)-5-(1-(tetrahydro-2H-pyran-2-yl)-1H-pyrazol-4-yl)-1H-indole.

A solution of benzyl 4-((5-(1-(tetrahydro-2H-pyran-2-yl)-1H-pyrazol-4-yl)-1H-indol-1-yl)methyl)pyrrolidine-1-carboxylate (2.80 g, 8.0 mmol, 1 eq) in EtOH (30 mL) was purged with argon for 10 min then $H_2$ for another 10 min. 10% Pd/C (0.700 g) was added and the suspension was stirred under a $H_2$ atmosphere at 40 PSI using a Parr apparatus for 6 h. After completion of reaction (monitored by TLC, 10% MeOH-dichloromethane; $R_f$=0.1), the mixture was filtered through a bed of diatomaceous earth washing with ethyl acetate. The solvents were removed under reduced pressure and the crude product was purified by column chromatography on neutral alumina, eluting with a 0-10% gradient of MeOH in dichloromethane to afford 1-(pyrrolidin-3-ylmethyl)-5-(1-(tetrahydro-2H-pyran-2-yl)-1H-pyrazol-4-yl)-1H-indole (1.32 g, 55%) as off white solid. LCMS m/z=351 (M+1), purity=94%.

Intermediate 3

Synthesis of 1-((5-methylpyrrolidin-3-yl)methyl)-5-(1-(tetrahydro-2H-pyran-2-yl)-1H-pyrazol-4-yl)-1H-indole

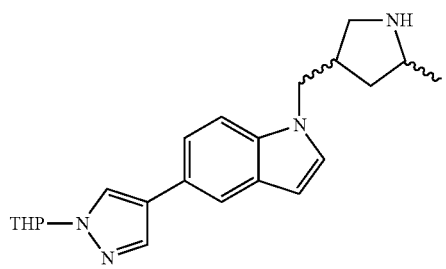

Reaction Step 1. Synthesis of 1-benzyl-5-methylpyrrolidin-2-one.

To a solution of 5-methylpyrrolidin-2-one (15 g, 152 mmol, 1.0 eq) in DMF (115 mL), was slowly added NaH (5.4 g, 230 mmol, 1.5 eq) followed by benzyl bromide (21.7 mL, 182 mmol, 1.2 eq) at 0° C. and the reaction mixture was allowed to warm to room temperature over 3 h. After completion of reaction (monitored by TLC, 20% ethyl acetate-hexane, $KMnO_4$, $R_f$=0.45), the reaction was quenched by the addition of ice cubes and was extracted with ethyl acetate (500 mL). The organic extract was dried over anhydrous sodium sulphate and the solvent removed under reduced pressure. The crude product was purified by column chromatography on silica gel (100-200 mesh), eluting with 10% ethyl acetate in hexanes to afford 25 g of 1-benzyl-5-methylpyrrolidin-2-one as oil. LC-MS ($ES^+$) m/z: 190.1 (M+1); purity=92.5%.

Reaction Step 2. Synthesis of methyl 1-benzyl-5-methyl-2-oxopyrrolidine-3-carboxylate.

To a solution of diisopropyl amine (7.84 mL, 55.5 mmol, 2.1 eq) in THF (50 mL), at −78° C. was slowly added n-BuLi (2.5 M in hexanes) (21.5 mL, 52.8 mmol, 2.0 eq) and the mixture was allowed to warm to −20° C. for 40 min. A solution of 1-benzyl-5-methylpyrrolidin-2-one (5.0 g, 26 mmol, 1.0 eq) in THF was added to the above reaction mixture at −78° C. and the mixture was stirred for 45 min. Then dimethyl carbonate (4.45 mL, 52.8 mmol, 2.0 eq) was added at −78° C. and the mixture was allowed to warm to room temperature slowly over 5 h. After completion of the reaction (monitored by TLC, 30% ethyl acetate-hexane, $KMnO_4$, $R_f$=0.65), the reaction was quenched by the slow addition of 1M HCl at 0° C. and was extracted with ethyl acetate (300 mL). The organic extract was dried over anhydrous sodium sulphate and the solvents were removed under reduced pressure to afford 2.1 g of methyl 1-benzyl-5-methyl-2-oxopyrrolidine-3-carboxylate as a sticky foam. LC-MS ($ES^+$) m/z: 248.1 (M+1); purity=92% (mixture of isomers).

Reaction Step 3. Synthesis of (1-benzyl-5-methylpyrrolidin-3-yl) methanol.

Lithium Aluminium hydride (2M in hexane, 15.7 mL, 31.5 mmol, 3.7 eq) was added slowly to a solution of methyl 1-benzyl-5-methyl-2-oxopyrrolidine-3-carboxylate (2.1 g, 8.20 mmol, 1.0 eq) in THF (35 mL), at 0° C. and the mixture was allowed to warm to room temperature over 3 h. After completion of the reaction (monitored by TLC, 30% ethyl acetate-hexane, $KMnO_4$, $R_f$=0.45), the reaction was quenched by slow addition of 1.25 mL of water and 1.25 mL of 15% NaOH solution followed by 3.75 mL of water at 0° C. The reaction mixture was filtered through a small bed of celite and the filtrate was concentrated under reduced pressure to afford 1.7 g (crude) of (1-benzyl-5-methylpyrrolidin-3-yl) methanol as sticky foam. LC-MS ($ES^+$) m/z: 206.1 (M+1); purity=80% (mixture of isomers).

Reaction Step 4. Synthesis of (1-benzyl-5-methylpyrrolidin-3-yl)methyl 4-methylbenzenesulfonate.

To a solution of (1-benzyl-5-methylpyrrolidin-3-yl) methanol (1.7 g, 8.3 mmol, 1.0 eq) in dichloromethane (25 mL), triethylamine (3.47 mL, 24.9 mmol, 3.0 eq) was added, followed by tosyl chloride (1.89 g, 10 mmol, 1.2 eq) at 0° C. The reaction mixture was allowed to warm to room temperature and was stirred for 12 h. After completion of the reaction (monitored by TLC, 50% ethyl acetate-hexane, $R_f$=0.65), the reaction mixture was quenched by addition of $NaHCO_3$ solution (25 mL) and was extracted with dichloromethane. The combined extracts were washed with brine solution. The organic layer was dried over anhydrous sodium sulphate and concentrated under reduced pressure to afford 0.92 g (31%) of (1-benzyl-5-methylpyrrolidin-3-yl) methyl 4-methylbenzenesulfonate as a sticky solid. LC-MS (ES$^+$) m/z: 360.16 (M+1); purity=75%.

Reaction Step 5. Synthesis of 1-((1-benzyl-5-methylpyrrolidin-3-yl)methyl)-5-bromo-1H-indole.

To a solution of 5-bromo-1H-indole (0.92 g, 4.7 mmol, 1.0 eq) in DMF (15 mL), NaH (0.169 g, 7.0 mmol, 1.5 eq) was added in portions at 0° C. and the reaction mixture was stirred for 30 min. A solution of (1-benzyl-5-methylpyrrolidin-3-yl)methyl 4-methylbenzenesulfonate (1.8 g, 5.1 mmol, 1.1 eq) in DMF was added, the reaction mixture was allowed to attain room temperature and was stirred for 3 h. After completion of the reaction (monitored by TLC, 50% ethyl acetate-hexane, R$_f$=0.75), the reaction mixture was quenched by addition of ice cubes and was extracted with ethyl acetate (100 mL). The organic extract was dried over anhydrous sodium sulphate and solvents were removed under reduced pressure. The crude product was purified by column chromatography on silica gel (100-200 mesh), eluting with 30% ethyl acetate in hexanes to afford 0.99 g (56%) of 1-((1-benzyl-5-methylpyrrolidin-3-yl)methyl)-5-bromo-1H-indole as a semi solid. LC-MS (ES$^+$) m/z: 383.1 (M+1); purity=92% (mixture of isomers).

Reaction Step 6. Synthesis of 1-((1-benzyl-5-methylpyrrolidin-3-yl)methyl)-5-(1-(tetrahydro-2H-pyran-2-yl)-1H-pyrazol-4-yl)-1H-indole.

To a solution of 1-((1-benzyl-5-methylpyrrolidin-3-yl) methyl)-5-bromo-1H-indole (1.2 g, 3.1 mmol, 1.0 eq) in DMF:water (4:1, 12 mL), 1-(tetrahydro-2H-pyran-2-yl)-4-(4,4,5,5-tetramethyl-1,3-dioxolan-2-yl)-1H-pyrazole (1.31 g, 4.71 mmol, 1.5 eq) was added at room temperature, followed by Cs$_2$CO$_3$ (2.0 g, 6.3 mmol, 2.0 eq). The reaction mixture was deoxygenated by purging with argon for 15 min then Pd(dppf)$_2$Cl$_2$.dichloromethane (0.25 g, 0.31 mmol, 0.1 eq), was added and the mixture was purged with argon for another 10 min. The reaction mixture was heated to 90° C. for 12 h and monitored by LCMS/TLC (50% ethyl acetate/hexane R$_f$=0.35). After completion of the reaction, the mixture was cooled to room temperature and filtered through a celite bed. The filtrate was concentrated under reduced pressure. The crude product was purified by column chromatography on silica gel (100-200 mesh), eluting with 30% ethyl acetate in hexanes to afford 0.29 g (20%) of 1-((1-benzyl-5-methylpyrrolidin-3-yl)methyl)-5-(1-(tetrahydro-2H-pyran-2-yl)-1H-pyrazol-4-yl)-1H-indole as a brown solid. LC-MS (ES$^+$) m/z: 455.27 (M+1); purity=85% (mixture of isomers).

Reaction Step 7. Synthesis of 1-((5-methylpyrrolidin-3-yl)methyl)-5-(1-(tetrahydro-2H-pyran-2-yl)-1H-pyrazol-4-yl)-1H-indole.

To a solution of 1-((1-benzyl-5-methylpyrrolidin-3-yl) methyl)-5-(1-(tetrahydro-2H-pyran-2-yl)-1H-pyrazol-4-yl)-1H-indole (2.5 g, 5.5 mmol, 1.0 eq) in methanol (25 mL), was added 20% Pd/(OH)$_2$/C (0.077 g, 0.55 mmol, 0.10 eq) followed by ammonium formate (1.38 g, 22.0 mmol, 4 eq) at room temperature and the reaction mixture was refluxed for 3 h. After completion of the reaction (monitored by TLC, 100% ethyl acetate R$_f$=0.1; LCMS), the mixture was cooled to room temperature and filtered through a celite bed. The filtrate was concentrated under reduced pressure and the crude product was purified by column chromatography over neutral alumina eluting with 30% ethyl acetate in hexanes to afford 0.5 g (25%) of 1-((5-methylpyrrolidin-3-yl)methyl)-5-(1-(tetrahydro-2H-pyran-2-yl)-1H-pyrazol-4-yl)-1H-indole as an off white solid. LC-MS (ES$^+$) m/e: 365.1 (M+1); Tr=1.36; purity=80%.

Intermediate 4

Synthesis of 1-(piperidin-4-ylmethyl)-5-(1-(tetrahydro-2H-pyran-2-yl)-1H-pyrazol-4-yl)-1H-indole

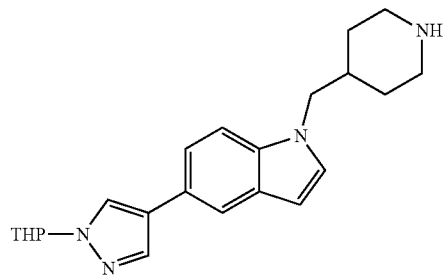

Reaction Step 1. Synthesis of benzyl 4-((tosyloxy)methyl) piperidine-1-carboxylate.

To a solution of benzyl 4-(hydroxymethyl)piperidine-1-carboxylate (150 g, 0.60 mol, 1.0 eq) and triethylamine (252 mL, 1.81 mol, 3.0 eq) in dichloromethane (1.5 L) was added tosyl chloride (171 g, 0.90 mmol, 1.5 eq) slowly at 0° C. The mixture was allowed to stir at room temperature for 16 h. After completion of the reaction (monitor by TLC, 50% ethyl acetate-hexane R$_f$=0.5), the mixture was poured into cold water and was extracted with dichloromethane. The organic extract was washed with water followed by brine, dried over anhydrous sodium sulphate, filtered and concentrated under reduced pressure. The crude product was purified by column chromatography over neutral alumina, eluting with a 0-12% gradient of ethyl acetate in hexanes to afford benzyl 4-(tosyloxymethyl)piperidine-1-carboxylate (180.0 g, 74%) as a white solid. LCMS purity: 78.8%; (ES$^+$): m/z 404.30 (M+H$^+$); tr=2.42 min.

Reaction Step 2. Synthesis of benzyl 4-((5-bromo-1H-indol-1-yl)methyl)piperidine-1-carboxylate.

Sodium hydride (60% suspension in mineral oil, 22.1 g, 0.558 mol, 1.5 eq) was added to a solution of 5-bromo indole (73.0 g, 0.372 mol, 1 eq) in DMF (300 mL) at 0° C. After 15 min, a solution of benzyl 4-(tosyloxymethyl)piperidine-1-carboxylate (180 g, 0.447 mol, 1.2 eq) in DMF (500 mL) was added and the mixture was stirred over night at 70° C. After completion of the reaction (monitor by LCMS/TLC, 20% ethyl acetate-hexane R$_f$=0.5), the mixture was poured into ice cold water, extracted with ethyl acetate and washed with water, followed by brine. The organic layer was dried over anhydrous sodium sulphate, filtered and concentrated under reduced pressure. The crude product was purified by column chromatography on neutral alumina, eluting with a 0-20% gradient of ethyl acetate in hexanes to obtain benzyl 4-((5-bromo-1H-indol-1-yl)methyl)piperidine-1-carboxylate (120 g, 76%) as a colorless sticky mass. LCMS purity: 79.5%; (ES$^+$): m/z 427.01 (M+H$^+$); tr=2.61 min.

Reaction Step 3. Synthesis of 1-(piperidin-4-ylmethyl)-5-(1-(tetrahydro-2H-pyran-2-yl)-1H-pyrazol-4-yl)-1H-indole.

1-(Tetrahydro-2H-pyran-2-yl)-4-(4,4,5,5-tetramethyl-1,3,2-dioxaborolan-2-yl)-1H-pyrazole (117 g, 421 mmol, 1.5 eq) was added to a solution of benzyl 4-((5-bromo-1H-indol-1-yl)methyl)piperidine-1-carboxylate (120 g, 281 mmol, 1.0 eq) in a mixture of DMF and water (9:1, 1200 mL) at room temperature. Potassium carbonate (77.0 g, 562 mmol, 2 eq) was then added and the reaction mixture was purged with argon for 20 min. PdCl$_2$(dppf).dichloromethane (23.0 g, 28.1 mmol, 0.1 eq) was added, argon was passed through the solution for a further 10 min and the mixture was heated at 80° C. for 6 h. After completion of the reaction (monitored by TLC, 50% ethyl acetate-hexanes, $R_f$=0.40), the reaction mixture was cooled to room temperature and filtered through a bed of diatomaceous earth washing with ethyl acetate. The combined filtrate was washed with water followed by brine, the organic layer was dried over anhydrous sodium sulphate, filtered and concentrated under reduced pressure. The crude product was purified by column chromatography over neutral alumina, eluting with a 40-50% gradient of ethyl acetate in hexanes to afford benzyl 4-((5-(1-(tetrahydro-2H-pyran-2-yl)-1H-pyrazol-3-yl)-1H-indol-1-yl)methyl)piperidine-1-carboxylate (80.0 g, 57%) as colorless oil. LCMS purity: 86.4%; (ES$^+$): m/z 499.5 (M+H$^+$); tr=2.42 min.

Reaction Step 4. Synthesis of 1-(piperidin-4-ylmethyl)-5-(1-(tetrahydro-2H-pyran-2-yl)-1H-pyrazol-4-yl)-1H-indole.

A solution of benzyl 4-((5-(1-(tetrahydro-2H-pyran-2-yl)-1H-pyrazol-4-yl)-1H-indol-1-yl)methyl)piperidine-1-carboxylate (80.0 g, 176 mmol, 1.0 eq) in EtOH (400 mL) was purged with argon for 10 min then H$_2$ for another 10 min. 10% Pd/C (12.0 g) was added and the solution was stirred under a H$_2$ atmosphere at 40 psi in a Parr apparatus for 16 h. After completion of the reaction (monitored by TLC, 10% MeOH-dichloromethane; $R_f$=0.1), catalyst was removed by filtration through a bed of diatomaceous earth washing with ethyl acetate. The combined filtrate was concentrated under reduced pressure and the crude product was purified by column chromatography on neutral alumina, eluting with a 0-10% gradient of MeOH in dichloromethane to afford 1-(piperidin-4-ylmethyl)-5-(1-(tetrahydro-2H-pyran-2-yl)-1H-pyrazol-4-yl)-1H-indole, (30 g, 44%) as an off white solid. LCMS purity: 98.0%; (ES$^+$): m/z 365.43 (M+H$^+$); tr=2.54 min. $^1$H NMR (400 MHz, DMSO-d$_6$) δ 8.23 (s, 1H), 7.88 (s, 1H), 7.74 (s, 1H), 7.45 (d, J=8 Hz, 1H), 7.36 (d, J=7.2 Hz, 1H), 7.31 (d, J=2.8 Hz, 1H), 6.38 (d, J=2.8 Hz, 1H), 5.39 (dd, J=8.4 Hz & 2 Hz, 1H), 4.01 (d, J=7.6 Hz, 2H), 3.95 (d, J=12 Hz, 1H), 3.68-3.61 (m, 1H), 2.88 (d, J=12 Hz, 2H), 2.33 (t, J=11.6 Hz, 2H), 2.19-2.10 (m, 1H), 1.99-1.87 (m, 2H), 1.86-1.81 (m, 1H), 1.72-1.66 (m, 1H), 1.57-1.53 (m, 2H), 1.39-1.35 (m, 2H), 1.17-1.04 (m, 2H).

Intermediate 5

1-(azepan-4-ylmethyl)-5-(1-(tetrahydro-2H-pyran-2-yl)-1H-pyrazol-4-yl)-1H-indole

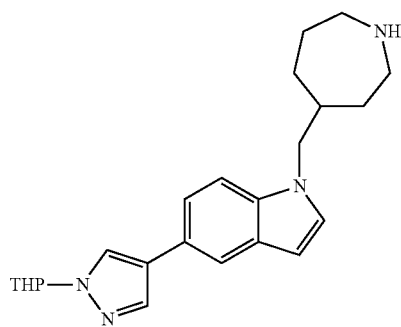

Reaction Step 1. Synthesis of 1-benzyl 4-ethyl 5-oxoazepane-1,4-dicarboxylate.

Ethyl diazoacetate (12.7 mL, 112 mmol, 1.3 eq) was added to a solution of benzyl 4-oxopiperidine-1-carboxylate (20.0 g, 85.8 mmol, 1.0 eq) in diethyl ether (200 mL) at −78° C. followed by BF$_3$.OEt$_2$ (4.4 mL, 86 mmol, 1.0 eq). The reaction mixture was stirred at −78° C. for 1 h then allowed to attain to room temperature to give a clear solution. After completion of the reaction (monitored by TLC, 20% ethyl acetate-hexane R$_f$=0.5), a saturated solution of K$_2$CO$_3$ was added to the reaction mixture and the organic layer was separated and washed with saturated K$_2$CO$_3$ solution. The organic layer was dried over anhydrous sodium sulphate and concentrated under reduced pressure. The crude product was purified by flash column chromatography on silica gel (100-200 mesh), eluting with 5% ethyl acetate in hexanes to afford 1-benzyl 4-ethyl 5-oxoazepane-1,4-dicarboxylate as a colorless oil. Yield=13.0 g, 48% LCMS m/z=320.25 (M+1); purity=>90% by $^1$H NMR.

Reaction Step 2. Synthesis of 1-benzyl 4-ethyl 5-hydroxyazepane-1,4-dicarboxylate.

Sodium borohydride (1.5 g, 40.8 mmol, 1.0 eq) was added portionwise to a solution of 1-benzyl 4-ethyl 5-oxoazepane-1,4-dicarboxylate (13.0 g, 40.8 mmol, 1.0 eq) in EtOH (130 mL) at 0° C. The reaction mixture was stirred at 0° C. for 1 h. After completion of the reaction (monitored by TLC, 30% ethyl acetate-hexane R$_f$=0.3), the reaction mixture was quenched by addition of a saturated aqueous solution of potassium sodium tartrate and the solid was filtered. The filtrate was diluted with dichloromethane and washed with a saturated solution of aqueous potassium sodium tartrate followed by water. The organic layer was dried over anhydrous sodium sulphate and concentrated under reduced pressure to give 10.0 g of crude 1-benzyl 4-ethyl 5-hydroxyazepane-1,4-dicarboxylate that was used in the next step without purification or characterization.

Reaction Step 3. Synthesis of 1-benzyl 4-ethyl 2,3,6,7-tetrahydro-1H-azepine-1,4-dicarboxylate.

To a solution of 1-benzyl 4-ethyl 5-hydroxyazepane-1,4-dicarboxylate (10.0 g, 31.0 mmol, 1.0 eq) in THF (100 mL) and triethylamine (12.6 mL 93.0 mmol, 3.0 eq) at 0° C., methanesulfonyl chloride (5.9 mL, 78 mmol, 2.5 eq) was added in three portions over 6 h. After completion of the reaction (monitored by TLC, 20% ethyl acetate-hexane R$_f$=0.3), the reaction mixture was diluted with dichloromethane and washed with saturated aqueous NaHCO$_3$. The organic layer was dried over anhydrous sodium sulphate and concentrated under reduced pressure. The residue (20 g) was dissolved in THF (10 vol), DBU (11.4 mL, 46.5 mmol, 1.5 eq) was added and the reaction mixture and heated 80° C. for 1 h. After completion of reaction (monitored by TLC, 20% ethyl acetate-hexane, R$_f$=0.6), the reaction mixture was diluted with dichloromethane and washed with saturated aqueous NaHCO$_3$. The organic layer was dried over anhydrous sodium sulphate and concentrated under reduced pressure. The crude product was purified by flash column chromatography on silica gel (100-200 mesh), eluting with 10% ethyl acetate in hexanes to afford 1-benzyl 4-ethyl 2,3,6,7-tetrahydro-1H-azepine-1,4-dicarboxylate (6.5 g, 80%) as a colorless oil. LCMS m/z=304.16 (M+1); purity=91%.

Reaction step 4. Synthesis of benzyl 4-(hydroxymethyl)azepane-1-carboxylate

LiBH$_4$ (0.80 g, 36.3 mmol, 2.0 eq) was added to a solution of 1-benzyl 4-ethyl. 2,3,6,7-tetrahydro-1H-azepine-1,4-dicarboxylate (5.50 g, 18.2 mmol, 1 eq) in THF (55 mL) at 0° C. in three portions over 30 min. The reaction mixture was heated to 60° C. for 6 h. After completion of the reaction (monitored by TLC, 20% ethyl acetate-hexane, (R$_f$=0.2), the reaction mixture was cooled to 0° C., quenched with ice cold water and extracted with ethyl acetate. The organic layer was dried over anhydrous sodium sulphate and concentrated under reduced pressure. The crude product was purified by flash column chromatography on silica gel (100-200 mesh), eluting with a 0-20% gradient of ethyl acetate in hexanes to obtain benzyl 4-(hydroxymethyl)azepane-1-carboxylate (2.80 g, 60%) as a colourless oil. LCMS m/z=264.25 (M+1), purity=95%.

Reaction step 5. Synthesis of benzyl 4-(tosyloxymethyl) azepane-1-carboxylate.

To a solution of benzyl 4-(hydroxymethyl)azepane-1-carboxylate (2.80 g, 10.6 mmol, 1 eq) in dichloromethane (28 mL) and triethylamine (4.3 mL, 31.9 mmol, 3.0) eq at 0° C., tosyl chloride (3.0 g, 15.7 mmol, 1.5 eq) was added and the reaction mixture was stirred overnight at room temperature. After completion of the reaction (monitored by TLC, 20% ethyl acetate-hexane ($R_f$=0.4), the reaction mixture was poured into ice cold water and extracted with dichloromethane. The organic extract was dried over anhydrous sodium sulfate and concentrated under reduced pressure. The crude product was purified by flash column chromatography on silica gel (100-200 mesh), eluting with a 0-10% gradient of ethyl acetate in hexanes to obtain benzyl 4-(tosyloxymethyl) azepane-1-carboxylate as a colourless oil (2.30 g, 63%). LCMS m/z=418.19 (M+1); purity=96.2%.

Reaction Step 6. Synthesis of benzyl 4-((5-bromo-1H-indol-1-yl)methyl)azepane-1-carboxylate To a solution of 5-bromo-1H-indole (1.17 g, 5.99 mmol, 1.0 eq) in anhydrous DMF (15 mL) at 0° C. was add NaH (0.260 g, 6.50 mmol, 1.1 eq) and the reaction mixture was stirred for 30 min. Benzyl 4-(tosyloxymethyl)azepane-1-carboxylate (2.5 g, 6.0 mmol, 1.0 eq) was added at room temperature and the reaction mixture was stirred overnight. After completion of the reaction (monitored by TLC, 20% ethyl acetate-hexane, ($R_f$=0.4), the reaction mixture was poured into ice cold water and extracted with dichloromethane. The organic layer was dried over anhydrous sodium sulphate and concentrated under reduced pressure. The crude product was purified by flash column chromatography on silica gel (100-200 mesh), eluting with a 0-10% gradient of ethyl acetate in hexanes to afford benzyl 4-((5-bromo-1H-indol-1-yl)methyl)azepane-1-carboxylate as a colorless oil (2.00 g, 76%). LCMS m/z=441.23 (M+1); purity=94.7%.

Reaction Step 7. Synthesis of benzyl 4-((5-(1-(tetrahydro-2H-pyran-2-yl)-1H-pyrazol-4-yl)-1H-indol-1-yl)methyl) azepane-1-carboxylate.

To a solution of benzyl 4-((5-bromo-1H-indol-1-yl) methyl)azepane-1-carboxylate (2.00 g, 4.54 mmol, 1.0 eq) in DMF:water (10:1, 20 mL) at room temperature was added 1-(tetrahydro-2H-pyran-2-yl)-4-(4,4,5,5-tetramethyl-1,3,2-dioxaborolan-2-yl)-1H-pyrazole (1.50 g, 5.44 mmol, 1.5 eq) and $Cs_2CO_3$ (3.0 g, 9.1 mmol, 2.0 eq). The mixture was purged with argon for 10 min and Pd(dppf)$Cl_2$.$CH_2Cl_2$ (0.370 g, 0.454 mmol, 0.1 eq) was added to the reaction mixture followed by purging with argon for another 10 min. The resulting reaction mixture was heated at 90° C. for 5 h. After completion of the reaction (monitored by TLC, 30% ethyl acetate-hexane $R_f$=0.35), the reaction mixture was allowed to cool and was poured into ice-cold water. The mixture was extracted with ethyl acetate and the organic phase was washed with water followed by brine. The organic layer was dried over anhydrous sodium sulphate and concentrated under reduced pressure. The crude product was purified by flash column chromatography on silica gel (100-200 mesh), eluting with a 0-20% gradient of ethyl acetate in hexanes to afford benzyl 4-((5-(1-(tetrahydro-2H-pyran-2-yl)-1H-pyrazol-4-yl)-1H-indol-1-yl)methyl) azepane-1-carboxylate (1.50 g, 60%) as an off white solid. LCMS m/z=513.6 (M+1); purity=85%.

Reaction Step 8. Synthesis of 1-(azepan-4-ylmethyl)-5-(1-(tetrahydro-2H-pyran-2-yl)-1H-pyrazol-4-yl)-1H-indole.

A suspension of 10% Pd—C (0.500 g, 0.3 eq) and benzyl 4-((5-(1-(tetrahydro-2H-pyran-2-yl)-1H-pyrazol-4-yl)-1H-indol-1-yl)methyl)azepane-1-carboxylate (1.50 g, 2.93 mmol, 1.0 eq) in EtOH (15 mL, 10 vol) at room temperature was hydrogenated under an atmosphere of hydrogen maintained by a hydrogen gas balloon for 6 hours. After completion of the reaction (monitored by TLC, 10% MeOH-dichloromethane $R_f$=0.2), the reaction mixture was filtered through a bed of diatomaceous earth, washing with ethyl acetate. The filtrate was concentrated and the crude product was purified by flash column chromatography on silica gel (100-200 mesh), eluting with a 0-15% gradient of MeOH in dichloromethane to afford 1-(azepan-4-ylmethyl)-5-(1-(tetrahydro-2H-pyran-2-yl)-1H-pyrazol-4-yl)-1H-indole as sticky mass (0.600 g, 54.5%). LCMS m/z=379.35 (M+1); purity=94.1%.

Intermediate 6

Synthesis of 1-(7-azabicyclo[2.2.1]heptan-2-ylmethyl)-5-(1-(tetrahydro-2H-pyran-2-yl)-1H-pyrazol-4-yl)-1H-indole

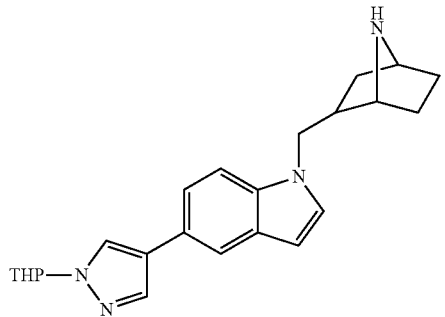

Reaction Step 1. Synthesis of ethyl 3-bromopropiolate.

Silver nitrite (1.72 g, 10.2 mmol, 0.1 eq) was added to a solution of ethyl propiolate (10.00 g, 102 mmol, 1.0 eq) in acetone (200 mL) at room temperature. The resulting reaction mixture was stirred for 5 min, then NBS (20.0 g, 112 mmol, 1.1 eq) was added and the reaction mixture stirred for 2 h at room temperature. After completion of the reaction (monitored by TLC, 5% ethyl acetate-hexane, $R_f$=0.55), the reaction mixture was filtered through a celite pad, washing with acetone. The filtrate was concentrated under reduced temperature (25-30° C.) to afford an oil. The crude product was purified by flash column chromatography on silica gel (100-200 mesh), eluting with 10% diethyl ether in hexanes to afford ethyl 3-bromopropiolate (10.0 g, 58%) as a yellow oil. LCMS m/z=176.91 (M+1).

Reaction Step 2. Synthesis of 7-tert-butyl 2-ethyl 3-bromo-7-azabicyclo[2.2.1]hepta-2,5-diene-2,7-dicarboxylate.

A mixture of methyl 3-bromopropiolate (5.00 g, 28.2 mmol, 1.0 eq) and tert-butyl 1H-pyrrole-1-carboxylate (14.0 g, 84.7 mmol, 3.0 eq) in a sealed tube was heated to 90° C. for 14 h. After completion of the reaction (monitored by TLC, 5% ethyl acetate-hexane, $R_f$=0.3), The reaction mixture was purified without work up by flash column chromatography on silica gel (100-200 mesh), eluting with 5% ethyl acetate in hexanes to afford 7-tert-butyl 2-methyl 3-bromo-7-azabicyclo[2.2.1]hepta-2,5-diene-2,7-dicarboxylate (2.0 g, 20%) as a brown oil. LCMS m/z=344.2 (M+1); purity=75%.

Reaction Step 3. Synthesis of 7-tert-butyl 2-methyl 7-azabicyclo[2.2.1]heptane-2,7-dicarboxylate.

To a stirred solution of 7-tert-butyl 2-methyl 3-bromo-7-azabicyclo[2.2.1]hepta-2,5-diene-2,7-dicarboxylate (15.0 g, 43.7 mmol, 1.0 eq) in ethanol (300 mL), was added palladium on carbon (2.0 g) and the reaction mixture was stirred at room temperature for 3 h under a hydrogen atmosphere maintained by a hydrogen filled balloon. After completion of the reaction (monitored by TLC, 10% ethyl acetate-hexane $R_f$=0.5), the mixture was filtered through a celite pad, washing with methanol. The filtrate was evaporated under reduced pressure to obtain 7-tert-butyl 2-ethyl 7-azabicyclo[2.2.1]heptane-2,7-dicarboxylate (9.90 g, 85%) as a light brown oil. LCMS m/z=255.25 (M-14) purity by $^1$H NMR >90%.

Reaction Step 4. Synthesis of ethyl 7-azabicyclo[2.2.1]heptane-2-carboxylate.

A solution of 4M HCl in dioxane (100 mL, 400 mmol, 3.0 eq) was slowly added to a stirred solution of 7-tert-butyl 2-ethyl 3-bromo-7-azabicyclo[2.2.1]heptane-2,7-dicarboxylate (20.0 g, 74.3 mmol, 1.0 eq) in dioxane (400 mL) at 0° C. and the reaction mixture was stirred at room temperature for 2 h. After completion of the reaction (monitored by TLC, 30% ethyl acetate-hexane, $R_f$=0.01), solvent was removed under reduced pressure and the residue was dried under vacuum to afford ethyl 7-azabicyclo[2.2.1]heptane-2-carboxylate HCl (12.0 g, 96%) as a yellow sticky mass. LCMS m/z=156.12 (M+1); crude purity by $^1$H NMR ~90%.

Reaction Step 5. Synthesis of 7-benzyl 2-ethyl 7-azabicyclo[2.2.1]heptane-2,7-dicarboxylate.

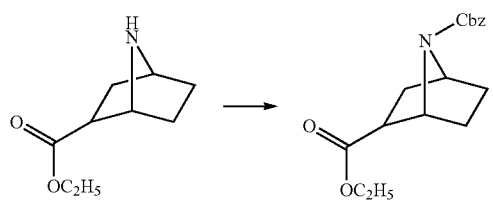 [SMILES: CCOC(=O)C1CC2CCC1N2 ; CCOC(=O)C1CC2CCC1N2C(=O)OCc1ccccc1]

To a stirred solution of ethyl 7-azabicyclo[2.2.1]heptane-2-carboxylate (12.0 g, 71.0 mmol, 1.0 eq) in dichloromethane (120 mL) was added triethylamine (25.9 mL, 355 mmol, 5.0 eq) at 0° C., and then benzyl chloroformate (13.3 g, 78.1 mmol, 1.1 eq) was slowly added. The mixture was stirred for 14 h at room temperature. After completion of the reaction (monitored by TLC, 30% ethyl acetate-hexane $R_f$=0.7), the reaction was quenched with saturated sodium bicarbonate solution, the product extracted with dichloromethane and the solvent was concentrated. The crude product was purified by flash column chromatography on silica gel (100-200 mesh), eluting with 10% ethyl acetate in hexanes to obtain 7-benzyl 2-ethyl 7-azabicyclo[2.2.1]heptane-2,7-dicarboxylate (11.8 g, 58%) as a yellow oil. LCMS m/z=290.18 (M+1).

Reaction Step 6. Synthesis of benzyl 2-(hydroxymethyl)-7-azabicyclo[2.2.1]heptane-7-carboxylate.

Lithium borohydride (5.50 g, 264 mmol, 4.0 eq) was slowly added to a stirred solution of 7-benzyl 2-ethyl 7-azabicyclo[2.2.1]heptane-2,7-dicarboxylate (20.0 g, 66.0 mmol, 1.0 eq) in tetrahydrofuran (400 mL) at 0° C. and the mixture was stirred at 60° C. for 12 h. After completion of the reaction (monitored by TLC, 30% ethyl acetate-hexanes, $R_f$=0.15), the mixture was quenched with ice cold water and the product was extracted with ethyl acetate. The organic layer was dried over anhydrous sodium sulfate and concentrated to afford benzyl 2-(hydroxymethyl)-7-azabicyclo[2.2.1]heptane-7-carboxylate (13.6 g, 80%) as a light yellow oil. LCMS m/z=262.12 (M+1).

Reaction Step 7. Synthesis of benzyl 2-(tosyloxymethyl)-7-azabicyclo[2.2.1]heptane-7-carboxylate.

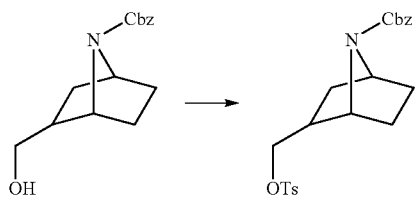 [SMILES: O=C(OCc1ccccc1)N1C2CCC1C(CO)C2 ; Cc1ccc(S(=O)(=O)OCC2CC3CCC2N3C(=O)OCc2ccccc2)cc1]

To a stirred solution of benzyl 2-(hydroxymethyl)-7-azabicyclo[2.2.1]heptane-7-carboxylate (16.0 g, 61.3 mmol, 1.0 eq) in dichloromethane (160 mL) was added triethylamine (42.7 mL, 306 mmol, 5.0 eq) at 0° C., followed by the slow addition of tosyl chloride (17.4 g, 91.9 mmol, 1.5 eq). The reaction mixture was stirred for 14 h at room temperature. After completion of the reaction (monitored by TLC, 30% ethyl acetate-hexane $R_f$=0.7), the reaction mixture was diluted with dichloromethane and washed with saturated sodium bicarbonate solution. The organic layer was dried over anhydrous sodium sulfate and concentrated under reduced pressure. The crude mass was purified by flash column chromatography on silica gel (100-200 mesh), eluting with 15% ethyl acetate in hexanes to obtain benzyl 2-(tosyloxymethyl)-7-azabicyclo[2.2.1]heptane-7-carboxylate (16.0 g, 64%) as an off white solid. LCMS m/z=416.14 (M+1).

Reaction Step 8. Synthesis of benzyl 2-((5-bromo-1H-indol-1-yl)methyl)-7-azabicyclo[2.2.1]heptane-7-carboxylate.

To a stirred solution of 5-bromoindole (6.0 g, 30.6 mmol, 1.0 eq) in DMF (60 mL) was added sodium hydride (1.50 g, 57.7 mmol, 1.5 eq) at 0° C. and the resulting reaction mixture was stirred for 10 min at 0° C. Then, a solution of benzyl 2-(tosyloxymethyl)-7-azabicyclo[2.2.1]heptane-7-carboxylate (16.0 g, 38.5 mmol, 1.2 eq) in DMF (40 mL) was added dropwise and the reaction mixture was stirred for 12 h at room temperature. After completion of the reaction (monitored by TLC, 20% ethyl acetate-hexane $R_f$=0.4), the reaction mixture was quenched with ice-cold water, extracted with ethyl acetate and the organic layer was dried over anhydrous sodium sulfate. Concentration under reduced pressure afforded a crude mass that was purified by flash column chromatography on silica gel (100-200 mesh), eluting with 10% ethyl acetate in hexanes to afford benzyl 2-((5-bromo-1H-indol-1-yl)methyl)-7-azabicyclo[2.2.1] heptane-7-carboxylate 10.0 g, 60%) white solid. LCMS m/z=439.03 (M+1).

Reaction Step 9. Synthesis of benzyl 2-((5-(1-(tetrahydro-2H-pyran-2-yl)-1H-pyrazol-4-yl)-1H-indol-1-yl)methyl)-7-azabicyclo[2.2.1]heptane-7-carboxylate.

To a mixture of 1-(tetrahydro-2H-pyran-2-yl)-4-(4,4,5,5-tetramethyl-1,3,2-dioxaborolan-2-yl)-1H-pyrazole (14.2 g, 51.2 mmol, 1.5 eq), benzyl 2-((5-bromo-1H-indol-1-yl) methyl)-7-azabicyclo[2.2.1]heptane-7-carboxylate (15.0 g, 34.1 mmol, 1.0 eq) in DMF:water (4:1, 150 mL) at room temperature was added Cs₂CO₃ (22.0 g, 68.2 mmol, 2.0 eq) and the reaction mixture was purged with argon for 10 min. PdCl$_2$(dppf)dichloromethane adduct (1.39 g, 0.17 mmol, 0.05 eq) was added to the reaction mixture and purging with argon was continued for another 10 min. The mixture was heated at 100° C. for 6 h. After completion of the reaction (monitored by TLC, 30% ethyl acetate-hexane, $R_f$=0.35), the mixture was cooled to room temperature and diluted with water. The aqueous mixture was extracted with ethyl acetate and the combined extracts were dried over anhydrous sodium sulfate, then concentrated The crude product was purified by flash column chromatography on silica gel (100-200 mesh), eluting with 20% ethyl acetate in hexanes to afford benzyl 2-((5-(1-(tetrahydro-2H-pyran-2-yl)-1H-pyrazol-4-yl)-1H-indol-1-yl)methyl)-7-azabicyclo[2.2.1]heptane-7-carboxylate (6.0 g, 35%) as a light brown sticky mass. LCMS m/z=511.6 (M+1).

Reaction Step 10. Synthesis of 1-(7-azabicyclo[2.2.1]heptan-2-ylmethyl)-5-(1-(tetrahydro-2H-pyran-2-yl)-1H-pyrazol-4-yl)-1H-indole.

To a stirred solution of benzyl 2-((5-(1-(tetrahydro-2H-pyran-2-yl)-1H-pyrazol-4-yl)-1H-indol-1-yl)methyl)-7-azabicyclo[2.2.1]heptane-7-carboxylate (5.0 g, 9.8 mmol, 1.0 eq) in ethanol (100 mL), was added 10% Pd/C (50% H₂O, Wt/Wt, 2.0 g) and the reaction mixture was stirred at room temperature for 16 h under a hydrogen atmosphere maintained by a hydrogen filled balloon. After completion of the reaction, (monitored by TLC, 10% ethyl acetate-hexane $R_f$=0.5), the mixture was filtered through a celite pad, washing with methanol The filtrate was concentrated under reduced pressure and the crude material was purified by flash column chromatography on silica gel (100-200 mesh), eluting with 5% methanol in dichloromethane to afford 1-(7-azabicyclo[2.2.1]heptan-2-ylmethyl)-5-(1-(tetrahydro-2H-pyran-2-yl)-1H-pyrazol-4-yl)-1H-indole (1.6 g, 44%) as an off white solid. LCMS m/z=377.6 (M+1); purity=94%.

Intermediate 7

Synthesis of 1-(piperidin-4-ylmethyl)-6-(1-(tetrahydro-2H-pyran-2-yl)-1H-pyrazol-4-yl)-1,2,3,4-tetrahydroquinoline

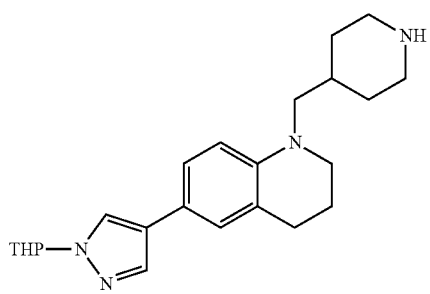

Reaction step 1. Synthesis of 6-bromo-1,2,3,4-tetrahydroquinoline.

To a stirred solution of 1,2,3,4-tetrahydroquinoline (20.0 g, 150 mmol, 1.0 eq) in acetonitrile, N-bromosuccinimide (25.5 g, 143 mmol, 0.95 eq) was added in four equal portions at 0° C., in an interval of 20 min between each portion. Stirring was continued at 0° C. for 3 h. After completion of the reaction (monitored by TLC, 10% ethyl acetate-hexane, $R_f$=0.55), diethyl ether was added and the mixture was washed with saturated sodium bicarbonate solution followed by water and brine. The organic extract was dried over anhydrous sodium sulphate, filtered and concentrated under reduced pressure. The crude product was purified by column chromatography on silica gel (100-200 mesh), eluting with 5% ethyl acetate in hexanes to obtain 6-bromo-1,2,3,4-tetrahydroquinoline (20.0 g, 64%) as yellow oil. LCMS: Purity: 92.25% (ES⁺): m/z 212.0 (M+H⁺); tr=2.06 min.

Reaction Step 2. Synthesis of benzyl 4-formylpiperidine-1-carboxylate.

To a stirred solution of benzyl 4-(hydroxymethyl)piperidine-1-carboxylate (10.0 g, 40.2 mmol, 1.0 eq) in dichloromethane (150 ml), Dess-Martin periodinane (20.4 g, 48.2 mmol, 1.2 eq) was added at 0° C. and stirring was continued at room temperature for 12 h. After completion of the reaction (monitored by TLC, 30% ethyl acetate-hexane, $R_f$=0.45), the mixture was diluted with dichloromethane and washed with saturated sodium bicarbonate solution, followed by brine. The organic extract was dried over anhydrous sodium sulphate, filtered and concentrated under reduced pressure. The crude product was purified by column chromatography on silica gel (100-200 mesh), eluting with a 30-40% gradient of ethyl acetate in hexanes to obtain benzyl 4-formylpiperidine-1-carboxylate (6.2 g, 62.5%). LCMS Purity: 78.54% (ES⁺): m/z 248.27 (M+H⁺); tr=3.01 min.

Reaction step 3. Synthesis of benzyl 4-((6-bromo-3,4-dihydroquinolin-1(2H)-yl)methyl)piperidine-1-carboxylate.

To a stirred solution of 6-bromo-1,2,3,4-tetrahydroquinoline (4.7 g, 22.2 mmol, 1.0 eq) and benzyl 4-formylpiperidine-1-carboxylate (6.05 g, 24.5 mmol, 1.1 eq) in 1,2-dichloroethane (100 ml), sodium triacetoxyborohydride (15.5 g, 73.5 mmol, 3.0 eq) was added and stirring was continued at room temperature for 3 h. After completion of the reaction (monitored by TLC, 30% ethyl acetate-hexane, $R_f$=0.40), the mixture was diluted with dichloromethane, washed with saturated sodium bicarbonate solution followed by brine. The organic extract was dried over anhydrous sodium sulphate, filtered and concentrated under reduced pressure to obtain crude benzyl 4-((6-bromo-3,4-dihydroquinolin-1(2H)-yl)methyl)piperidine-1-carboxylate (8.0 g, 81%) which was taken for next step without purification. LCMS purity: 70.29% (ES⁺): m/z 443.40 (M+H⁺); tr=2.77.

Reaction Step 4. Synthesis of benzyl 4-((6-(1-(tetrahydro-2H-pyran-2-yl)-1H-pyrazol-4-yl)-3,4-dihydroquinolin-1(2H)-yl)methyl)piperidine-1-carboxylate.

To a stirred solution of 1-(tetrahydro-2H-pyran-2-yl)-4-(4,4,5,5-tetramethyl-1,3,2-dioxaborolan-2-yl)-1H-pyrazole (7.5 g, 27.1 mmol, 1.5 eq) and benzyl 4-((6-bromo-3,4-dihydroquinolin-1(2H)-yl)methyl)piperidine-1-carboxylate (8.0 g, 18 mmol, 1.0 eq) in a mixture of DMF and water (9:1, 100 mL). Potassium carbonate (4.9 g, 36.1 mmol, 2.0 eq) was added and the mixture was purged with argon for 20 min. PdCl$_2$(dppf).dichloromethane (2.6 g, 3.26 mmol, 0.1 eq) was added, purging with argon continued for a further 10 min and the mixture was then heated at 90° C. for 12 h. After completion of the reaction (monitored by TLC, 30% ethyl acetate-hexane, $R_f$=0.30), the mixture was cooled to room temperature and poured into ice cold water. The aqueous mixture was extracted with ethyl acetate, the extract was washed with water followed by brine and was dried over anhydrous sodium sulfate The solution was filtered and concentrated under reduced pressure. The crude product was purified by column chromatography on neutral alumina, eluting with a 20-30% gradient of ethyl acetate in hexanes to afford benzyl 4-((6-(1-(tetrahydro-2H-pyran-2-yl)-1H-pyrazol-4-yl)-3,4-dihydroquinolin-1(2H)-yl)methyl)piperidine-1-carboxylate (1.5 g, 16%) as a colourless viscous liquid LCMS: purity 97.1%; (ES+): m/z 515.34 (M+H+); tr=2.57 min.

Reaction Step 5. Synthesis of 1-(piperidin-4-ylmethyl)-6-(1-(tetrahydro-2H-pyran-2-yl)-1H-pyrazol-4-yl)-1,2,3,4-tetrahydroquinoline.

To a stirred solution of benzyl 4-((6-(1-(tetrahydro-2H-pyran-2-yl)-1H-pyrazol-4-yl)-3,4-dihydroquinolin-1(2H)-yl)methyl)piperidine-1-carboxylate (1.5 g, 2.91 mmol, 1.0 eq) in ethanol (20 ml), palladium on charcoal (10% w/w, 50% moisture, 0.5 g) was added under a nitrogen atmosphere and the mixture was stirred under hydrogen pressure (at 40 psi) in a Parr shaker at room temperature for 12 h. After completion of the reaction (monitored by TLC, 5% methanol-dichloromethane, $R_f$=0.15) the mixture was filtered through a celite bed and the celite bed was washed with methanol. The filtrate was concentrated under reduced pressure. The crude product was purified by column chromatography on neutral alumina, eluting with a 5-10% gradient of MeOH in dichloromethane to afford 1-(piperidin-4-ylmethyl)-6-(1-(tetrahydro-2H-pyran-2-yl)-1H-pyrazol-4-yl)-1,2,3,4-tetrahydroquinoline (0.76 g, 68%) as a colourless gel. LCMS purity: 75.17%; (ES+): m/z 381.22 (M+H+); tr=1.46 min.

Intermediate 8

Synthesis of (1-benzyl-5,5-dimethylpyrrolidin-3-yl)methyl 4-methylbenzenesulfonate

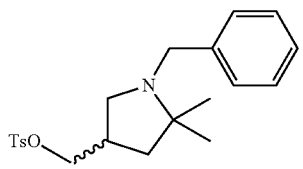 [SMILES: Cc1ccc(S(=O)(=O)OCC2CN(Cc3ccccc3)C(C)(C)C2)cc1]

Reaction Step 1. Synthesis of 1-benzyl-5,5-dimethylpyrrolidin-2-one.

To a solution of 5,5-dimethylpyrrolidin-2-one (35.0 g, 310 mmol, 1.0 eq) in DMF (350 mL), NaH (60% suspension in paraffin oil, 18.6 g, 465 mmol, 1.5 eq) was slowly added followed by benzyl bromide (44.0 mL, 372 mmol, 1.2 eq) at 0° C., the mixture was allowed to warm to room temperature with continuous stirring and was stirred at rt for 16 h. After completion of the reaction (monitored by TLC, 50% ethyl acetate-hexane, $R_f$=0.50), reaction mixture was quenched by the addition of ice cubes and extracted with ethyl acetate (500 mL). The organic extract was dried over anhydrous sodium sulphate, filtered and concentrated under reduced pressure. The crude product was purified by column chromatography on silica gel (100-200 mesh), eluting with a 40% gradient of ethyl acetate in hexanes to afford 1-benzyl-5,5-dimethylpyrrolidin-2-one (40.0 g, 63.6%) as colourless viscous liquid. LCMS purity: 90.58%; (ES+): m/z 204.2 (M+H+); tr=1.77 min.

Reaction Step 2. Synthesis of methyl 1-benzyl-5,5-dimethyl-2-oxopyrrolidine-3-carboxylate.

A stirred solution of diisopropyl amine (63.0 mL, 394 mmol, 2.0 eq) in THF (400 mL) was cooled to −78° C., n-BuLi (2.5M in hexanes, 164.0 mL, 394 mmol, 2.0 eq) was slowly added. The mixture was allowed to warm to −20° C. and was stirred at −20° C. for 90 min. The mixture was then again cooled to −78° C. and a solution of 1-benzyl-5,5-dimethylpyrrolidin-2-one (40.0 g, 197 mmol, 1.0 eq) in THF (100 mL) was added slowly to the above mixture. Stirring was continued at −78° C. for 60 min followed by addition of dimethyl carbonate (36.0 mL, 413 mmol, 2.1 eq) slowly, while maintaining the temperature at −78° C. After completion of the addition, the mixture was allowed to warm to room temperature over 4 h. After completion of the reaction (monitored by TLC, 50% ethyl acetate-hexanes, $R_f$=0.55), the reaction mixture was quenched by the slow addition of 1M HCl at 0° C. and the mixture was extracted with ethyl acetate. The organic extract was dried over anhydrous sodium sulphate, filtered and concentrated under reduced pressure to afford methyl 1-benzyl-5,5-dimethyl-2-oxopyrrolidine-3-carboxylate (20.0 g, 40%) as colorless viscous liquid. LCMS purity: 90.0%; (ES+): m/z 262.01 (M+H+); tr=1.82 min.

Reaction Step 3. Synthesis of (1-benzyl-5,5-dimethylpyrrolidin-3-yl)methanol.

Lithium aluminium hydride (2M in hexane, 145 mL, 306 mmol, 4.0 eq) was added slowly to a stirred solution of methyl 1-benzyl-5,5-dimethyl-2-oxopyrrolidine-3-carboxylate (20.0 g, 76.6 mmol, 1.0 eq) in THF (200 mL) at 0° C. and stirring was continued while the mixture was allowed to warm up to room temperature over a period of 6 h. After completion of the reaction (monitored by TLC, 30% ethyl acetate-hexanes, $R_f$=0.25), the reaction was quenched by the slow addition of 20 mL of water and 20 mL of 15% aqueous NaOH followed by 40 mL of water at 0° C. The precipitated solid was removed by filtering the mixture through a bed of celite and the filtrate was concentrated under reduced pressure. The crude product was purified by column chromatography on silica gel (100-200 mesh), eluting with 40% ethyl acetate in hexanes to afford (1-benzyl-5,5-dimethyl-pyrrolidin-3-yl)methanol (9.0 g, 53.8%) as colorless gel. LCMS purity: 89.15%; (ES+): m/z 220.30 (M+H+); tr=3.11 min.

Reaction Step 4. Synthesis of (1-benzyl-5,5-dimethylpyrrolidin-3-yl)methyl 4-methylbenzenesulfonate.

To a solution of (1-benzyl-5,5-dimethylpyrrolidin-3-yl)methanol (5.0 g 23 mmol, 1.0 eq) in dichloromethane (50 mL), triethylamine (9.3 mL, 68 mmol, 3.0 eq) was added, p-toluene sulfonyl chloride (5.2 g, 27.4 mmol, 1.2 eq) at 0° C. and the reaction mixture was stirred at room temperature for 12 h. After completion of the reaction (monitored by TLC, 50% ethyl acetate-hexane, $R_f$=0.65), the reaction mixture was poured into ice-cold water and was extracted with dichloromethane. The organic extract was washed with brine, dried over anhydrous sodium sulphate, filtered and concentrated under reduced pressure. The crude product was purified by column chromatography on silica gel (100-200 mesh), eluting with a 10-15% gradient of ethyl acetate in hexanes to afford (1-benzyl-5,5-dimethylpyrrolidin-3-yl) methyl 4-methylbenzenesulfonate (5.8 g, 68%) as colorless gel. LCMS purity: 78.3%; (ES+): m/z 374.32 (M+H+); tr=4.28 min.

Intermediate 9

Synthesis of 5-(1-(tetrahydro-2H-pyran-2-yl)-1H-pyrazol-4-yl)-1H-indole

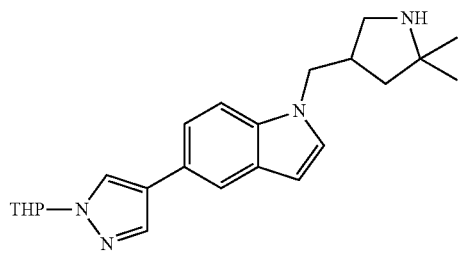

Reaction Step 1. Synthesis of 5-(1-(tetrahydro-2H-pyran-2-yl)-1H-pyrazol-4-yl)-1H-indole.

To a solution of 5-bromo-1H-indole (10.0 g, 51.0 mmol, 1.0 eq) in a mixture of DMF and water (9:1, 100 mL), 1-(tetrahydro-2H-pyran-2-yl)-4-(4,4,5,5-tetramethyl-1,3-dioxolan-2-yl)-1H-pyrazole (21.2 g, 76.5 mmol, 1.5 eq) was added at room temperature, followed by $Cs_2CO_3$ (33.0 g, 102 mmol, 2.0 eq). The mixture was purged with argon for 15 min, $Pd(dppf)_2Cl_2$.DCM (4.1 g, 5.1 mmol, 0.1 eq) was added followed by purging with argon for further 10 min and the mixture was heated at 90° C. for 12 h. After completion of the reaction (monitored by TLC 30% ethyl acetate in hexanes $R_f$=0.35), the mixture was cooled to room temperature and filtered through a bed of diatomaceous earth, washing with ethyl acetate. The combined filtrate was washed with water followed by brine, the organic layer was dried over anhydrous sodium sulfate, filtered and concentrated under reduced pressure. The crude product was purified by column chromatography on silica gel (100-200 mesh), eluting with a 20-30% gradient of ethyl acetate in hexanes to afford 5-(1-(tetrahydro-2H-pyran-2-yl)-1H-pyrazol-4-yl)-1H-indole (9.0 g, 66%) as a white solid. LCMS purity: 68%; ($ES^+$): m/z 268.06 ($M+H^+$); tr=1.85 min.

Reaction Step 2. Synthesis of 1-((1-benzyl-5,5-dimethylpyrrolidin-3-yl)methyl)-5-(1-(tetrahydro-2H-pyran-2-yl)-1H-pyrazol-4-yl)-1H-indole.

To a stirred solution of 5-(1-(tetrahydro-2H-pyran-2-yl)-1H-pyrazol-4-yl)-1H-indole (6.0 g, 22.5 mmol, 1.0 eq) in DMF (40 mL) was added NaH (60% in paraffin oil, 1.35 g, 33.7 mmol, 1.5 eq) at 0° C. and the mixture was allowed to stir at room temperature for 30 min. Then a solution of (1-benzyl-5,5-dimethylpyrrolidin-3-yl)methyl 4-methylbenzenesulfonate (10.0 g, 27.0 mmol, 1.2 eq) in DMF (20 mL) at 0° C. was slowly added and stirring continued at room temperature for 16 h. After completion of the reaction (monitored by TLC, 30% ethyl acetate in hexanes, $R_f$=0.45), the reaction was quenched by adding ice cubes and was extracted with ethyl acetate. The organic extract was dried over anhydrous sodium sulphate, filtered and concentrated under reduced pressure to obtain crude 1-((1-benzyl-5,5-dimethylpyrrolidin-3-yl)methyl)-5-(1-(tetrahydro-2H-pyran-2-yl)-1H-pyrazol-4-yl)-1H-indole (5.0 g, 48%) as a colorless viscous liquid, which was used as such in the next step. LCMS: purity 73.0%; ($ES^+$): m/z: 469.31 ($M+H^+$); tr=1.62 min.

Reaction Step 3. Synthesis of 1-((5,5-dimethylpyrrolidin-3-yl)methyl)-5-(1-(tetrahydro-2H-pyran-2-yl)-1H-pyrazol-4-yl)-1H-indole.

To a solution of 1-((1-benzyl-5,5-dimethylpyrrolidin-3-yl)methyl)-5-(1-(tetrahydro-2H-pyran-2-yl)-1H-pyrazol-4-yl)-1H-indole (5.0 g, 10.7 mmol, 1.0 eq) in methanol (50 mL), was added $Pd(OH)_2$ on charcoal (20% w/w, 50% moisture, 1.0 g,) followed by ammonium formate (2.7 g, 42.8 mmol, 4 eq) at room temperature and the reaction mixture was refluxed for 2 h. After completion of the reaction (monitored by TLC, 100% ethyl acetate $R_f$=0.1), the mixture was cooled to room temperature and filtered through a celite bed. The filtrate was concentrated under reduced pressure and the crude product was triturated in a mixture of diethyl ether and hexanes (3:1) to afford 1-((5,5-dimethylpyrrolidin-3-yl)methyl)-5-(1-(tetrahydro-2H-pyran-2-yl)-1H-pyrazol-4-yl)-1H-indole (2.8 g 70.0%) as an off white solid. LCMS purity: 90.58%; ($ES^+$) m/z: 379.3 ($M+H^+$). tr=1.48.

Intermediate 10

Synthesis of (azidomethyl)trimethylsilane

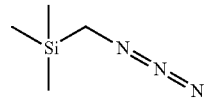

To a stirred solution of (chloromethyl)trimethylsilane (1.0 g, 8.15 mmol, 1.0 eq), in DMF (10 mL), sodium azide (1.60 g, 24.6 mmol, 3.0 eq) and KI (0.025 g, cat.) were added and stirring was continued at room temperature for 10 min. The temperature of the reaction mixture was then slowly raised to 60° C. and stirring continued at 60° C. for 12 h. After completion of the reaction (monitored by TLC, 10% ethyl acetate in hexanes $R_f$=0.2), the mixture was poured into chilled water and extracted with ethyl acetate. The organic extract was washed with water followed by brine, dried over anhydrous sodium sulfate, filtered and concentrated under reduced pressure to obtain crude (azidomethyl)trimethylsilane (1.20 g) as a colourless liquid, which was used without further purification and characterization.

Intermediate 11

Synthesis of 5-bromo-1-(piperidin-4-ylmethyl)-1H-indole

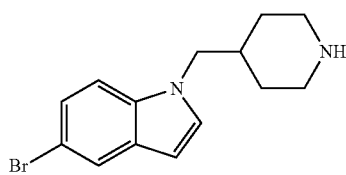 [SMILES: Brc1ccc2c(ccn2CC2CCNCC2)c1]

Reaction Step 1. Synthesis of tert-butyl 4-(tosyloxymethyl)piperidine-1-carboxylate.

To a solution of tert-butyl 4-(hydroxymethyl)piperidine-1-carboxylate (30.0 g, 139 mmol, 1.0 eq) and triethylamine (58.0 mL, 147 mmol, 3.0 eq) in dichloromethane (300 mL) was added TsCl (39.8 g, 209 mmol, 1.5 eq) slowly at 0° C.

The mixture was allowed to stir at room temperature for 16 h. After completion of the reaction (monitored by TLC, 50% ethyl acetate-hexane, $R_f$=0.5), the mixture was poured into cold water and extracted with dichloromethane. The organic extract was washed with water followed by brine, dried over anhydrous sodium sulphate, filtered and concentrated under reduced pressure. The crude product was purified by column chromatography on neutral alumina, eluting with a 0-12% gradient of ethyl acetate in hexanes to afford tert-butyl 4-(tosyloxymethyl)piperidine-1-carboxylate (40.0 g, 78%) as a white solid. LCMS purity: 89.04%; (ES$^+$): m/z 370.17 (M+H$^+$); tr=2.35 min.

Reaction Step 2. Synthesis of tert-butyl 4-((5-bromo-1H-indol-1-yl)methyl)piperidine-1-carboxylate.

NaH (60% suspension in mineral oil, 6.44 g, 268 mmol, 1.5 eq) was added to a solution of 5-bromoindole (19.0 g, 98.5 mmol, 1 eq) in DMF (200 mL) at 0° C. After 15 minutes, a solution of tert-butyl 4-(tosyloxymethyl)piperidine-1-carboxylate (40.0 g, 108 mmol, 1.1 eq) in DMF (200 mL) was added and the mixture was stirred at room temperature for 16 h. After completion of the reaction (monitored by LCMS/TLC, 20% ethyl acetate-hexane $R_f$=0.5), the mixture was poured into ice cold water, extracted with ethyl acetate and the organic layer was washed with water, followed by brine. The organic layer was dried over anhydrous sodium sulphate, filtered and concentrated under reduced pressure. The crude product was purified by column chromatography on neutral alumina, eluting with a 0-20% gradient of ethyl acetate in hexanes to afford tert-butyl 4-((5-bromo-1H-indol-1-yl)methyl)piperidine-1-carboxylate (30.0 g, 77.7%) as a white solid. LCMS purity: 82.75%; (ES$^4$): m/z 337.08 (M+H$^+$-$^t$Bu); tr=2.62 min.

Reaction step 3. Synthesis of 5-bromo-1-(piperidin-4-ylmethyl)-1H-indole.

To a solution of tert-butyl 4-((5-bromo-1H-indol-1-yl)methyl)piperidine-1-carboxylate (15.0 g, 0.285 mmol, 1.0 eq) in 1,4-dioxane (200 mL) at 0° C. was slowly added 4N hydrogen chloride in 1,4-dioxane (30 mL) and the mixture was allowed to stir at room temperature for 16 h. After completion of the reaction (monitored by TLC, 10% methanol in dichloromethane, $R_f$=0.2), the solvents were evaporated under reduced pressure and the residue was triturated with diethyl ether to give 5-bromo-1-(piperidin-4-ylmethyl)-1H-indole hydrochloride (9.52 g, 85%) as a white solid. LCMS purity: 91.12%; (ES$^+$): m/z 293.14 (M+H$^+$); tr=1.52 min.

Intermediate 12

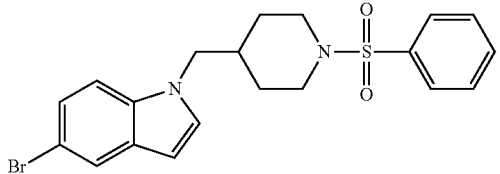 [SMILES: O=S(=O)(c1ccccc1)N1CCC(Cn2ccc3cc(Br)ccc32)CC1]

5-bromo-1-((1-(phenylsulfonyl)piperidin-4-yl)methyl)-1H-indole can be prepared from 5-bromo-1-(piperidin-4-ylmethyl)-1H-indole by treatment with benzene sulfonyl chloride using the method described in example 1.

Intermediate 13

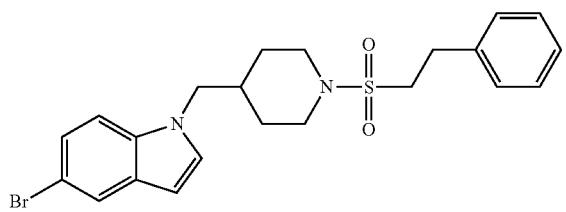 [SMILES: O=S(=O)(CCc1ccccc1)N1CCC(Cn2ccc3cc(Br)ccc32)CC1]

5-bromo-1-((1-(phenethylsulfonyl)piperidin-4-yl)methyl)-1H-indole can be prepared from 5-bromo-1-(piperidin-4-ylmethyl)-1H-indole by treatment with phenylethyl sulfonyl chloride using the method described in example 1.

Intermediate 14

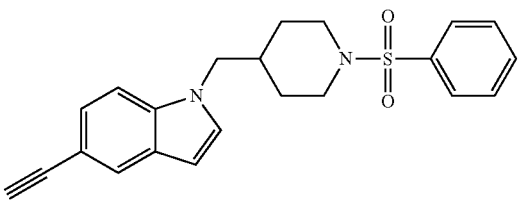 [SMILES: C#Cc1ccc2c(ccn2CC2CCN(S(=O)(=O)c3ccccc3)CC2)c1]

5-Ethynyl-1-((1-(phenylsulfonyl)piperidin-4-yl)methyl)-1H-indole can be prepared by deoxyenation of a solution of 5-bromo-1-((1-(phenylsulfonyl)piperidin-4-yl)methyl)-1H-indole (1 eq), CuI (0.1 eq), triphenyl phosphine (0.5 eq) and ethynyltrimethylsilane (3.0 eq) in a solvent of triethylamine followed by addition of bis(triphenylphosphine)palladium (II) dichloride (0.1 eq) and heating at 80° C. until the reaction is complete. The product, 1-((1-(phenylsulfonyl) piperidin-4-yl)methyl)-5-((trimethylsilyl)ethynyl)-1H-indole can be isolated by dilution with water, extraction with ethyl acetate and concentration. Treatment with an excess of potassium carbonate in methanol at room temperature then can afford 5-ethynyl-1-((1-(phenylsulfonyl)piperidin-4-yl) methyl)-1H-indole.

Intermediate 15

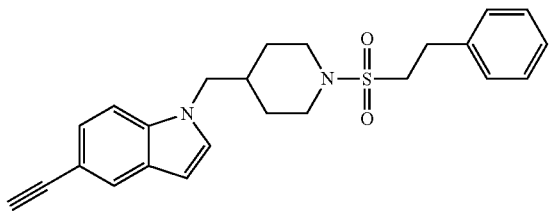 [SMILES: C#Cc1ccc2c(ccn2CC2CCN(S(=O)(=O)CCc3ccccc3)CC2)c1]

5-Ethynyl-1-((1-(phenethylsulfonyl)piperidin-4-yl) methyl)-1H-indole can be prepared by deoxyenation of a solution of 5-bromo-1-((1-(phenylethylsulfonyl)piperidin-4-yl)methyl)-1H-indole (1 eq), CuI (0.1 eq), triphenyl phosphine (0.5 eq) and ethynyltrimethylsilane (3.0 eq) in a solvent of triethylamine followed by addition of bis(triphenylphosphine)palladium(II) dichloride (0.1 eq) and heating at 80° C. until the reaction is complete. The product, 1-((1-(phenylethylsulfonyl)piperidin-4-yl)methyl)-5-((trimethylsilyl)ethynyl)-1H-indole can be isolated by dilution with water, extraction with ethyl acetate and concentration. Treatment with an excess of potassium carbonate in methanol at room temperature then can afford 5-ethynyl-1-((1-(phenylethylsulfonyl)piperidin-4-yl)methyl)-1H-indole.

Intermediates 16 and 17

Synthesis of cis- and trans-1-benzyl-5-methylpyrrolidin-3-yl)methyl 4-methylbenzenesulfonate

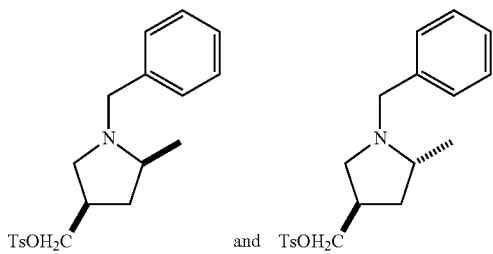

Step 1: Synthesis of 1-benzyl-5-methylpyrrolidin-2-one.

To a stirred solution of 5-methylpyrrolidin-2-one (200 g, 2.02 mol, 1.0 eq) in DMF (1.5 L), sodium hydride (60% suspension on mineral oil, 131 g, 3.03 mol, 1.5 eq) was slowly added at 0° C., followed by benzyl bromide (292 mL, 2.42 mol, 1.2 eq) and the mixture was allowed stir at room temperature for 3 h. After completion of the reaction (monitored by TLC, 20% ethyl acetate-hexane, KMnO$_4$, R$_f$=0.45), the reaction was quenched by adding ice cubes and the mixture was extracted with ethyl acetate (500 mL). The organic extract was dried over anhydrous sodium sulfate, filtered and concentrated under reduced pressure. The crude product was purified by column chromatography on silica gel (100-200 mesh), eluting with 10% ethyl acetate in hexanes to afford 1-benzyl-5-methylpyrrolidin-2-one in two fractions. The first fraction contained 200 g of 1-benzyl-5-methylpyrrolidin-2-one (yield 52.4%, LC-MS: purity: 95%) and the second fraction contained an additional 100 g (yield 26%, LC-MS: purity: 83%) as an oily liquid. (ES$^+$): m/z 190.1 (M+H$^+$); tr=1.21, 1.61 min.

Step 2: Synthesis of methyl 1-benzyl-5-methyl-2-oxopyrrolidine-3-carboxylate and 1-benzyl-5-methyl-2-oxopyrrolidine-3-carboxylic acid.

n-BuLi (2.5M in hexanes, 215 mL, 0.528 mol, 2.0 eq) was slowly added to a stirred solution of diisopropyl amine (78.4 mL, 0.555 mol, 2.1 eq) in THF (500 mL), at −78° C. and stirring was continued for 40 min, during which time, the temperature of the reaction was allowed to rise up to −20° C. The mixture was again cooled to −78° C., a solution of 1-benzyl-5-methylpyrrolidin-2-one (50 g, 0.265 mol, 1.0 eq) in THF (5.0 L) was added and stirring continued for 45 min, maintain the same temperature. Then dimethyl carbonate (44.5 mL, 0.528 mol, 2.0 eq) was added to the above mixture and stirring continued for 5 h, during which time, the temperature of the reaction was allowed to rise to rt. After completion (monitored by TLC, 30% ethyl acetate-hexanes, KMnO$_4$, R$_f$=0.65), the reaction was quenched by slowly adding 1M aq NH$_4$Cl at 0° C. and the mixture was extracted with ethyl acetate (3 L). The organic extract was dried over anhydrous sodium sulfate, filtered and concentrated under reduced pressure to afford crude methyl 1-benzyl-5-methyl-2-oxopyrrolidine-3-carboxylate (4.5 g, 6.8% mixture of diastereomers) as a brown sticky mass. LC-MS purity: 37.5%, (ES$^+$) m/z: 248.1 (M+H$^+$), tr=1.32, 1.71.

The aqueous extract was acidified with 2N HCl to pH 2 and again extracted with ethyl acetate (5 L). The organic extract was dried over anhydrous sodium sulfate, filtered and concentrated under reduced pressure to afford 1-benzyl-5-methyl-2-oxopyrrolidine-3-carboxylic acid (40.1 g, 65%, mixture of diastereomers) brown sticky mass. LC-MS purity: 68% (ES$^+$): m/z 234.1 (M+H$^+$). tr=1.46, 1.49.

Step 3: Synthesis of (1-benzyl-5-methylpyrrolidin-3-yl) methanol.

Lithium aluminium hydride (2M in THF, 253 mL, 252 mmol, 2.35 eq) was added to a stirred solution of 1-benzyl-5-methyl-2-oxopyrrolidine-3-carboxylic acid (25 g, 107 mmol, 1.0 eq) in THF (250 mL), at 0° C. and stirring was continued for 3 h, during time which temperature of the reaction was allowed to rise to room temperature. After completion (monitored by TLC, 30% ethyl acetate-hexanes, KMnO$_4$, R$_f$=0.65), the reaction was again cooled to 0° C. and excess lithium aluminium hydride was quenched by addition of 15 mL of water very slowly over a period of 3 h. The white precipitate formed was filtered through a celite bed and the filtrate was concentrated under reduced pressure to afford crude (1-benzyl-5-methylpyrrolidin-3-yl) methanol (9 g, mixture of diastereomers) as a brown sticky mass, which was used as such in the next step. LC-MS purity: 68.03%. (ES$^+$): m/z 206.1 (M+H$^+$). tr=0.50, 0.60.

Step 4: Synthesis of (1-benzyl-5-methylpyrrolidin-3-yl) methyl 4-methylbenzenesulfonate.

To a stirred solution of (1-benzyl-5-methylpyrrolidin-3-yl)methanol (40 g, 195 mmol, 1.0 eq) in dichloromethane (250 mL), triethylamine (81.5 mL, 59 mmol, 3.0 eq) was slowly added at 0° C. followed by tosyl chloride (44.6 g, 234 mmol, 1.2 eq) and the mixture was allowed to stir at room temperature for 12 h. After completion of the reaction (monitored by TLC, 50% ethyl acetate-hexanes, R$_f$=0.65), saturated aqueous NaHCO$_3$ solution (25 mL) was added and the organic layer was separated. The aqueous layer was further extracted with dichloromethane (120 mL). The combined organic extract was dried over anhydrous sodium sulfate, filtered and concentrated under reduced pressure to afford crude (1-benzyl-5-methylpyrrolidin-3-yl)methyl 4-methylbenzenesulfonate (32 g, mixture of diastereomers) as brown sticky mass. LC-MS purity: 94.65%. (ES$^+$): m/z 360.16 (M+H$^+$). tr=1.40, 1.53.

Step 5: Separation of cis and trans isomers of (1-benzyl-5-methylpyrrolidin-3-yl) methyl 4-methylbenzenesulfonate.

A mixture of cis and trans isomers of (1-benzyl-5-methylpyrrolidin-3-yl)methyl 4-methylbenzenesulfonate (63 g) was purified by column chromatography on silica gel, (5 kg) 100-200 mesh, eluting with 10% ethyl acetate in hexanes to obtain cis-(1-benzyl-5-methylpyrrolidin-3-yl) methyl 4-methylbenzenesulfonate (Intermediate 16, 19.6 g, 31.1%) as a pale brown liquid and trans-(1-benzyl-5-methylpyrrolidin-3-yl) methyl 4-methylbenzenesulfonate (Intermediate 17, 25.9 g, 41.1) as an off white solid.

Data for cis-(1-benzyl-5-methylpyrrolidin-3-yl) methyl 4-methylbenzenesulfonate (intermediate 16):

LC-MS purity: 91.78%; (ES$^+$): m/z 360.32 (M+H$^+$); tr=4.42 min. $^1$H NMR (400 MHz, CDCl$_3$) δ 7.73 (d, J=8.4 Hz, 2H), 7.31-7.22 (m, 7H), 3.95 (d, J=8.4 Hz, 1H), 3.87 (dd, J=1.6, 8.4 Hz, 2H), 3.06 (d, J=13.2 Hz, 1H), 2.62 (dd, J=2.4, 10.4 Hz, 1H), 2.44 (s, 3H), 2.42-2.00 (m, 4H), 1.09-1.00 (m, 4H).

Data for trans-(1-benzyl-5-methylpyrrolidin-3-yl) methyl 4-methylbenzenesulfonate (intermediate 17):

LC-MS purity: 94.64%; (ES$^+$): m/z 360.32 (M+H$^+$); tr=4.64 min.

$^1$H NMR (400 MHz, CDCl$_3$) δ 7.73 (d, J=8.0 Hz, 2H), 7.33-7.21 (m, 7H), 3.98 (m, 3H), 3.04 (d, J=12.8 Hz, 1H), 2.95 (dd, J=2.0, 7.2 Hz, 1H), 2.45 (s, 3H), 2.42-2.37 (m, 2H), 1.79 (d, J=8.4 Hz, 1H), 1.66-1.54 (m, 2H), 1.12 (d, 3H).

Structural Assignment of Intermediate 17.

To a solution of trans-(1-benzyl-5-methylpyrrolidin-3-yl) methyl 4-methylbenzenesulfonate (intermediate 17, 0.2 g, 0.55 mmol, 1.0 eq) in DMF (5 mL) was added tetrabutyl ammonium acetate (0.215 g, 0.715 mmol, 1.3 eq) at room temperature and the mixture was stirred at 70° C. for 4 h. After completion of the reaction (monitored by TLC 70% ethyl acetate-hexanes R$_f$=0.36), DMF was removed under reduced pressure and the residue was partitioned between ethyl acetate (20 mL) and water (10 mL). The organic extract was dried over anhydrous sodium sulfate, filtered and concentrated under reduced pressure. The crude product was purified by column chromatography on silica gel (100-200 mesh), eluting with 5% methanol in dichloromethane to obtain trans-(1-benzyl-5-methylpyrrolidin-3-yl)methanol (0.10 g, 87%) as pale brown liquid. LC-MS purity: 94.95%; (ES$^+$): m/z (M+H$^+$). $^1$H NMR (400 MHz, DMSO-d$_6$): δ 7.33-7.22 (m, 5H), 3.98 (d, J=12.8 Hz, 1H), 3.46-3.59 (m, 1H), 3.30-3.40 (m, 1H), 3.15 (d, J=12.8 Hz, 1H), 3.03 (m, 1H), 2.50-2.57 (m, 1H), 2.27-2.40 (m, 1H), 1.92-2.01 (m, 1H), 1.62-1.69 (m, 1H), 1.44-1.48 (m, 1H), 1.16 (d, J=8.8 Hz, 3H).

Structural assignment was made by comparison of the 1H-NMR spectrum of trans-(1-benzyl-5-methylpyrrolidin-3-yl)methanol derived as described above from intermediate 17 with that reported the same compound in U.S. Pat. No. 7,649,001, example 21.

Intermediate 18

Synthesis of cis-1-((5-methylpyrrolidin-3-yl)methyl)-5-(1-(tetrahydro-2H-pyran-2-yl)-1H-pyrazol-4-yl)-1H-indole

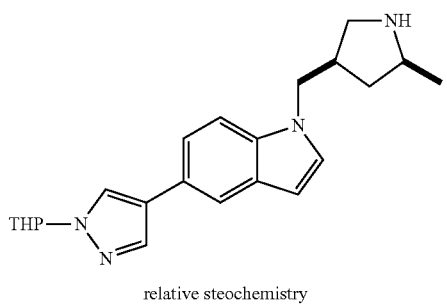

relative steochemistry

Step 1. Synthesis of cis-1-((1-benzyl-5-methylpyrrolidin-3-yl)methyl)-5-(1-(tetrahydro-2H-pyran-2-yl)-1H-pyrazol-4-yl)-1H-indole.

Sodium hydride (60% suspension in mineral oil, 50 mg, 2.08 mmol, 1.5 eq) was added to DMF (10 mL) followed by addition of 5-(1-(tetrahydro-2H-pyran-2-yl)-1H-pyrazol-4-yl)-1H-indole (0.372 g, 1.39 mmol, 1.0 eq) and the mixture was stirred at room temperature for 30 min. Cis-1-benzyl-5-methylpyrrolidin-3-yl)methyl 4-methylbenzenesulfonate (0.6 g, 1.67 mmol, 1.2 eq) was added to the above mixture and stirring continued at room temperature for 3 h. After completion of the reaction (monitored by TLC, 50% ethyl acetate-hexanes R$_f$=0.55), ice cubes were added followed by water (10 mL) and the mixture was extracted with ethyl acetate (25 mL). The organic extract was washed with water followed by brine, dried over sodium sulfate, filtered and concentrated. The crude product was purified by column chromatography on silica gel, 100-200 mesh, eluting with 30% ethyl acetate in hexanes to afford cis-1-((1-benzyl-5-methylpyrrolidin-3-yl)methyl)-5-(1-(tetrahydro-2H-pyran-2-yl)-1H-pyrazol-4-yl)-1H-indole (0.5 g, 75%) as a gummy liquid. LC-MS purity: 97.33%; (ES$^+$): m/z 455.27 (M+H$^+$), tr=1.64.

Step 2. Synthesis of cis-1-((5-methylpyrrolidin-3-yl)methyl)-5-(1-(tetrahydro-2H-pyran-2-yl)-1H-pyrazol-4-yl)-1H-indole.

To a solution of cis-1-((1-benzyl-5-methylpyrrolidin-3-yl)methyl)-5-(1-(tetrahydro-2H-pyran-2-yl)-1H-pyrazol-4-yl)-1H-indole (0.5 g, 1.1 mmol, 1.0 eq) in methanol (25 mL), was added Pd(OH)$_2$ on carbon (20% w/w, 50% moisture, 0.045 g) followed by ammonium formate (0.277 g, 4.4 mmol, 4.0 eq) at room temperature and the mixture was refluxed for 3 h. After completion of the reaction (monitored by TLC, 100% ethyl acetate R$_f$=0.1), the mixture was cooled to room temperature, the catalyst was removed by filtration through a celite bed and the filtrate was concentrated under reduced pressure to afford cis-1-((5-methylpyrrolidin-3-yl)methyl)-5-(1-(tetrahydro-2H-pyran-2-yl)-1H-pyrazol-4-yl)-1H-indole (0.4 g, 99%) as an off white solid. LC-MS purity: 94.84%, (ES$^+$): m/z 365.1 (M+H$^+$). tr=1.41.

Intermediate 19

Synthesis of rac.-trans-1-((5-methylpyrrolidin-3-yl)methyl)-5-(1-(tetrahydro-2H-pyran-2-yl)-1H-pyrazol-4-yl)-1H-indole

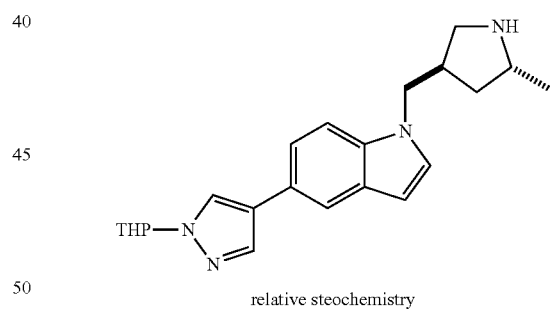

relative steochemistry

Step 1. Synthesis of rac.-trans-1-((1-benzyl-5-methylpyrrolidin-3-yl)methyl)-5-(1-(tetrahydro-2H-pyran-2-yl)-1H-pyrazol-4-yl)-1H-indole.

Sodium hydride (60% suspension in mineral oil, 0.083 g, 3.48 mmol, 1.5 eq) was added to DMF (15 mL) followed by addition of 5-(1-(tetrahydro-2H-pyran-2-yl)-1H-pyrazol-4-yl)-1H-indole (0.619 g, 2.32 mmol, 1.0 eq) and the mixture was stirred at room temperature for 30 min. Rac.-trans-1-benzyl-5-methylpyrrolidin-3-yl)methyl 4-methylbenzenesulfonate (1.0 g, 2.78 mmol, 1.2 eq) was added to the above mixture and stirring was continued at room temperature for 3 h. After completion of the reaction (monitored by TLC, 50% ethyl acetate-hexanes R$_f$=0.55), ice cubes were added followed by water (10 mL) and the mixture was extracted with ethyl acetate (25 mL). The organic extract was washed with water followed by brine, dried over sodium sulfate, filtered and concentrated. The crude product was purified by column chromatography on silica gel, 100-200 mesh, eluting with a 30% ethyl acetate in hexanes to afford rac.-trans-1-((1-benzyl-5-methylpyrrolidin-3-yl)methyl)-5-(1-(tetrahydro-2H-pyran-2-yl)-1H-pyrazol-4-yl)-1H-indole (0.9 g, 88%) as a white solid. LC-MS purity: 95.01%, (ES⁺): m/z 455.27 (M+H⁺). tr=1.62.

Step 2. Synthesis of rac.-trans-1-((5-methylpyrrolidin-3-yl) methyl)-5-(1-(tetrahydro-2H-pyran-2-yl)-1H-pyrazol-4-yl)-1H-indole.

To a solution of rac.-trans-1-((1-benzyl-5-methylpyrrolidin-3-yl)methyl)-5-(1-(tetrahydro-2H-pyran-2-yl)-1H-pyrazol-4-yl)-1H-indole (1.3 g, 2.9 mmol, 1.0 eq) in methanol (25 mL), was added Pd(OH)₂ on carbon (20% w/w, 50% moisture, 0.10 g) followed by ammonium formate (0.72 g, 11.4 mmol, 4.0 eq) at room temperature and the mixture was refluxed for 3 h. After completion of the reaction (monitored by TLC, 100% ethyl acetate R_f=0.1), the mixture was cooled to room temperature, the catalyst was removed by filtering through a celite bed and the filtrate was concentrated under reduced pressure to afford trans-1-((5-methylpyrrolidin-3-yl)methyl)-5-(1-(tetrahydro-2H-pyran-2-yl)-1H-pyrazol-4-yl)-1H-indole (1.02 g, 99%) as an off white solid. LC-MS purity: 96.54%. (ES⁺): m/z 365.1 (M+H⁺). tr=1.38.

Example 1

Synthesis of 1-((1-(phenylsulfonyl)piperidin-4-yl) methyl)-5-(1-(tetrahydro-2H-pyran-2-yl)-1H-pyrazol-4-yl)-1H-indole Benzenesulfonyl chloride (0.091 g, 0.516 mmol, 1.2 eq) and triethylamine (0.289 mL, 2.06 mmol, 5 eq) were added to a stirred solution of 1-(piperidin-4-ylmethyl)-5-(1-(tetrahydro-2H-pyran-2-yl)-1H-pyrazol-4-yl)-1H-indole (0.150 g 0.411 mmol, 1.0 eq) in dichloromethane (10 mL) at 0° C. and the mixture was stirred at rt for 1 h. After completion of the reaction (monitored by TLC, 50% ethyl acetate in pet ether; R_f=0.6), crushed ice was added and the mixture was extracted with dichloromethane. The dichloromethane layer was washed with water followed by saturated solution of sodium bicarbonate. The organic extract was dried over anhydrous sodium sulphate, filtered and concentrated under reduced pressure while keeping water bath temperature below 40° C. to obtain a crude product, which was purified by column chromatography on 100-200 mesh silica gel, eluting with 50% ethyl acetate in hexanes to obtain 1-((1-(phenylsulfonyl)piperidin-4-yl)methyl)-5-(1-(tetrahydro-2H-pyran-2-yl)-1H-pyrazol-4-yl)-1H-indole (0.090 g, 43%) as a brown oil. LCMS purity: 90.54%; (ES⁺): m/z 505.16 (M+H⁺); tr=2.34 min.

Examples 2-4

Using the procedure described in example 1 and using the indicated sulfonyl chlorides the compounds shown in Table below were prepared:

| Example | Sulfonyl Chloride | Product | Yield (%) | LCMS |
|---|---|---|---|---|
| 2 | ![benzylsulfonyl chloride] | 1-((1-(benzylsulfonyl)piperidin-4-yl)methyl)-5-(1-(tetrahydro-2H-pyran-2-yl)-1H-pyrazol-4-yl)-1H-indole | 32 | Purity: 99.4% (ES⁺): m/z 519.5 (M + H⁺); tr = 2.35 min. |
| 3 | ![phenethylsulfonyl chloride] | 1-((1-(phenethylsulfonyl)piperidin-4-yl)methyl)-5-(1-(tetrahydro-2H-pyran-2-yl)-1H-pyrazol-4-yl)-1H-indole | 82 | Purity: 98.8% (ES⁺) m/z 533.27; tr = 2.39 min. |
| 4 | ![trifluoroethylsulfonyl chloride] | 5-(1-(tetrahydro-2H-pyran-2-yl)-1H-pyrazol-4-yl)-1-((1-((2,2,2-trifluoroethyl)sulfonyl)piperidin-4-yl)methyl)-1H-indole | 66 | Purity: 96.4% (ES⁺) m/z 511.27 (M + H⁺); tr = 2.28 min. |

Example 5

Synthesis of 1-((1-(phenylsulfonyl)piperidin-4-yl) methyl)-5-(1H-pyrazol-4-yl)-1H-indole

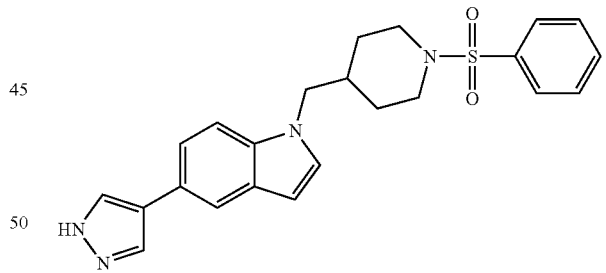

To a solution of 1-((1-(phenylsulfonyl)piperidin-4-yl) methyl)-5-(1-(tetrahydro-2H-pyran-2-yl)-1H-pyrazol-4-yl)-1H-indole (0.090 g, 0.18 mmol, 1 eq) in MeOH (10 mL, 10 vol) was added p-toluenesulfonic acid (0.153 g, 0.891 mmol, 5 eq) at room temperature and the mixture was stirred for 6 h. After completion of reaction (monitored by TLC, 50% ethyl acetate in pet ether, R_f=0.5), methanol was removed under reduced pressure, chilled water was added and the pH adjusted to 7 with saturated aqueous NaHCO₃. The mixture was extracted with ethyl acetate, the ethyl acetate layer was washed with water followed by brine, dried over anhydrous sodium sulphate, filtered and concentrated under reduced pressure. The crude product was triturated in diethyl ether to afford 1-((1-(phenylsulfonyl)piperidin-4-yl)methyl)-5-(1H- pyrazol-4-yl)-1H-indole (0.044 g, 59%) as an off white solid. LCMS: purity 96.10%; (ES⁺) m/z: 421.33 (M+H⁺); tr=3.78 min. ¹H NMR (DMSO-d$_6$, 400 MHz) δ 12.77 (s, 1H), 8.07 (s, 1H), 7.84 (s, 1H), 7.71-7.67 (m, 4H), 7.63-7.59 (m, 2H), 7.42 (d, J=8.4 Hz, 1H), 7.33 (d, J=8.4 Hz, 1H), 7.26 (d, J=3.6 Hz, 1H), 6.37 (d, J=2.8 Hz, 1H), 4.02 (d, J=7.2 Hz, 2H), 3.63 (d, J=12.4 Hz, 2H), 2.13 (t, J=10.4 Hz, 2H), 1.85-1.75 (m, 1H), 1.51 (d, J=11.6 Hz, 2H), 1.34-1.26 (m, 2H).

Examples 6-8

Using the procedure described in Example 4 and the indicated starting materials, the compounds shown in the table below were prepared:

| Example | Starting Material from Example | Compound | Yield (%) | LCMS ¹H NMR (DMSO-d$_6$, 400 MHz) δ |
|---|---|---|---|---|
| 6 | 2 | 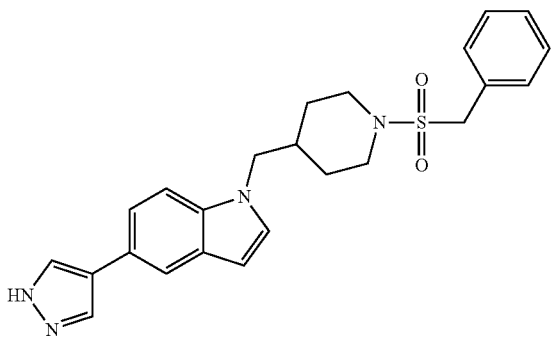 [SMILES: O=S(=O)(Cc1ccccc1)N1CCC(Cn2ccc3cc(-c4cn[nH]c4)ccc32)CC1]<br>1-((1-(benzylsulfonyl)piperidin-4-yl)methyl)-5-(1H-pyrazol-4-yl)-1H-indole | 63 | LCMS: Purity: 97.33%; (ES⁺): m/z 435.14 (M + H⁺); tr = 2.69 min. ¹H NMR (DMSO-d$_6$, 400 MHz) δ 12.78 (s, 1H), 8.08 (bs, 1H), 7.88 (bs, 1H), 7.73 (s, 1H), 7.48 (d, J = 8.8 Hz, 1H), 7.38-7.30 (m, 7H), 6.39 (d, J = 1.8 Hz, 1H), 4.34 (s, 2H), 4.06 (d, J = 6.8 Hz, 2H), 3.53 (d, J = 12.0 Hz, 2H), 2.64 (t, J = 11.2 Hz, 2H), 1.97-1.88 (m, 1H), 1.47 (d, J = 11.2 Hz, 2H), 1.24-1.14 (m, 2H). |
| 7 | 3 | 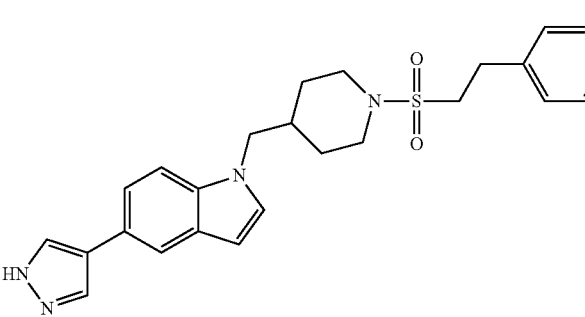<br>1-((1-(phenethylsulfonyl)piperidin-4-yl)methyl)-5-(1H-pyrazol-4-yl)-1H-indole | 53 | LCMS: Purity: 99.46%; (ES⁺): m/z 449.30 (M + H⁺); tr = 3.89 min. ¹H NMR (DMSO-d$_6$, 400 MHz) δ 12.78 (s, 1H), 8.06 (bs, 1H), 7.89 (bs, 1H), 7.73 (s, 1H), 7.49 (d, J = 8.4 Hz, 1H), 7.37 (dd, J = 7.6 Hz & 1.2 Hz, 1H), 7.32-7.25 (m, 5H), 7.23-7.19 (m, 1H), 6.39 (d, J = 2.8 Hz, 1H), 4.09 (d, J = 6.8 Hz, 2H), 3.59 (d, J = 12.4 Hz, 2H), 3.29-3.25 (m, 2H), 2.97-2.92 (m, 2H), 2.73 (t, J = 12.0 Hz, 2H), 1.99-1.90 (m, 1H), 1.53 (d, J = 10.4 Hz, 2H), 1.30-1.20 (m, 2H). |
| 8 | 4 | 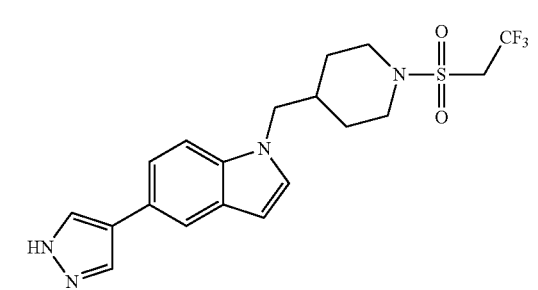 [SMILES: O=S(=O)(CC(F)(F)F)N1CCC(Cn2ccc3cc(-c4cn[nH]c4)ccc32)CC1]<br>5-(1H-pyrazol-4-yl)-1-((1-((2,2,2-trifluoroethyl)sulfonyl)piper-idin-4-yl)methyl)-1H-indole | 73 | LCMS: Purity: 96.33%; (ES⁺): m/z 427.27 (M + H⁺); tr = 3.69 min. ¹H NMR (DMSO-d$_6$, 400 MHz) δ 12.79 (s, 1H), 8.08 (bs, 1H), 7.87 (bs, 1H), 7.74 (s, 1H), 7.50 (d, J = 8.8 Hz, 1H), 7.37 (dd, J = 7.2 Hz, & 1.6 Hz, 1H), 7.32 (d, J = 2.8 Hz, 1H), 6.40 (d, J = 2.8 Hz, 1H), 4.43 (q, J = 10.4 Hz, 2H), 4.10 (d, J = 7.2 Hz, 2H), 3.64 (d, J = 12.0 Hz, 2H), 2.77 (t, J = 12.0 Hz, 2H), 2.00-1.92 (m, 1H), 1.55 (d, J = 10.8 Hz, 2H), 1.33-1.24 (m, 2H). |

Examples 9-12

Using the methods described in examples 1 and 5, and starting with 1-(pyrrolidin-3-ylmethyl)-5-(1-(tetrahydro-2H-pyran-2-yl)-1H-pyrazol-4-yl)-1H-indole and the sulfonyl chlorides shown in the table below, the following can be prepared:

| Example | Sulfonyl Chloride | Product |
|---|---|---|
| 9 | (benzenesulfonyl chloride) | 1-((1-(phenylsulfonyl)pyrrolidin-3-yl)methyl)-5-(1H-pyrazol-4-yl)-1H-indole |
| 10 | (phenylmethanesulfonyl chloride) | 1-((1-(benzylsulfonyl)pyrrolidin-3-yl)methyl)-5-(1H-pyrazol-4-yl)-1H-indole |
| 11 | (2-phenylethanesulfonyl chloride) | 1-((1-(phenethylsulfonyl)pyrrolidin-3-yl)methyl)-5-(1H-pyrazol-4-yl)-1H-indole |
| 12 | (tert-butylsulfonyl chloride) | 1-((1-(tert-butylsulfonyl)pyrrolidin-3-yl)methyl)-5-(1H-pyrazol-4-yl)-1H-indole |

Example 13-16

Using the methods described in examples 1 and 5, and starting with 1-((5-methylpyrrolidin-3-yl)methyl)-5-(1-(tetrahydro-2H-pyran-2-yl)-1H-pyrazol-4-yl)-1H-indole and the sulfonyl chlorides shown in the table below, the following can be prepared:

| Example | Sulfonyl Chloride | Product |
|---|---|---|
| 13 | benzenesulfonyl chloride | 1-((5-methyl-1-(phenylsulfonyl)pyrrolidin-3-yl)methyl)-5-(1H-pyrazol-4-yl)-1H-indole |
| 14 | phenylmethanesulfonyl chloride | 1-((1-(benzylsulfonyl)-5-methylpyrrolidin-3-yl)methyl)-5-(1H-pyrazol-4-yl)-1H-indole |
| 15 | 2-phenylethanesulfonyl chloride | 1-((5-methyl-1-(phenethylsulfonyl)pyrrolidin-3-yl)methyl)-5-(1H-pyrazol-4-yl)-1H-indole |
| 16 | tert-butylsulfonyl chloride | 1-((1-(tert-butylsulfonyl)-5-methylpyrrolidin-3-yl)methyl)-5-(1H-pyrazol-4-yl)-1H-indole |

Examples 17-20

Using the methods described in examples 1 and 5, and starting with 1-(azepan-4-ylmethyl)-5-(1-(tetrahydro-2H-pyran-2-yl)-1H-pyrazol-4-yl)-1H-indole and the sulfonyl chlorides shown in the table below, the following can be prepared:

| Example | Sulfonyl Chloride | Product |
|---|---|---|
| 17 | (benzenesulfonyl chloride) | 1-((1-(phenylsulfonyl)azepan-4-yl)methyl)-5-(1H-pyrazol-4-yl)-1H-indole |
| 18 | (phenylmethanesulfonyl chloride) | 1-((1-(benzylsulfonyl)azepan-4-yl)methyl)-5-(1H-pyrazol-4-yl)-1H-indole |
| 19 | (2-phenylethanesulfonyl chloride) | 1-((1-(phenethylsulfonyl)azepan-4-yl)methyl)-5-(1H-pyrazol-4-yl)-1H-indole |

-continued

| Example | Sulfonyl Chloride | Product |
|---|---|---|
| 20 | (tert-butylsulfonyl chloride) | 1-((1-(tert-butylsulfonyl)azepan-4-yl)methyl)-5-(1H-pyrazol-4-yl)-1H-indole |

Examples 21-24

Using the methods described in examples 1 and 5, and starting with 1-(7-azabicyclo[2.2.1]heptan-2-ylmethyl)-5-(1-(tetrahydro-2H-pyran-2-yl)-1H-pyrazol-4-yl)-1H-indole and the sulfonyl chlorides shown in the table below, the following can be prepared:

| Example | Sulfonyl Chloride | Product |
|---|---|---|
| 21 | (benzenesulfonyl chloride) | 1-((7-(phenylsulfonyl)-7-azabicyclo[2.2.1]heptan-2-yl)methyl)-5-(1H-pyrazol-4-yl)-1H-indole |
| 22 | (phenylmethanesulfonyl chloride) | 1-((7-(benzylsulfonyl)-7-azabicyclo[2.2.1]heptan-2-yl)methyl)-5-(1H-pyrazol-4-yl)-1H-indole |

-continued

| Example | Sulfonyl Chloride | Product |
|---------|-------------------|---------|
| 23 | phenethylsulfonyl chloride | 1-((7-(phenethylsulfonyl)-7-azabicyclo[2.2.1]heptan-2-yl)methyl)-5-(1H-pyrazol-4-yl)-1H-indole |
| 24 | tert-butylsulfonyl chloride | 1-((7-(tert-butylsulfonyl)-7-azabicyclo[2.2.1]heptan-2-yl)methyl)-5-(1H-pyrazol-4-yl)-1H-indole |

Examples 25-28

Using the methods described in examples 1 and 5, and starting with 1-(piperidin-4-ylmethyl)-6-(1-(tetrahydro-2H-pyran-2-yl)-1H-pyrazol-4-yl)-1,2,3,4-tetrahydroquinoline and the sulfonyl chlorides shown in the table below, the following can be prepared:

| Example | Sulfonyl Chloride | Product |
|---------|-------------------|---------|
| 25 | phenylsulfonyl chloride | 1-((1-(phenylsulfonyl)piperidin-4-yl)methyl)-6-(1H-pyrazol-4-yl)-1,2,3,4-tetrahydroquinoline |

-continued

| Example | Sulfonyl Chloride | Product |
| --- | --- | --- |
| 26 | benzylsulfonyl chloride | 1-((1-(benzylsulfonyl)piperidin-4-yl)methyl)-6-(1H-pyrazol-4-yl)-1,2,3,4-tetrahydroquinoline |
| 27 | phenethylsulfonyl chloride | 1-((1-(phenethylsulfonyl)piperidin-4-yl)methyl)-6-(1H-pyrazol-4-yl)-1,2,3,4-tetrahydroquinoline |
| 28 | tert-butylsulfonyl chloride | 1-((1-(tert-butylsulfonyl)piperidin-4-yl)methyl)-6-(1H-pyrazol-4-yl)-1,2,3,4-tetrahydroquinoline |

Example 29

Synthesis of 1-((5,5-dimethyl-1-(phenylsulfonyl)pyrrolidin-3-yl)methyl)-5-(1H-pyrazol-4-yl)-1H-indole

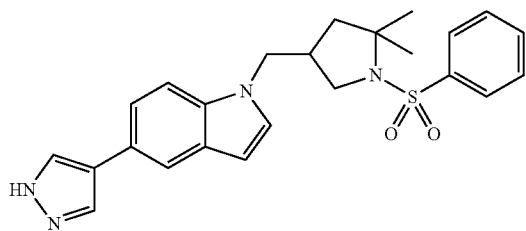 [SMILES: CC1(C)CC(Cn2ccc3cc(-c4cn[nH]c4)ccc32)CN1S(=O)(=O)c1ccccc1]

Step 1. Synthesis of 1-((5,5-dimethyl-1-(phenylsulfonyl)pyrrolidin-3-yl)methyl)-5-(1-(tetrahydro-2H-pyran-2-yl)-1H-pyrazol-4-yl)-1H-indole.

Triethylamine (0.3 ml, 3.3 mmol) was slowly added to a solution of 1-((5,5-dimethylpyrrolidin-3-yl)methyl)-5-(1-(tetrahydro-2H-pyran-2-yl)-1H-pyrazol-4-yl)-1H-indole (0.250 g, 0.66 mmol) in dichloromethane (10 mL), at 0° C. followed by benzenesulfonyl chloride (0.139 g, 0.79 mmol) and the mixture was allowed to stir at room temperature for 2 h. After completion of the reaction (monitored by TLC, 70% ethyl acetate-hexanes, $R_f$=0.4), saturated aqueous sodium bicarbonate was added and the mixture was extracted with dichloromethane. The organic extract was dried over anhydrous sodium sulfate, filtered and concentrated under reduced pressure to obtain a crude product, which was purified by column chromatography on neutral alumina, using 55% ethyl acetate-hexanes as eluent to afford of 1-((5,5-dimethyl-1-(phenylsulfonyl)pyrrolidin-3-yl)methyl)-5-(1-(tetrahydro-2H-pyran-2-yl)-1H-pyrazol-4-yl)-1H-indole (0.230 g, 67%) as an off white solid. LC-MS purity: 97.34%. (ES$^+$): m/z 519.5 (M+H$^+$), tr=2.38 min.

Step 2. Synthesis of 1-((5,5-dimethyl-1-(phenylsulfonyl)pyrrolidin-3-yl)methyl)-5-(1H-pyrazol-4-yl)-1H-indole.

To a solution of 1-((5,5-dimethyl-1-(phenylsulfonyl)pyrrolidin-3-yl)methyl)-5-(1-(tetrahydro-2H-pyran-2-yl)-1H-pyrazol-4-yl)-1H-indole (0.230 g, 0.44 mmol) in methanol (5 mL), p-toluenesulfonic acid (0.421 g, 2.22 mmol) was added and the mixture was stirred at room temperature for 6 h. After completion of the reaction (monitored by TLC, 10% methanol in dichloromethane, $R_f$=0.5), saturated aqueous sodium bicarbonate was added and the mixture was extracted with ethyl acetate. The organic extract was dried over anhydrous sodium sulfate, filtered and concentrated. The crude product was triturated with diethyl ether to obtain 1-((5,5-dimethyl-1-(phenylsulfonyl)pyrrolidin-3-yl)methyl)-5-(1H-pyrazol-4-yl)-1H-indole (0.120 g, 61%) as a white solid. LC-MS purity: 97.59%; (ES$^+$): m/z 435.50 (M+H$^+$); tr=2.13 min. $^1$H NMR (400 MHz, DMSO-d$_6$) δ 12.80 (bs, 1H), 8.09 (s, 1H), 7.86 (bs, 1H), 7.77 (d, J=7.6 Hz, 2H), 7.73 (d, J=1.2 Hz, 1H), 7.54-7.69 (m, 3H), 7.49 (d, J=8.4 Hz, 1H), 7.37 (dd, J=8.4 Hz, 1.2 Hz, 1H), 7.30 (d, J=2.8 Hz, 1H), 6.38 (d, J=2.8 Hz, 1H), 4.09-4.26 (m, 2H), 3.41-3.50 (m, 1H), 3.02-3.12 (m, 1H), 2.65-2.81 (m, 1H), 1.60-1.78 (m, 2H), 1.36 (s, 3H), 1.26 (s, 3H).

Examples 30-32

Using the method described in example 29 and starting with 1-((5,5-dimethylpyrrolidin-3-yl)methyl)-5-(1-(tetrahydro-2H-pyran-2-yl)-1H-pyrazol-4-yl)-1H-indole and the sulfonyl chlorides shown in the table below, the following can be prepared:

| Example | Sulfonyl Chloride | Product |
|---|---|---|
| 30 | ![benzylsulfonyl chloride] | ![product 30] <br> 1-((1-(benzylsulfonyl)-5,5-dimethylpyrrolidin-3-yl)methyl)-5-(1H-pyrazol-4-yl)-1H-indole |
| 31 | ![phenethylsulfonyl chloride] | ![product 31] <br> 1-((5,5-dimethyl-1-(phenethylsulfonyl)pyrrolidin-3-yl)methyl)-5-(1H-pyrazol-4-yl)-1H-indole |

| Example | Sulfonyl Chloride | Product |
|---|---|---|
| 32 | 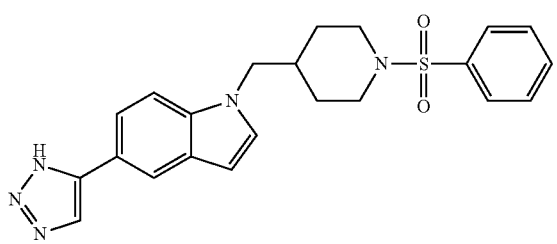 [SMILES: O=S(=O)(c1ccccc1)N1CCC(Cn2ccc3cc(-c4cnn[nH]4)ccc32)CC1] | 1-((1-(tert-butylsulfonyl)-5,5-dimethylpyrrolidin-3-yl)methyl)-5-(1H-pyrazol-4-yl)-1H-indole |

Example 33

1-((1-(phenylsulfonyl)piperidin-4-yl)methyl)-5-(1H-1,2,3-triazol-5-yl)-1H-indole

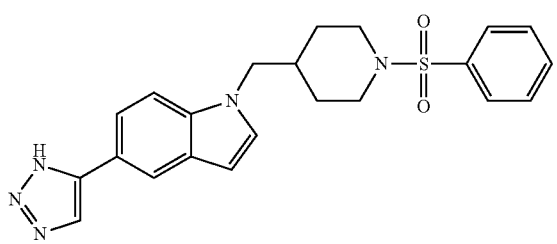 [SMILES: O=S(=O)(c1ccccc1)N1CCC(Cn2ccc3cc(-c4cnn[nH]4)ccc32)CC1]

The title compound can be prepared from 5-ethynyl-1-((1-(phenylsulfonyl)piperidin-4-yl)methyl)-1H-indole by treatment of a dichloromethane solution with a solution of sodium ascorbate (1.0 eq), CuSO$_4$.5H$_2$O (0.05 eq) and sodium azide (2.0 eq) in a mixture of DMSO and water (1:1) at room temperature for 18 h. After quenching with water, extraction with ethyl acetate, drying and concentration, the crude product can be purified by column chromatography over silica gel.

Example 34

1-((1-(phenylethylsulfonyl)piperidin-4-yl)methyl)-5-(1H-1,2,3-triazol-5-yl)-1H-indole

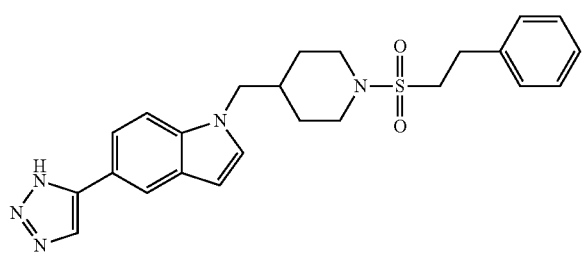 [SMILES: O=S(=O)(CCc1ccccc1)N1CCC(Cn2ccc3cc(-c4cnn[nH]4)ccc32)CC1]

1-((1-(Phenylethylsulfonyl)piperidin-4-yl)methyl)-5-(1H-1,2,3-triazol-5-yl)-1H-indole can be prepared from 5-ethynyl-1-((1-(phenylethylsulfonyl)piperidin-4-yl)methyl)-1H-indole by treatment of a dichloromethane solution with a solution of sodium ascorbate (1.0 eq), CuSO$_4$.5H$_2$O (0.05 eq) and sodium azide (2.0 eq) in a mixture of DMSO and water (1:1) at room temperature for 18 h. After quenching with water, extraction with ethyl acetate, drying and concentration, the crude product can be purified by column chromatography over silica gel.

Example 35

Synthesis of 1-((1-(4-chlorophenylsulfonyl)piperidin-4-yl)methyl)-5-(1-(tetrahydro-2H-pyran-2-yl)-1H-pyrazol-4-yl)-1H-indole

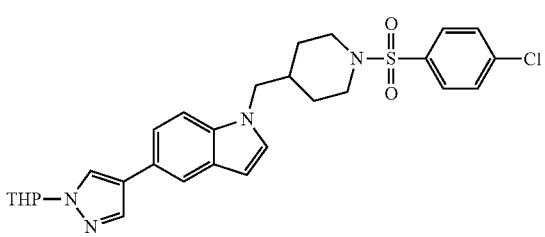

4-chlorobenzene-1-sulfonyl chloride (0.104 g, 0.495 mmol, 1.2 eq) and triethylamine (0.30 mL, 2.06 mmol, 5.0 eq) were added to a stirred solution of 1-(piperidin-4-ylmethyl)-5-(1-(tetrahydro-2H-pyran-2-yl)-1H-pyrazol-4-yl)-1H-indole (0.150 g 0.41 mmol, 1.0 eq) in dichloromethane (5 mL) at 0° C. and the mixture was stirred at room temperature for 6 h. After completion of the reaction (monitored by TLC, 5% MeOH in dichloromethane; R$_f$=0.45), chilled water was added and the mixture was extracted with dichloromethane. The organic extract was dried over anhydrous sodium sulfate, filtered and concentrated under reduced pressure. The crude product was purified by column chromatography on silica gel, 100-200 mesh, eluting with a 70-80% gradient of ethyl acetate in hexanes to afford 1-((1-(4-chlorophenylsulfonyl)piperidin-4-yl)methyl)-5-(1-(tetrahydro-2H-pyran-2-yl)-1H-pyrazol-4-yl)-1H-indole, (0.160 g, 72%) as viscous liquid. LCMS purity: 97.06%; (ES$^+$): m/z 539.16 (M+H$^+$); tr=2.43 min.

Example 36

Synthesis of 1-((1-(4-chlorophenylsulfonyl)piperidin-4-yl)methyl)-5-(1H-pyrazol-4-yl)-1H-indole

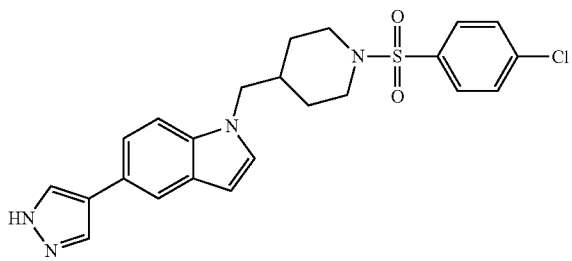 [SMILES: O=S(=O)(c1ccc(Cl)cc1)N1CCC(Cn2ccc3cc(-c4cn[nH]c4)ccc32)CC1]

To a solution of 1-((1-(4-chlorophenylsulfonyl)piperidin-4-yl)methyl)-5-(1-(tetrahydro-2H-pyran-2-yl)-1H-pyrazol-4-yl)-1H-indole (0.160 g, 0.296 mmol, 1.0 eq) in MeOH (5 mL) was added p-toluenesulfonic acid mono hydrate (0.282 g, 1.484 mmol, 5.0 eq) at room temperature and the mixture was stirred at room temperature for 12 h. After completion of reaction (monitored by TLC, 5% methanol in dichloromethane $R_f$=0.35), methanol was removed under reduced pressure, chilled water was added and the pH adjusted to 7 with saturated aqueous NaHCO$_3$. The mixture was then extracted with ethyl acetate, the ethyl acetate layer was washed with water followed by brine, dried over anhydrous sodium sulfate, filtered and concentrated under reduced pressure. The crude product was triturated with diethyl ether to obtain 1-((1-(4-chlorophenylsulfonyl)piperidin-4-yl)methyl)-5-(1H-pyrazol-4-yl)-1H-indole (0.110 g, 82%) as a light pink solid. LC-MS: Purity 97.27%; (ES$^+$): m/z 455.06 (M+H$^+$); tr=2.19 min. $^1$H NMR (400 MHz, DMSO-d$_6$) δ 12.77 (brs, 1H), 8.07 (s, 1H), 7.85 (s, 1H), 7.71-7.66 (m, 5H), 7.42 (d, J=8.8 Hz, 1H), 7.34-7.25 (m, 1H), 7.26 (d, J=2.8 Hz, 1H), 6.36 (d, J=2.8 Hz, 1H), 4.03 (d, J=7.2 Hz, 2H), 3.62 (d, J=12 Hz, 2H), 2.18 (t, J=11.2 Hz, 2H), 1.88-1.79 (m, 1H), 1.51 (d, J=11.6 Hz, 2H), 1.32-1.23 (m, 2H).

Example 37

Synthesis 1-((1-(pyridin-3-ylsulfonyl)piperidin-4-yl)methyl)-5-(1-(tetrahydro-2H-pyran-2-yl)-1H-pyrazol-4-yl)-1H-indole

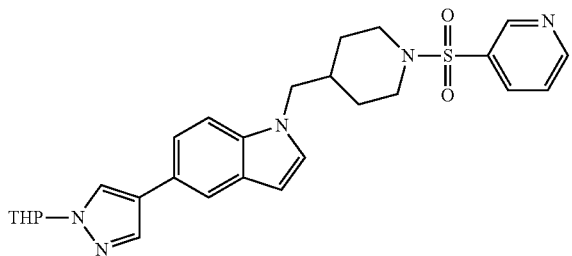

Pyridine-3-sulfonyl chloride (0.073 g, 0.618 mmol, 1.5 eq) and triethylamine (0.280 mL, 2.06 mmol, 5.0 eq) were added to a stirred solution of 1-(piperidin-4-ylmethyl)-5-(1-(tetrahydro-2H-pyran-2-yl)-1H-pyrazol-4-yl)-1H-indole (0.150 g 0.412 mmol, 1.0 eq) in dichloromethane (10 mL) at 0° C. and the mixture was stirred at room temperature for 6 h. After completion of the reaction (monitored by TLC, 5% MeOH in dichloromethane; $R_f$=0.40), chilled water was added and the mixture was extracted with dichloromethane. The organic extract was dried over anhydrous sodium sulfate, filtered and concentrated under reduced pressure. The crude product was purified by column chromatography on silica gel, 100-200 mesh, eluting with a 75-80% gradient of ethyl acetate in hexanes to afford 1-((1-(pyridin-3-ylsulfonyl)piperidin-4-yl)methyl)-5-(1-(tetrahydro-2H-pyran-2-yl)-1H-pyrazol-4-yl)-1H-indole (0.200 g, 96%) as pale yellow solid. LCMS purity: 95.1%; (ES$^+$): m/z 506.23 (M+H$^+$); tr=2.16 min.

Example 38

Synthesis of 5-(1H-pyrazol-4-yl)-1-((1-(pyridin-3-ylsulfonyl)piperidin-4-yl)methyl)-1H-indole

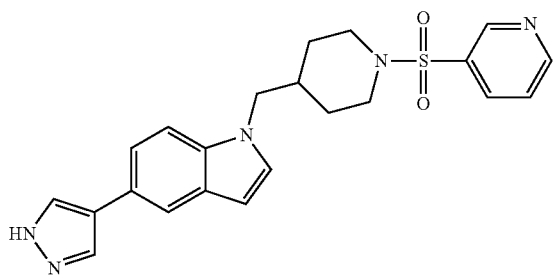 [SMILES: O=S(=O)(c1cccnc1)N1CCC(Cn2ccc3cc(-c4cn[nH]c4)ccc32)CC1]

To a solution of 1-((1-(pyridin-3-ylsulfonyl)piperidin-4-yl)methyl)-5-(1-(tetrahydro-2H-pyran-2-yl)-1H-pyrazol-4-yl)-1H-indole (200 g, 0.396 mmol, 1.0 eq) in MeOH (5 mL) was added p-toluenesulfonic acid mono hydrate (0.376 g, 1.98 mmol, 5.0 eq) at room temperature and the mixture was stirred at room temperature for 12 h. After completion of reaction (monitored by TLC, 5% methanol in dichloromethane $R_f$=0.35), methanol was removed under reduced pressure, chilled water was added and the pH adjusted to 7 with saturated aqueous NaHCO$_3$. The mixture was then extracted with ethyl acetate, the ethyl acetate layer was washed with water followed by brine, dried over anhydrous sodium sulfate, filtered and concentrated under reduced pressure. The crude product was triturated with diethyl ether to afford 5-(1H-pyrazol-4-yl)-1-((1-(pyridin-3-ylsulfonyl)piperidin-4-yl)methyl)-1H-indole (0.140 g, 83%) as a pale yellow solid. LC-MS: Purity 97.6%; (ES$^+$): m/z 422.14 (M+H$^+$); tr=2.37 min. $^1$H NMR (400 MHz, DMSO-d$_6$) δ 12.77 (brs, 1H), 8.62 (m, 2H), 8.12-8.06 (m, 2H), 7.85 (s, 1H), 7.71-7.63 (m, 2H), 7.42 (d, J=8.4 Hz, 1H), 7.33 (d, J=8.4 Hz, 1H), 7.26 (d, J=2.8 Hz, 1H), 6.36 (d, J=2.8 Hz, 1H), 4.04 (d, J=7.6 Hz, 2H), 3.67 (d, J=11.6 Hz, 2H), 2.24 (t, J=11.8 Hz, 2H), 1.89-1.80 (m, 1H), 1.53 (d, J=11.6 Hz, 2H), 1.31-1.22 (m, 2H).

Example 39

Synthesis of 1-((1-(2-fluorophenylsulfonyl)piperidin-4-yl)methyl)-5-(1-(tetrahydro-2H-pyran-2-yl)-1H-pyrazol-4-yl)-1H-indole

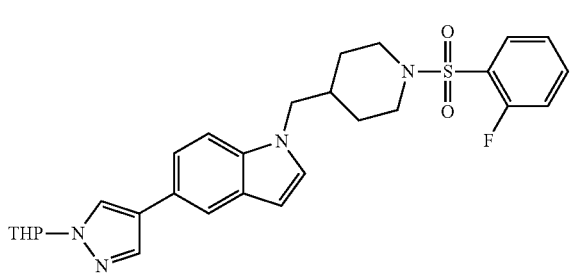

2-Fluorobenzene-1-sulfonyl chloride (0.088 mL, 0.66 mmol, 1.2 eq) and triethylamine (0.374 mL, 2.74 mmol, 5.0 eq) were added to a stirred solution of 1-(piperidin-4-ylmethyl)-5-(1-(tetrahydro-2H-pyran-2-yl)-1H-pyrazol-4-yl)-1H-indole (0.2 g, 0.55 mmol, 1.0 eq) in dichloromethane (10 mL) at 0° C. and the mixture was stirred at room temperature for 6 h. After completion of the reaction (monitored by TLC, 5% MeOH in dichloromethane; $R_f$=0.40), chilled water was added and the mixture was extracted with dichloromethane. The organic extract was dried over anhydrous sodium sulfate, filtered and concentrated under reduced pressure. The crude product was purified by column chromatography on silica gel, 100-200 mesh, eluting with a 80-85% gradient of ethyl acetate in hexanes to afford 1-((1-(2-fluorophenylsulfonyl)piperidin-4-yl)methyl)-5-(1-(tetrahydro-2H-pyran-2-yl)-1H-pyrazol-4-yl)-1H-indole (0.180, 63%) as viscous liquid. LCMS purity: 98.8% (ES$^+$): m/z 523.50 (M+H$^+$); tr=2.36 min.

Example 40

Synthesis of 1-((1-(2-fluorophenylsulfonyl)piperidin-4-yl)methyl)-5-(1H-pyrazol-4-yl)-1H-indole

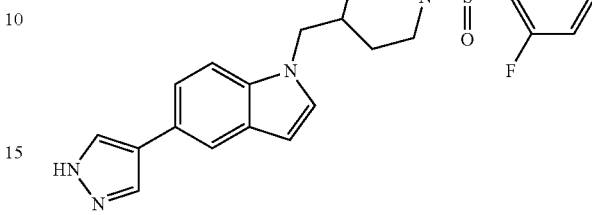

To a solution of 1-((1-(2-fluorophenylsulfonyl)piperidin-4-yl)methyl)-5-(1-(tetrahydro-2H-pyran-2-yl)-1H-pyrazol-4-yl)-1H-indole (0.180 g, 0.345 mmol, 1.0 eq) in MeOH (5 mL) was added p-toluenesulfonic acid mono hydrate (0.327 g, 1.72 mmol, 5.0 eq) at room temperature and the mixture was stirred at room temperature for 12 h. After completion of the reaction (monitored by TLC, 5% methanol in dichloromethane $R_f$=0.35), methanol was removed under reduced pressure, chilled water was added and the pH adjusted to 7 with saturated aqueous NaHCO$_3$. The mixture was then extracted with ethyl acetate, the ethyl acetate layer was washed with water followed by brine, dried over anhydrous sodium sulfate, filtered and concentrated under reduced pressure. The crude product was triturated with diethyl ether to afford 1-((1-(2-fluorophenylsulfonyl)piperidin-4-yl)methyl)-5-(1H-pyrazol-4-yl)-1H-indole (0.115 g, 76%) as a white solid. LC-MS: Purity 96.96%; (ES$^+$): m/z 439.40 (M+H$^+$); tr=2.10 min. $^1$H NMR (400 MHz, DMSO-d$_6$) δ 12.77 (brs, 1H), 8.07 (s, 1H), 7.85 (s, 1H), 7.76-7.70 (m, 3H), 7.47-7.34 (m, 4H), 7.27 (d, J=3.2 Hz, 1H), 6.36 (d, J=2.8 Hz, 1H), 4.04 (d, J=7.2 Hz, 2H), 3.67 (d, J=12.4 Hz, 2H), 2.43 (d, J=12.4 Hz, 2H), 1.95-1.85 (m, 1H), 1.53 (d, J=12.0 Hz, 2H), 1.31-1.22 (m, 2H).

Examples 41-46

Using the methods described in examples 1 and 5, and starting with 1-(piperidin-4-ylmethyl)-6-(1-(tetrahydro-2H-pyran-2-yl)-1H-pyrazol-4-yl)-1,2,3,4-tetrahydroquinoline and the sulfonyl chlorides shown in the table below, the following can be prepared:

| Example | Sulfonyl Chloride | Product |
|---|---|---|
| 41 | ![](sulfonyl chloride with m-tolyl) | 5-(1H-pyrazol-4-yl)-1-((1-(m-tolylsulfonyl)piperidin-4-yl)methyl)-1H-indole |

-continued

| Example | Sulfonyl Chloride | Product |
|---|---|---|
| 42 | 4-methoxybenzenesulfonyl chloride | 1-((1-((4-methoxyphenyl)sulfonyl)piperidin-4-yl)methyl)-5-(1H-pyrazol-4-yl)-1H-indole |
| 43 | 4-fluorobenzenesulfonyl chloride | 1-((1-((4-fluorophenyl)sulfonyl)piperidin-4-yl)methyl)-5-(1H-pyrazol-4-yl)-1H-indole |
| 44 | 3-fluorobenzenesulfonyl chloride | 1-((1-((3-fluorophenyl)sulfonyl)piperidin-4-yl)methyl)-5-(1H-pyrazol-4-yl)-1H-indole |
| 45 | 3-cyanobenzenesulfonyl chloride | 3-((4-((5-(1H-pyrazol-4-yl)-1H-indol-1-yl)methyl)piperidin-1-yl)sulfonyl)benzonitrile |

| Example | Sulfonyl Chloride | Product |
|---|---|---|
| 46 | Cl-S(=O)(=O)-C6H4-CHF2 | 1-((1-((4-(difluoromethyl)phenyl)sulfonyl)piperidin-4-yl)methyl)-5-(1H-pyrazol-4-yl)-1H-indole |

Example 47

Synthesis of rac.-cis-1-((-5-methyl-1-(phenylsulfonyl)pyrrolidin-3-yl)methyl)-5-(1H-pyrazol-4-yl)-1H-indole

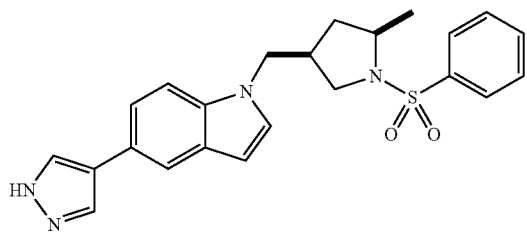

relative sterochemistry

Step 1. Synthesis of rac.-cis-1-((-5-methyl-1-(phenylsulfonyl)pyrrolidin-3-yl)methyl)-5-(1-(tetrahydro-2H-pyran-2-yl)-1H-pyrazol-4-yl)-1H-indole.

Triethylamine (0.3 ml, 3.4 mmol) was slowly added to a solution of rac.-cis-1-((-5-methylpyrrolidin-3-yl)methyl)-5-(1-(tetrahydro-2H-pyran-2-yl)-1H-pyrazol-4-yl)-1H-indole (0.250 g, 0.68 mmol) in dichloromethane (10 mL), at 0° C. followed by benzenesulfonyl chloride (0.145 g, 0.824 mmol) and the mixture was allowed to stir at room temperature for 4 h. After completion of the reaction (monitored by TLC, 70% ethyl acetate-hexanes, $R_f$=0.4), saturated aqueous sodium bicarbonate was added and the mixture was extracted with dichloromethane. The organic extract was dried over anhydrous sodium sulfate, filtered and concentrated under reduced pressure. The crude product was purified by column chromatography on neutral alumina, using 50-55% ethyl acetate-hexanes as eluent to afford rac.-cis-1-((-5-methyl-1-(phenylsulfonyl)pyrrolidin-3-yl)methyl)-5-(1-(tetrahydro-2H-pyran-2-yl)-1H-pyrazol-4-yl)-1H-indole (0.250 g, 72%) as an off white solid. LC-MS purity: 94.06%. (ES+): m/z 505.5 (M+H+), tr=2.32 min.

Step 2. Synthesis of rac.-cis 1-((-5-methyl-1-(phenylsulfonyl)pyrrolidin-3-yl)methyl)-5-(1H-pyrazol-4-yl)-1H-indole.

To a solution of rac.-cis-1-((-5-methyl-1-(phenylsulfonyl)pyrrolidin-3-yl)methyl)-5-(1-(tetrahydro-2H-pyran-2-yl)-1H-pyrazol-4-yl)-1H-indole (0.250 g, 0.49 mmol) in methanol (10 mL), p-toluenesulfonic acid (0.471 g, 2.48 mmol, 5.0 eq) was added and the mixture was stirred at room temperature for 6 h. After completion of the reaction (monitored by TLC, 10% methanol in dichloromethane, $R_f$=0.5), saturated aqueous sodium bicarbonate was added and the mixture was extracted with ethyl acetate. The organic extract was dried over anhydrous sodium sulfate, filtered and concentrated under reduced pressure. The crude product was triturated with diethyl ether to obtain rac.-cis-1-((-5-methyl-1-(phenylsulfonyl)pyrrolidin-3-yl)methyl)-5-(1H-pyrazol-4-yl)-1H-indole (0.110 g, 53%) as a white solid. LC-MS purity: 98.2%; (ES+): m/z 421.25 (M+H+); tr=2.06 min. $^1$H NMR (400 MHz, DMSO-$d_6$) δ 12.78 (bs, 1H), 8.09 (bs, 1H), 7.87 (bs, 1H), 7.63-7.78 (m, 4H), 7.55 (t, J=7.6 Hz, 2H), 7.28-7.40 (m, 2H), 7.22 (d, J=2.8 Hz, 1H), 6.37 (d, J=2.8 Hz, 1H), 5.75 (s, 1H), 4.03-4.20 (m, 2H), 3.38-3.52 (m, 1H), 3.07-3.20 (m, 1H), 1.8-2.0 (m, 2H), 1.25-1.42 (m, 4H).

Example 48

Synthesis of rac.-trans-1-((-5-methyl-1-(phenylsulfonyl)pyrrolidin-3-yl)methyl)-5-(1H-pyrazol-4-yl)-1H-indole

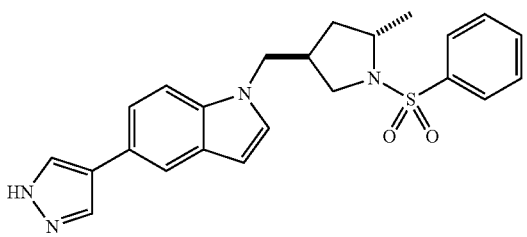

relative sterochemistry

Step 1. Synthesis of rac.-trans-1-((-5-methyl-1-(phenylsulfonyl)pyrrolidin-3-yl)methyl)-5-(1-(tetrahydro-2H-pyran-2-yl)-1H-pyrazol-4-yl)-1H-indole.

Triethylamine (0.3 ml, 3.4 mmol) was slowly added to a solution of rac.-trans-1-((-5-methylpyrrolidin-3-yl)methyl)-5-(1-(tetrahydro-2H-pyran-2-yl)-1H-pyrazol-4-yl)-1H-indole (0.250 g, 0.68 mmol) in dichloromethane (10 mL), at 0° C. followed by benzenesulfonyl chloride (0.145 g, 0.824 mmol) and the mixture was allowed to stir at room temperature for 4 h. After completion of the reaction (monitored by TLC, 70% ethyl acetate-hexanes, R$_f$=0.4), saturated aqueous sodium bicarbonate was added and the mixture was extracted with dichloromethane. The organic extract was dried over anhydrous sodium sulfate, filtered and concentrated under reduced pressure. The crude product was purified by column chromatography on neutral alumina, using 62% ethyl acetate-hexanes as eluent to afford rac.-trans-1-((-5-methyl-1-(phenylsulfonyl)pyrrolidin-3-yl)methyl)-5-(1-(tetrahydro-2H-pyran-2-yl)-1H-pyrazol-4-yl)-1H-indole (0.200 g, 24%) as an off white solid. LC-MS purity: 83.3%. (ES$^+$): m/z 505.4 (M+H$^+$), tr=2.32 min.

Step 2 Synthesis of rac.-trans-1-((-5-methyl-1-(phenylsulfonyl)pyrrolidin-3-yl)methyl)-5-(1H-pyrazol-4-yl)-1H-indole.

To a solution of rac.-trans-1-((-5-methyl-1-(phenylsulfonyl)pyrrolidin-3-yl)methyl)-5-(1-(tetrahydro-2H-pyran-2-yl)-1H-pyrazol-4-yl)-1H-indole (0.200 g, 0.40 mmol) in methanol (5 mL), p-toluenesulfonic acid (0.376 g, 1.98 mmol) was added and the mixture was stirred at room temperature for 6 h. After completion of the reaction (monitored by TLC, 10% methanol in dichloromethane, R$_f$=0.5), saturated aqueous sodium bicarbonate was added and the mixture was extracted with ethyl acetate. The organic extract was dried over anhydrous sodium sulfate, filtered and concentrated under reduced pressure. The crude product was triturated with diethyl ether to obtain rac.-trans-1-((-5-methyl-1-(phenylsulfonyl)pyrrolidin-3-yl)methyl)-5-(1H-pyrazol-4-yl)-1H-indole (0.053 g, 32%) as a white solid. LC-MS purity: 97.3%; (ES$^+$): m/z 421.24 (M+H$^+$); tr=2.06 min. $^1$H NMR (400 MHz, DMSO-d$_6$) δ 12.78 (bs, 1H), 8.08 (bs, 1H), 7.86 (bs, 1H), 7.79 (d, J=7.2 Hz, 2H), 7.65-7.76 (m, 2H), 7.58-7.67 (m, 2H), 7.30-7.42 (m, 2H), 7.21 (d, J=2.8 Hz, 1H), 6.35 (d, J=2.8 Hz, 1H), 3.98-4.08 (m, 1H), 3.68-3.87 (m, 2H), 3.35-3.42 (m, 1H), 2.86 (t, J=8.8 Hz, 1H), 2.72-2.84 (m, 1H), 1.32-1.50 (m, 2H), 1.12-1.21 (m, 3H).

Example 49

Synthesis of 1-((1-(methylsulfonyl)piperidin-4-yl)methyl)-5-(1-(tetrahydro-2H-pyran-2-yl)-1H-pyrazol-4-yl)-1H-indole

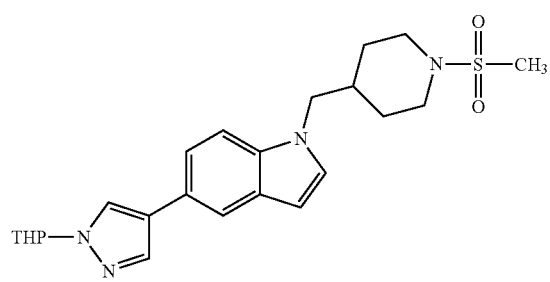

Methanesulfonyl chloride (0.047 mL, 0.66 mmol, 1.2 eq) and triethylamine (0.374 mL, 2.74 mmol, 5.0 eq) were added to a stirred solution of 1-(piperidin-4-ylmethyl)-5-(1-(tetrahydro-2H-pyran-2-yl)-1H-pyrazol-4-yl)-1H-indole (0.2 g 0.55 mmol, 1.0 eq) in dichloromethane (10 mL) at 0° C. and the mixture was stirred at room temperature for 6 h. After completion of the reaction (monitored by TLC, 5% MeOH in dichloromethane; R$_f$=0.40), chilled water was added and the mixture was extracted with dichloromethane. The organic extract was dried over anhydrous sodium sulfate, filtered and concentrated under reduced pressure. The crude product was purified by column chromatography on silica gel, 100-200 mesh, eluting with a 75-80% gradient of ethyl acetate in hexanes to afford 1-((1-(methylsulfonyl)piperidin-4-yl)methyl)-5-(1-(tetrahydro-2H-pyran-2-yl)-1H-pyrazol-4-yl)-1H-indole (0.155 g, 64%) as viscous liquid. LCMS purity: 93.32%; (ES$^+$): m/z 443.50 (M+H$^+$); tr=2.37 min.

Example 50

Synthesis of 1-((1-(methylsulfonyl)piperidin-4-yl)methyl)-5-(1H-pyrazol-4-yl)-1H-indole

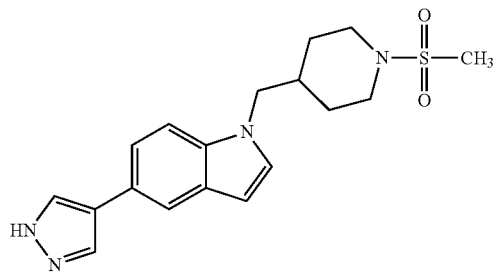 [SMILES: CS(=O)(=O)N1CCC(Cn2ccc3cc(-c4cn[nH]c4)ccc32)CC1]

To a solution of 1-((1-(methylsulfonyl)piperidin-4-yl)methyl)-5-(1-(tetrahydro-2H-pyran-2-yl)-1H-pyrazol-4-yl)-1H-indole (0.150 g, 0.340 mmol, 1.0 eq) in MeOH (5 mL) was added p-toluenesulfonic acid mono hydrate (0.292 g, 1.70 mmol, 5.0 eq) at room temperature and the mixture was stirred at room temperature for 12 h. After completion of reaction (monitored by TLC, 5% methanol in dichloromethane R$_f$=0.35), methanol was removed under reduced pressure, chilled water was added and the pH was adjusted to 7 with saturated aqueous NaHCO$_3$. The mixture was then extracted with ethyl acetate, the ethyl acetate layer was washed with water followed by brine, dried over anhydrous sodium sulfate, filtered and concentrated under reduced pressure. The crude product was triturated with diethyl ether to afford 1-((1-(methylsulfonyl)piperidin-4-yl)methyl)-5-(1H-pyrazol-4-yl)-1H-indole (0.085 g, 70%) as a white solid. LC-MS: Purity 98.67%; (ES$^+$): m/z 359.40 (M+H$^+$); tr=1.66 min. $^1$H NMR (400 MHz, DMSO-d$_6$) δ 12.80 (brs, 1H), 8.08 (s, 1H), 7.86 (s, 1H), 7.73 (s, 1H), 7.49 (d, J=8.4 Hz, 1H), 7.37 (dd, J=8.4, 1.6 Hz, 1H), 7.32 (d, J=2.8 Hz, 1H), 6.39 (d, J=2.8 Hz, 1H), 4.09 (d, J=7.6 Hz, 2H), 3.52 (d, J=11.6 Hz, 2H), 2.80 (s, 3H), 2.60 (t, J=12 Hz, 2H), 1.96-1.90 (m, 1H), 1.53 (d, J=11.2 Hz, 2H), 1.33-1.24 (m, 2H).

Examples 51-57

Using the method described in example 29 and starting with 1-((5,5-dimethylpyrrolidin-3-yl)methyl)-5-(1-(tetrahydro-2H-pyran-2-yl)-1H-pyrazol-4-yl)-1H-indole and the sulfonyl chlorides shown in the table below, the following can be prepared:

| Example | Sulfonyl Chloride | Product |
|---|---|---|
| 51 | 4-fluorobenzenesulfonyl chloride | 1-((1-((4-fluorophenyl)sulfonyl)-5,5-dimethylpyrrolidin-3-yl)methyl)-5-(1H-pyrazol-4-yl)-1H-indole |
| 52 | 3-fluorobenzenesulfonyl chloride | 1-((3-((3-fluorophenyl)sulfonyl)-5,5-dimethylpyrrolidin-3-yl)methyl)-5-(1H-pyrazol-4-yl)-1H-indole |
| 53 | 2-fluorobenzenesulfonyl chloride | 1-((1-((2-fluorophenyl)sulfonyl)-5,5-dimethylpyrrolidin-3-yl)methyl)-5-(1H-pyrazol-4-yl)-1H-indole |
| 54 | 2,3-difluorobenzenesulfonyl chloride | 1-((1-((2,3-difluorophenyl)sulfonyl)-5,5-dimethylpyrrolidin-3-yl)methyl)-5-(1-pyrazol-4-yl)-1H-indole |

| Example | Sulfonyl Chloride | Product |
|---|---|---|
| 55 | 4-methylbenzenesulfonyl chloride | 1-((5,5-dimethyl-1-tosylpyrrolidin-3-yl)methyl)-5-(1H-pyrazol-4-yl)-1H-indole |
| 56 | 3-methoxybenzenesulfonyl chloride | 1-((1-((3-methoxyphenyl)sulfonyl)-5,5-dimethylpyrrolidin-3-yl)methyl)-5-(1H-pyrazol-4-yl)-1H-indole |
| 57 | 3-cyanobenzenesulfonyl chloride | 3-((4-((5-(1H-pyrazol-4-yl)-1H-indol-1-yl)methyl)-2,2-dimethylpyrrolidin-1-yl)sulfonyl)benzonitrile |

Examples 58-65

Using the methods described in examples 1 and 5, and starting with 1-((5-methylpyrrolidin-3-yl)methyl)-5-(1-(tetrahydro-2H-pyran-2-yl)-1H-pyrazol-4-yl)-1H-indole and the sulfonyl chlorides shown in the table below, the following can be prepared:

| Example | Sulfonyl Chloride | Product |
|---------|-------------------|---------|
| 58 | 4-fluorobenzenesulfonyl chloride | 1-((1-((4-fluorophenyl)sulfonyl)-5-methylpyrrolidin-3-yl)methyl)-5-(1H-pyrazol-4-yl)-1H-indole |
| 59 | 3-fluorobenzenesulfonyl chloride | 1-((1-((3-fluorophenyl)sulfonyl)-5-methylpyrrolidin-3-yl)methyl)-5-(1H-pyrazol-4-yl)-1H-indole |
| 60 | 2-fluorobenzenesulfonyl chloride | 1-((1-((2-fluorophenyl)sulfonyl)-5-methylpyrrolidin-3-yl)methyl)-5-(1H-pyrazol-4-yl)-1H-indole |
| 61 | 2,3-difluorobenzenesulfonyl chloride | 1-((1-((2,3-difluorophenyl)sulfonyl)-5-methylpyrrolidin-3-yl)methyl)-5-(1H-pyrazol-4-yl)-1H-indole |

-continued

| Example | Sulfonyl Chloride | Product |
|---|---|---|
| 62 | (4-methylphenyl)sulfonyl chloride | 1-((5-methyl-1-tosylpyrrolidin-3-yl)methyl)-5-(1H-pyrazol-4-yl)-1H-indole |
| 63 | (3-methoxyphenyl)sulfonyl chloride | 1-((1-((3-methoxyphenyl)sulfonyl)-5-methylpyrrolidin-3-yl)methyl)-5-(1H-pyrazol-4-yl)-1H-indole |
| 64 | 3-cyanobenzenesulfonyl chloride | 3-((4-((5-(1H-pyrazol-4-yl)-1H-indol-1-yl)methyl)-2-methylpyrrolidin-1-yl)sulfonyl)benzonitrile |
| 65 | (3-methylphenyl)sulfonyl chloride | 1-((5-methyl-1-(m-tolylsulfonyl)pyrrolidin-3-yl)methyl)-5-(1H-pyrazol-4-yl)-1H-indole |

Examples 66-73

Using the methods described in example 48, and starting with rac.-trans-1-((-5-methylpyrrolidin-3-yl)methyl)-5-(1-(tetrahydro-2H-pyran-2-yl)-1H-pyrazol-4-yl)-1H-indole and the sulfonyl chlorides shown in the table below, the following can be prepared:

| Example | Sulfonyl Chloride | Product |
|---|---|---|
| 66 | | rac.-trans-1-((1-((4-fluorophenyl)sulfonyl)-5-methylpyrrolidin-3-yl)methyl)-5-(1H-pyrazol-4-yl)-1H-indole |
| 67 | | rac.-trans-1-((1-((3-fluorophenyl)sulfonyl)-5-methylpyrrolidin-3-yl)methyl)-5-(1H-pyrazol-4-yl)-1H-indole |
| 68 | | rac.-trans-1-((1-((2-fluorophenyl)sulfonyl)-5-methylpyrrolidin-3-yl)methyl)-5-(1H-pyrazol-4-yl)-1H-indole |
| 69 | | rac.-trans-1-((1-((2,3-difluorophenyl)sulfonyl)-5-methylpyrrolidin-3-yl)methyl)-5-(1H-pyrazol-4-yl)-1H-indole |

-continued

| Example | Sulfonyl Chloride | Product |
|---|---|---|
| 70 | 4-methylbenzenesulfonyl chloride | rac.-trans-1-((5-methyl-1-tosylpyrrolidin-3-yl)methyl)-5-(1H-pyrazol-4-yl)-1H-indole |
| 71 | 3-methoxybenzenesulfonyl chloride | rac.-trans-1-((1-((3-methoxyphenyl)sulfonyl)-5-methylpyrrolidin-3-yl)methyl)-5-(1H-pyrazol-4-yl)-1H-indole |
| 72 | 3-cyanobenzenesulfonyl chloride | rac.-trans-3-((4-((5-(1H-pyrazol-4-yl)-1H-indol-1-yl)methyl)-2-methylpyrrolidin-1-yl)sulfonyl)benzonitrile |
| 73 | 3-methylbenzenesulfonyl chloride | rac.-trans-1-(((3R,5S)-5-methyl-1-(m-tolylsulfonyl)pyrrolidin-3-yl)methyl)-5-(1H-pyrazol-4-yl)-1H-indole |

Example 74

Human $T_H17$ Cytokine Inhibition as Measured by ELISA

Peripheral blood mononuclear cells (PBMCs) were sourced from freshly prepared leukocyte enriched plasma (buffy coat) from healthy donors (New York Blood Center). PBMCs were isolated by density gradient centrifugation using Ficoll-Paque™ PLUS (GE Healthcare). Human CD4+ T cells were seeded into 96-well plates ($5\times10^4$ cells/well) and activated with plate-bound anti-human (h)-CD3 antibody and soluble h-aCD28 (both at 1 ug/ml; eBioscience) and differentiated into $T_H17$ cells with 20 ng/mL h-IL-6, 5 ng/mL h-TGF-β1, 10 ng/mL h-IL-23 (eBioscience) and 10 ng/mL IL-1 β (Miltenyi Biotec) in serum-free TexMACS Medium (Miltenyi Biotec) supplemented with 1% Penicillin/Streptomycin (Lonza) for 3 days. CD4+ T cells propagated under $T_H17$-polarizing conditions were cultured in the presence or absence of various concentrations of compounds with a final concentration of 0.1% DMSO. Supernatants were collected and stored at −20° C. until assayed for IL-17A, IL-17F and IL-21 levels by "Ready-Set-Go" ELISA kits (eBioscience) as per manufacturer's instructions. Endpoint absorbance was read at 450 nm using a microplate reader (Perkin Elmer). The half maximal inhibitory concentrations ($IC_{50}$) for representative compounds of the invention were determined by GraphPad Prism® software and presented in the table below (wherein "nd" is "not determined"):

| Example Number | IL-17A [IC50 uM] | IL-17F [IC50 uM] | IL-22 [IC50 uM] | IL-21 [IC50 uM] |
|---|---|---|---|---|
| 5 | <10 | <10 | nd | <10 |
| 6 | <10 | <10 | nd | >10 |
| 7 | <10 | <10 | nd | <10 |
| 8 | >10 | >10 | nd | >10 |
| 29 | <10 | <10 | nd | <10 |
| 36 | <10 | <10 | <10 | <10 |
| 38 | <10 | <10 | <10 | <10 |
| 40 | <10 | <10 | <10 | <10 |
| 47 | <10 | <10 | nd | <10 |
| 48 | <10 | <10 | nd | <10 |
| 50 | >10 | >10 | >10 | >10 |

It is to be understood that the invention is not limited to the particular embodiments of the invention described above, as variations of the particular embodiments may be made and still fall within the scope of the appended claims.

We claim:

1. A compound of formula (I):

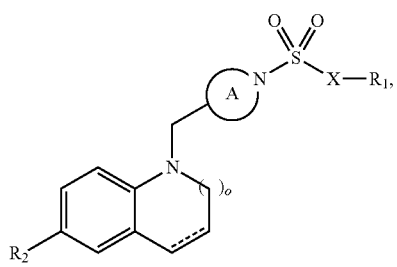

(I)

wherein:
A is a mono- or bicyclic 5- to 8-membered heterocyclic ring having one ring carbon replaced by N as shown, said ring optionally mono- or bisubstituted on one or more ring carbons independently with a $C_1$-$C_6$ alkyl group;

X is —$(CH_2)_n$—;

$R_1$ is —$C_1$-$C_6$ alkyl, optionally substituted with one or more —OH, halogen or —CN,
phenyl, optionally mono- or bisubstituted independently with halogen, alkoxy, $C_1$-$C_6$ alkyl, —CN, -sulfonyloxy, alkylsulfonyl, halo-$C_1$-$C_6$ alkyl or $C_3$-$C_5$ cycloalkyl,
cycloalkyl, optionally substituted,
heterocycle, optionally substituted or
a 5- or 6-membered heteroaryl group having one or more ring carbons independently replaced by N, O or S, said heteroaryl optionally mono- or bisubstituted independentlywith halogen, alkoxy, $C_1$-$C_6$ alkyl, —CN or perfluorinated $C_1$-$C_6$ alkyl;

$R_2$ is a 5- to 7-membered heteroaryl group having one, two or three ring carbons independently replaced by N, O or S, said heteroaryl optionally mono- or bisubstituted independently with H, $C_1$-$C_6$ alkyl, —CN or (=O);

=== is a single or double bond;
o is 0 or 1; and
n is 0, 1 or 2;

or a pharmaceutically acceptable salt thereof.

2. The compound according to claim 1, wherein A is unsubstituted piperidinyl, pyrrolidinyl, azepanyl or [2,2,1] bicycloazepinyl.

3. The compound according to claim 1, wherein A is piperidinyl, pyrrolidinyl or azepanyl mono- or bisubstituted independently with a $C_1$-$C_6$ alkyl group.

4. The compound according to claim 1, wherein A is piperidinyl, pyrrolidinyl or azepanyl monosubstituted with methyl.

5. The compound according to claim 1, wherein A is piperidinyl, pyrrolidinyl or azepanyl bisubstituted with methyl.

6. The compound according to claim 1, wherein X is methylene or ethylene.

7. The compound according to claim 1, wherein X is absent.

8. The compound according to claim 1, wherein $R_1$ is —$C_1$-$C_6$ alkyl.

9. The compound according to claim 1, wherein $R_1$ is methyl, ethyl, propyl or t-butyl.

10. The compound according to claim 1, wherein $R_1$ is unsubstituted phenyl.

11. The compound according to claim 1, wherein $R_1$ is phenyl mono- or bisubstituted with halogen, cyano, alkoxy, $C_1$-$C_6$ alkyl or halo-$C_1$-$C_6$ alkyl.

12. The compound according to claim 1, wherein $R_1$ is chlorophenyl, fluorophenyl or dihalophenyl.

13. The compound according to claim 1, wherein $R_1$ is methoxy-phenyl.

14. The compound according to claim 1, wherein $R_1$ is methyl-phenyl, cyanophenyl or alkoxyphenyl.

15. The compound according to claim 1, wherein $R_1$ is cycloalkyl.

16. The compound according to claim 1, wherein $R_1$ is cyclohexyl.

17. The compound according to claim 1, wherein $R_1$ is an unsubstituted 5- or 6-membered heteroaryl group having one or more ring carbons replaced by N.

18. The compound according to claim 1, wherein $R_1$ is a 5- or 6-membered heteroaryl group having one or more ring carbons replaced by N, substituted with a $C_1$-$C_6$ alkyl group.

19. The compound according to claim 1, wherein $R_1$ is pyridinyl.

20. The compound according to claim 1, wherein $R_2$ is an unsubstituted 5- to 7-membered heteroaryl group having one, two or three ring carbons replaced by N.

21. The compound according to claim 1, wherein $R_2$ is a 5- to 7-membered heteroaryl group having one, two or three ring carbons replaced by N, said heteroaryl group mono- or bisubstituted independently with H, $C_1$-$C_6$ alkyl, —CN or (=O).

22. The compound according to claim 1, wherein $R_2$ is unsubstituted pyrazolyl, triazolyl, pyridinyl, pyrazinyl or thiazole.

23. The compound according to claim 1, wherein $R_2$ is pyrazolyl or triazolyl.

24. The compound according to claim 1, wherein $R_2$ is unsubstituted pyrazolyl.

25. The compound according to claim 1, wherein $R_2$ is linked via a carbon atom.

26. The compound according to claim 1, having the formula (Ia):

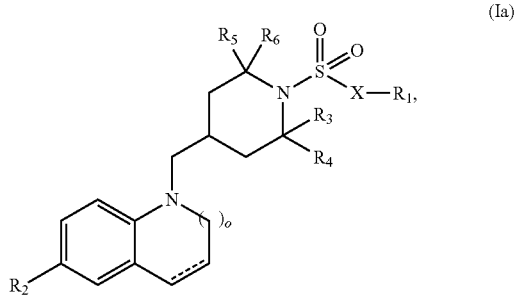

wherein:
X is —$(CH_2)_n$—;
$R_1$ is —$C_1$-$C_6$ alkyl, optionally substituted with one or more —OH, halogen or —CN,
 phenyl, optionally mono- or bisubstituted independently with halogen, alkoxy, $C_1$-$C_6$ alkyl, —CN, -sulfonyloxy, alkylsulfonyl, halo-$C_1$-$C_6$ alkyl or $C_3$-$C_5$ cycloalkyl,
 cycloalkyl, optionally substituted,
 heterocycle, optionally substituted or
 a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN or perfluorinated $C_1$-$C_6$ alkyl;
$R_2$ is a 5- to 7-membered heteroaryl group having one, two or three ring carbons independently replaced by N, O or S, said heteroaryl optionally mono- or bisubstituted independently with H, $C_1$-$C_6$ alkyl, —CN or (=O);
$R_3$, $R_4$, $R_5$ and $R_6$ are independently —H or $C_1$-$C_6$ alkyl;
=== is a single or double bond;
o is 0 or 1; and
n is 0, 1 or 2,
or a pharmaceutically acceptable salt thereof.

27. The compound according to claim 1, having the formula (Ib):

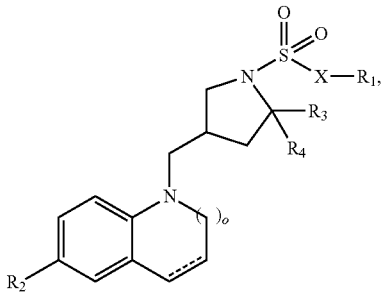

wherein:
X is —$(CH_2)_n$—;
$R_1$ is —$C_1$-$C_6$ alkyl, optionally substituted with one or more —OH, halogen or —CN,
 phenyl, optionally mono- or bisubstituted independently with halogen, alkoxy, $C_1$-$C_6$ alkyl, —CN, -sulfonyloxy, alkylsulfonyl, halo-$C_1$-$C_6$ alkyl or $C_3$-$C_5$cycloalkyl,
 cycloalkyl, optionally substituted,
 heterocycle, optionally substituted, or
 a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN or perfluorinated $C_1$-$C_6$ alkyl;
$R_2$ is a 5- to 7-membered heteroaryl group having one, two or three ring carbons independently replaced by N, O or S, said heteroaryl optionally mono- or bisubstituted independently with H, $C_1$-$C_6$ alkyl, —CN or (=O);
$R_3$ and $R_4$ are independently —H or $C_1$-$C_6$ alkyl;
=== is a single or double bond;
o is 0 or 1; and
n is 0, 1 or 2;
or a pharmaceutically acceptable salt thereof.

28. The compound according to claim 1, having the formula (Ic):

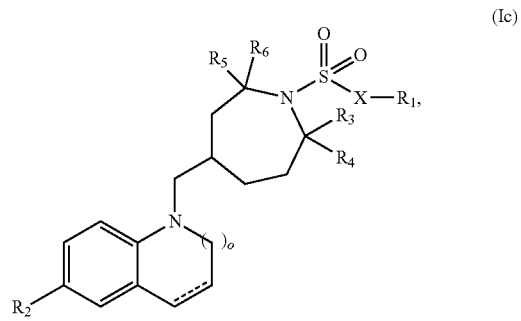

wherein:
X is —$(CH_2)_n$—;
$R_1$ is —$C_1$-$C_6$ alkyl, optionally substituted with one or more —OH, halogen or —CN,
 phenyl, optionally mono- or bisubstituted independently with halogen, alkoxy, $C_1$-$C_6$ alkyl, —CN, -sulfonyloxy, alkylsulfonyl, halo-$C_1$-$C_6$ alkyl or $C_3$-$C_5$ cycloalkyl,
 cycloalkyl, optionally substituted,
 heterocycle, optionally substituted, or a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN or perfluorinated $C_1$-$C_6$ alkyl;

$R_2$ is a 5- to 7-membered heteroaryl group having one, two or three ring carbons independently replaced by N, O or S, said heteroaryl optionally mono- or bisubstituted independently with H, $C_1$-$C_6$ alkyl, —CN or (=O);

$R_3$, $R_4$, $R_5$ and $R_6$ are independently —H or $C_1$-$C_6$ alkyl;
=== is a single or double bond;
o is 0 or 1; and
n is 0, 1 or 2;
or a pharmaceutically acceptable salt thereof.

29. The compound according to claim 1, having the formula (Id):

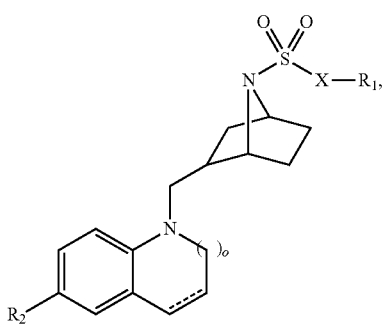

wherein:
X is —(CH$_2$)$_n$—;
$R_1$ is —$C_1$-$C_6$ alkyl, optionally substituted with one or more —OH, halogen or —CN,
phenyl, optionally mono- or bisubstituted independently with halogen, alkoxy, $C_1$-$C_6$ alkyl, —CN, -sulfonyloxy, alkylsulfonyl, halo-$C_1$-$C_6$ alkyl or $C_3$-$C_5$ cycloalkyl,
cycloalkyl, optionally substituted,
heterocycle, optionally substituted, or
a 5- or 6-membered heteroaryl group having one or more ring carbons independently replaced by N, O or S, said heteroaryl optionally mono- or bisubstituted independently with halogen, alkoxy, $C_1$-$C_6$ alkyl, —CN or perfluorinated $C_1$-$C_6$ alkyl;

$R_2$ is a 5- to 7-membered heteroaryl group having one, two or three ring carbons independently replaced by N, O or S, said heteroaryl optionally mono- or bisubstituted independently with H, $C_1$-$C_6$ alkyl, —CN or (=O);
=== is a single or double bond;
o is 0 or 1; and
n is 0, 1 or 2;
or a pharmaceutically acceptable salt thereof.

30. The compound according to claim 1, wherein said compound is:
1-((1-(phenylsulfonyl)piperidin-4-yl)methyl)-5-(1H-pyrazol-4-yl)-1H-indole,
1-((1-(benzylsulfonyl)piperidin-4-yl)methyl)-5-(1H-pyrazol-4-yl)-1H-indole,
1-((1-(phenethylsulfonyl)piperidin-4-yl)methyl)-5-(1H-pyrazol-4-yl)-1H-indole,
5-(1H-pyrazol-4-yl)-1-((1-((2,2,2-trifluoroethyl)sulfonyl)piperidin-4-yl)methyl)-1H-indole;
1-((1-(4-chlorophenylsulfonyl)piperidin-4-yl)methyl)-5-(1H-pyrazol-4-yl)-1H-indole,
5-(1H-pyrazol-4-yl)-1-((1-(pyridin-3-ylsulfonyl)piperidin-4-yl)methyl)-1H-indole,
1-((1-(methylsulfonyl)piperidin-4-yl)methyl)-5-(1H-pyrazol-4-yl)-1H-indole,
1-((1-(2-fluorophenylsulfonyl)piperidin-4-yl)methyl)-5-(1H-pyrazol-4-yl)-1H-indole,
cis-1-((5-methyl-1-(phenylsulfonyl)pyrrolidin-3-yl)methyl)-5-(1H-pyrazol-4-yl)-1H-indole or
trans-1-((5-methyl-1-(phenylsulfonyl)pyrrolidin-3-yl)methyl)-5-(1H-pyrazol-4-yl)-1H-indole,
1-((1-(2-fluorophenylsulfonyl)piperidin-4-yl)methyl)-5-(1H-pyrazol-4-yl)-1H-indole.

31. The compound according to claim 1, wherein said compound is:
1-((1-(phenylsulfonyl)pyrrolidin-3-yl)methyl)-5-(1H-pyrazol-4-yl)-1H-indole,
1-((1-(benzylsulfonyl)pyrrolidin-3-yl)methyl)-5-(1H-pyrazol-4-yl)-1H-indole,
1-((1-(phenethylsulfonyl)pyrrolidin-3-yl)methyl)-5-(1H-pyrazol-4-yl)-H-indole,
1-((1-(tert-butylsulfonyl)pyrrolidin-3-yl)methyl)-5-(1H-pyrazol-4-yl)-1H-indole,
1-((5-methyl-1-(phenylsulfonyl)pyrrolidin-3-yl)methyl)-5-(1H-pyrazol-4-yl)-1H-indole,
1-((1-(benzylsulfonyl)-5-methylpyrrolidin-3-yl)methyl)-5-(1H-pyrazol-4-yl)-1H-indole,
((5-methyl-1-(phenethylsulfonyl)pyrrolidin-3-yl)methyl)-5-(1H-pyrazol-4-yl)-1H-indole,
1-((1-(tert-butylsulfonyl)-5-methylpyrrolidin-3-yl)methyl)-5-(1H-pyrazol-4-yl)-1H-indole,
1-((1-(phenylsulfonyl)azepan-4-yl)methyl)-5-(1H-pyrazol-4-yl)-1H-indole,
1-((1-(benzylsulfonyl)azepan-4-yl)methyl)-5-(1H-pyrazol-4-yl)-1H-indole,
1-((1-(phenethylsulfonyl)azepan-4-yl)methyl)-5-(1H-pyrazol-4-yl)-1H-indole,
1-((1-(tert-butylsulfonyl)azepan-4-yl)methyl)-5-(1H-pyrazol-4-yl)-1H-indole,
1-((7-(phenylsulfonyl)-7-azabicyclo[2.2.1]heptan-2-yl)methyl)-5-(1H-pyrazol-4-yl)-1H-indole,
1-((7-(benzylsulfonyl)-7-azabicyclo[2.2.1]heptan-2-yl)methyl)-5-(1H-pyrazol-4-yl)-1H-indole,
1-((7-(phenethylsulfonyl)-7-azabicyclo[2.2.1]heptan-2-yl)methyl)-5-(1H-pyrazol-4-yl)-1H-indole,
1-((7-(tert-butylsulfonyl)-7-azabicyclo[2.2.1]heptan-2-yl)methyl)-5-(1H-pyrazol-4-yl)-1H-indole,
1-((1-(phenylsulfonyl)piperidin-4-yl)methyl)-6-(1H-pyrazol-4-yl)-1,2,3,4-tetrahydroquinoline,
1-((1-(benzylsulfonyl)piperidin-4-yl)methyl)-6-(1H-pyrazol-4-yl)-1,2,3,4-tetrahydroquinoline,
1-((1-(phenethylsulfonyl)piperidin-4-yl)methyl)-6-(1H-pyrazol-4-yl)-1,2,3,4-tetrahydroquinoline,
1-((1-(tert-butylsulfonyl)piperidin-4-yl)methyl)-6-(1H-pyrazol-4-yl)-1,2,3,4-tetrahydroquinoline,
1-((5,5-dimethyl-1-(phenylsulfonyl)pyrrolidin-3-yl)methyl)-5-(1H-pyrazol-4-yl)-1H-indole,
1-((1-(benzylsulfonyl)-5,5-dimethylpyrrolidin-3-yl)methyl)-5-(1H-pyrazol-4-yl)-1H-indole,
1-((5,5-dimethyl-1-(phenethylsulfonyl)pyrrolidin-3-yl)methyl)-5-(1H-pyrazol-4-yl)-1H-indole,
1-((1-(tert-butylsulfonyl)-5,5-dimethylpyrrolidin-3-yl)methyl)-5-(1H-pyrazol-4-yl)-1H-indole, 5-(1H-pyrazol-4-yl)-1-((1-(m-tolylsulfonyl)piperidin-4-yl)methyl)-1H-indole,
1-((1-((4-methoxyphenyl)sulfonyl)piperidin-4-yl)methyl)-5-(1H-pyrazol-4-yl)-1H-indole,
1-((1-((4-fluorophenyl)sulfonyl)piperidin-4-yl)methyl)-5-(1H-pyrazol-4-yl)-1H-indole,
3-((4-((5-(1H-pyrazol-4-yl)-1H-indol-1-yl)methyl)piperidin-1-yl)sulfonyl)benzonitrile,
1-((1-((4-(difluoromethyl)phenyl)sulfonyl)piperidin-4-yl)methyl)-5-(1H-pyrazol-4-yl)-1H-indole,
1-((1-((3-fluorophenyl)sulfonyl)piperidin-4-yl)methyl)-5-(1H-pyrazol-4-yl)-1H-indole,
1-((1-((4-fluorophenyl)sulfonyl)-5,5-dimethylpyrrolidin-3-yl)methyl)-5-(1H-pyrazol-4-yl)-1H-indole,
1-((1-((2-fluorophenyl)sulfonyl)-5,5-dimethylpyrrolidin-3-yl)methyl)-5-(1H-pyrazol-4-yl)-1H-indole,
1-((1-((2,3-difluorophenyl)sulfonyl)-5,5-dimethylpyrrolidin-3-yl)methyl)-5-(1H-pyrazol-4-yl)-1H-indole,
1-((5,5-dimethyl-1-tosylpyrrolidin-3-yl)methyl)-5-(1H-pyrazol-4-yl)-1H-indole,
1-((1-((3-methoxyphenyl)sulfonyl)-5,5-dimethylpyrrolidin-3-yl)methyl)-5-(1H-pyrazol-4-yl)-1H-indole,
3-((4-((5-(1H-pyrazol-4-yl)-1H-indol-1-yl)methyl)-2,2-dimethylpyrrolidin-1-yl)sulfonyl)benzonitrile,
1-((1-((4-fluorophenyl)sulfonyl)-5-methylpyrrolidin-3-yl)methyl)-5-(1H-pyrazol-4-yl)-1H-indole,
1-((1-((3-fluorophenyl)sulfonyl)-5-methylpyrrolidin-3-yl)methyl)-5-(1H-pyrazol-4-yl)-1H-indole,
1-((1-((2-fluorophenyl)sulfonyl)-5-methylpyrrolidin-3-yl)methyl)-5-(1H-pyrazol-4-yl)-1H-indole,
1-((1-((2-fluorophenyl)sulfonyl)-5-methylpyrrolidin-3-yl)methyl)-5-(1H-pyrazol-4-yl)-1H-indole,
1-((1-((2,3-difluorophenyl)sulfonyl)-5-methylpyrrolidin-3-yl)methyl)-5-(1H-pyrazol-4-yl)-1H-indole,
1-((5-methyl-1-tosylpyrrolidin-3-yl)methyl)-5-(1H-pyrazol-4-yl)-1H-indole,
1-((1-((3-methoxyphenyl)sulfonyl)-5-methylpyrrolidin-3-yl)methyl)-5-(1H-pyrazol-4-yl)-1H-indole,
3-((4-((5-(1H-pyrazol-4-yl)-1H-indol-1-yl)methyl)-2-methylpyrrolidin-1-yl)sulfonyl)benzonitrile,
1-((5-methyl-1-(m-tolylsulfonyl)pyrrolidin-3-yl)methyl)-5-(1H-pyrazol-4-yl)-1H-indole,
rac-cis-1-((1-((4-fluorophenyl)sulfonyl)-5-methylpyrrolidin-3-yl)methyl)-5-(1H-pyrazol-4-yl)-1H-indole,
rac.-cis-1-((1-((3-fluorophenyl)sulfonyl)-5-methylpyrrolidin-3-yl)methyl)-5-(1H-pyrazol-4-yl)-1H-indole,
rac.-1-cis-((1-((2-fluorophenyl)sulfonyl)-5-methylpyrrolidin-3-yl)methyl)-5-(1H-pyrazol-4-yl)-1H-indole,
rac.-1-cis-((1-((2,3-difluorophenyl)sulfonyl)-5-methylpyrrolidin-3-yl)methyl)-5-(1H-pyrazol-4-yl)-1H-indole,
rac.-1-cis-((5-methyl-1-tosylpyrrolidin-3-yl)methyl)-5-(1H-pyrazol-4-yl)-1H-indole,
rac.-1-cis-((1-((3-methoxyphenyl)sulfonyl)-5-methylpyrrolidin-3-yl)methyl)-5-(1H-pyrazol-4-yl)-1H-indole,
rac.-3-cis-((4-((5-(1H-pyrazol-4-yl)-1H-indol-1-yl)methyl)-2-methylpyrrolidin-1-yl)sulfonyl)benzonitrile or
rac.-1-cis-((5-methyl-1-(m-tolylsulfonyl)pyrrolidin-3-yl)methyl)-5-(1H-pyrazol-4-yl)-1H-indole,
rac.-trans-1-((1-((4-fluorophenyl)sulfonyl)-5-methylpyrrolidin-3-yl)methyl)-5-(1H-pyrazol-4-yl)-1H-indole,
rac.-trans-1-((1-((3-fluorophenyl)sulfonyl)-5-methylpyrrolidin-3-yl)methyl)-5-(1H-pyrazol-4-yl)-1H-indole,
rac.-1-trans-((1-((2-fluorophenyl)sulfonyl)-5-methylpyrrolidin-3-yl)methyl)-5-(1H-pyrazol-4-yl)-1H-indole,
rac.-1-trans-((1-((2,3-difluorophenyl)sulfonyl)-5-methylpyrrolidin-3-yl)methyl)-5-(1H-pyrazol-4-yl)-1H-indole,
rac.-1-trans-((5-methyl-1-tosylpyrrolidin-3-yl)methyl)-5-(1H-pyrazol-4-yl)-1H-indole,
rac.-1-trans-((1-((3-methoxyphenyl)sulfonyl)-5-methylpyrrolidin-3-yl)methyl)-5-(1H-pyrazol-4-yl)-1H-indole,
rac.-3-trans-((4-((5-(1H-pyrazol-4-yl)-1H-indol-1-yl)methyl)-2-methylpyrrolidin-1-yl)sulfonyl)benzonitrile or
rac.-1-trans-((5-methyl-1-(m-tolylsulfonyl)pyrrolidin-3-yl)methyl)-5-(1H-pyrazol-4-yl)-1H-indole.

32. A pharmaceutical composition, comprising a therapeutically effective amount of a compound according to claim 1, or a pharmaceutically acceptable salt thereof, and a pharmaceutically acceptable carrier.

33. A method of treating a Retinoic Acid Receptor-Related Orphan Receptor regulated disease or disorder, comprising the step of administering a therapeutically effective amount of a compound according to claim 1, or a pharmaceutically acceptable salt thereof, to a patient in need thereof.

34. The method according to claim 33, wherein said disease or disorder is an autoimmune, inflammatory, metabolic or oncologic disease or disorder.

35. The method according to claim 34, wherein said disease or disorder is rheumatoid arthritis, psoriasis, psoriatic arthritis, polymyalgia rheumatica, multiple sclerosis, lupus, uveitis, inflammatory bowel disease, ankylosing spondylitis, vasculitis, atherosclerosis, macular degeneration, diabetes, obesity, cancer, asthma or chronic obstructive pulmonary disease.

* * * * *